US012680107B2

(12) United States Patent
Mujica et al.

(10) Patent No.: US 12,680,107 B2
(45) Date of Patent: Jul. 14, 2026

(54) NON-HUMAN ANIMALS COMPRISING A HUMANIZED ASGR1 LOCUS

(71) Applicant: Regeneron Pharmaceuticals, Inc., Tarrytown, NY (US)

(72) Inventors: Alexander O. Mujica, Elmsford, NY (US); Viktoria Gusarova, Pleasantville, NY (US); Cheng Wang, Beijing (CN); Christos Kyratsous, Irvington, NY (US); Terra Potocky, Dobbs Ferry, NY (US); Katherine Cygnar, New York, NY (US); Joel H. Martin, Putnam Valley, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 544 days.

(21) Appl. No.: 18/320,789

(22) Filed: May 19, 2023

(65) Prior Publication Data

US 2023/0345919 A1 Nov. 2, 2023

Related U.S. Application Data

(62) Division of application No. 16/625,168, filed as application No. PCT/US2018/039864 on Jun. 27, 2018, now Pat. No. 11,696,572.

(60) Provisional application No. 62/525,524, filed on Jun. 27, 2017.

(51) Int. Cl.
| | |
|---|---|
| *C12N 15/85* | (2006.01) |
| *A01K 67/0278* | (2024.01) |
| *C07K 14/705* | (2006.01) |
| *C12N 5/071* | (2010.01) |
| *C12N 5/10* | (2006.01) |

(52) U.S. Cl.
CPC ...... *C12N 15/8509* (2013.01); *A01K 67/0278* (2013.01); *C07K 14/7056* (2013.01); *C12N 15/85* (2013.01); *A01K 2207/15* (2013.01); *A01K 2217/072* (2013.01); *A01K 2227/105* (2013.01); *C12N 5/0608* (2013.01); *C12N 5/10* (2013.01)

(58) Field of Classification Search
CPC ...... C12N 15/8509; C12N 15/85; C12N 5/10; A01K 67/0278; A01K 2207/15; A01K 2271/072; A01K 2227/105; C07K 14/7056
USPC .......................................... 435/320.1; 800/18
See application file for complete search history.

(56) References Cited

U.S. PATENT DOCUMENTS

| | | | |
|---|---|---|---|
| 7,294,754 B2 | 11/2007 | Poueymirou et al. | |
| 7,576,259 B2 | 8/2009 | Poueymirou et al. | |
| 7,612,250 B2 | 11/2009 | Overstrom et al. | |
| 7,659,442 B2 | 2/2010 | Poueymirou et al. | |
| 8,586,713 B2 | 11/2013 | Davis et al. | |
| 8,697,851 B2 | 4/2014 | Frendewey et al. | |
| 11,696,572 B2 * | 7/2023 | Mujica ............... | A01K 67/0278 |
| | | | 800/3 |
| 2004/0177390 A1 | 9/2004 | Lewis et al. | |
| 2005/0144655 A1 | 6/2005 | Economides et al. | |
| 2008/0092249 A1 | 4/2008 | Lewis et al. | |
| 2011/0104799 A1 | 5/2011 | Economides et al. | |
| 2013/0243775 A1 | 9/2013 | Papadopoulos et al. | |
| 2013/0309670 A1 | 11/2013 | Frendewey et al. | |
| 2013/0312129 A1 | 11/2013 | Frendewey et al. | |
| 2014/0178879 A1 | 6/2014 | Economides et al. | |
| 2014/0235933 A1 | 8/2014 | Lee et al. | |
| 2015/0159175 A1 | 6/2015 | Frendewey et al. | |
| 2016/0145646 A1 | 5/2016 | Frendewey et al. | |
| 2017/0164588 A1 * | 6/2017 | Olson ................ | C12N 15/8509 |
| 2019/0112588 A1 * | 4/2019 | Baik .............. | C12Y 301/04041 |

FOREIGN PATENT DOCUMENTS

| | | |
|---|---|---|
| WO | 1999005266 A2 | 2/1999 |
| WO | 2008017234 A1 | 2/2008 |
| WO | 2009019312 A2 | 2/2009 |
| WO | 2013138400 A1 | 9/2013 |
| WO | 2013176772 A1 | 11/2013 |
| WO | 2014023709 A1 | 2/2014 |
| WO | 2014033644 A2 | 3/2014 |
| WO | 2014089290 A1 | 6/2014 |
| WO | 2016010840 A1 | 1/2016 |
| WO | 2016081923 A2 | 5/2016 |
| WO | 2016085889 A1 | 6/2016 |

(Continued)

OTHER PUBLICATIONS

Meier et al. (2000) J. Mol. Biol., vol. 300, 857-865.*
Spiess et al. (1985) J. Biol. Chem., vol. 260(4), 1979-1982.*
Monroe et al. (1994) Gene, vol. 148, 237-244.*
Liu et al. (2010) PLoS One, vol. 5(9), e12934, pp. 1-13.*
Devoy et al. (2011) Nat. Genet., vol. 13, 14-20.*
Sibilia et al., (2003) Development, vol. 130, 4515-4525.*
Accession NCBI—HomoloGene:1263. Gene conserved in Boreoeutheria.
Accession NCBI Reference Sequence: NM_001671.5 "Homo sapiens asialoglycoprotein receptor 1 (ASGR1), transcript variant 1, mRNA".

(Continued)

*Primary Examiner* — Anne Marie S Wehbe

(74) *Attorney, Agent, or Firm* — FisherBroyles, LLP; Rita S. Wu; Trisha Agrawal

(57) ABSTRACT

Non-human animal cells and non-human animals comprising a humanized Asgr1 locus and methods of using such non-human animal cells and non-human animals are provided. Non-human animal cells or non-human animals comprising a humanized Asgr1 locus express a human ASGR1 protein or an Asgr1 protein, fragments of which are from human ASGR1. Methods are provided for using such non-human animals comprising a humanized Asgr1 locus to assess in vivo efficacy of human-ASGR1-mediated delivery of therapeutic molecules or therapeutic complexes to the liver and to assess the efficacy of therapeutic molecules or therapeutic complexes acting via human-ASGR1-mediated mechanisms.

6 Claims, 13 Drawing Sheets

Specification includes a Sequence Listing.

(56)                    References Cited

FOREIGN PATENT DOCUMENTS

WO         2017087780 A1      5/2017
WO         2017100467 A2      6/2017

OTHER PUBLICATIONS

Accession NCBI Reference Sequence: NM_009714.3 "Mus musculus asialoglycoprotein receptor 1 (Asgr1), transcript variant 1, mRNA".
Accession UniProtKB/Swiss-Prot: P02706.2.
Accession UniProtKB/Swiss-Prot: P07306.2.
Accession UniProtKB/Swiss-Prot: P34927.4.
Accession UniProtKB/Swiss-Prot: Q5RBQ8.3.
Aravalli et al., "Liver-Targeted Gene Therapy: Approaches and Challenges," Liver Transplantation, 21:718-737 (2015).
Arden and Metzger, "Inexpensive, serotype-independent protocol for native and bioengineered recombinant adeno-associated virus purification," J. Biol. Methods., 3(2):e38 (2016).
Aurnhammer et al., "Universal Real-Time PCR for the Detection and Quantification of Adeno-Associated Virus Serotype 2-Derived Inverted Terminal Repeat Sequences," Hum. Gene Ther. Methods, Part B, 23:18-28 (2012).
Bonamassa et al., (Author Manuscript) "Hydrodynamic Gene Delivery and Its Applications in Pharmaceutical Research," Pharm. Res., 28(4):694-701 (2011).
Brevini et al. (2010) "Embryonic Stem Cells in Domestic Animals; No shortcuts to pig embryonic stem cells," Theriogenology, 74:544-550.
Cao et al., (2009) "Isolation and Culture of Primary Bovine Embryonic Stem Cell Colonies by a Novel Method," Journal of Experimental Zoology, 311A:368-376.
Cho et al., (Author Manuscript) "Generation of Transgenic Mice," Current Protocols in Cell Biology vol. 42:19.11:19.11.1-19.11.22 (Mar. 2009).
Coulstock et al., "Liver-Targeting of Interferon-Alpha with Tissue-Specific Domain Antibodies," PLoS One, 8(2):e57263 (2013).
Dennis, "Welfare issues of genetically modified animals," ILAR Journal, 43(2):100-109 (2002).
D'Souza and Devarajan, "Asialoglycoprotein receptor mediated hepatocyte targeting—Strategies and applications," Journal of Controlled Release, 203:126-139 (2015).
Devoy et al., "Genomically humanized mice: technologies and promises," Nat. Rev. Genet., Author Manuscript, 2012, 13(1):14-20, doi:10.1038/nrg3116.
Devoy et al., "Genomically humanized mice: technologies and promises," Nat. Rev. Genet., 13:14-20 (Jan. 2012).
Festing et al., "Revised nomenclature for strain 129 mice," Mammalian Genome, 10:836 (1999).
Frendewey et al., "The Loss-of-Allele Assay for ES Cell Screening and Mouse Genotyping," Methods Enzymol., 476:295-307 (2010).
Gama Sosa et al., "Animal transgenesis: an overview," Brain Struct. Funct., 214(2-3):91-109 (2010).
Glick and Pasternak Dzh. Moleculyarnaya biotehnologiya. Printsipy i primeneniye. Moscow: Mir, 2002 (with English translation).
Hofker Martin et al. (2003) "Transgenic mouse methods and protocols," Methods in Molecular Biology, 209:51-58.
Houdebine (2009) "Methods to Generate Transgenic Animals," Genetic Engineering in Livestock, New Applications and Interdisciplinary Perspectives, Engelhard M, et al., 2009, XVI, 1 46 p. 8 illus., pp. 31-48, see p. 36.
Kasparek & Humphrey (2011) Seminars in Cell & Dev. Biol. 22:886-897.
Li and Elledge , "SLIC: A Method for Sequence- and Ligation-Independent Cloning," Chapter 5, Methods Mol. Biol., 852:51-59 (2012).

Liu et al., "A New Splice Variant of the Major Subunit of Human Asialoglycoprotein Receptor Encodes a Secreted Form in Hepatocytes," PLoS One, Sep. 2010, 5(9):e12934, pp. 1-13.
Loisel et al., "Relevance, advantages and limitations of animal models used in the development of monoclonal antibodies for cancer treatment," Oncology Hematology, 62(1):34-42 (2007).
Mandalos et al., "Application of a Novel Strategy of Engineering Conditional Alleles to a Single Exon Gene, Sox2," PLoS One 7:e45768:1-9 (2012).
Maresca et al., "Obligate Ligation-Gated Recombination (ObLiGaRe): Custom-designed nuclease-mediated targeted integration through nonhomologous end joining," Genome Res., 23(3):539-546 (2013).
Meier et al., "Crystal Structure of the Carbohydrate Recognition Domain of the H1 Subunit of the Asialoglycoprotein Receptor," J. Mol. Biol., 2000, 300:857-865.
Monroe and Huber, "The major form of the murine asialoglycoprotein receptor: cDNA sequence and expression in liver, testis and epididymis," Gene, Oct. 1994, 148(2):237-244.
Nakamura et al., Codon usage tabulated from international DNA sequence databases: status for the year 2000, Nucleic Acids Research, 28:292 (2000).
Paris and Stout (2010) "Embryonic Stem Cells in Domestic Animals; Equine embryos and ebryonic stem cells: Defining reliable markers of pluripotency," Theriogenology, 74:516-524.
Poueymirou et al., "F0 generation mice fully derived from gene-targeted embryonic stem cells allowing immediate phenotypic analyses," Nature Biotech. 25(1):91-99 (2007).
R & D Systems, MAB27552, Product Data Sheet, "Mouse ASGR1/ASGPR1 Antibody" Rev. Feb. 26, 2018.
Rybchin V.N., (2002) "Basics of Genetic Engineering," Saint-Petersburg, Publishing House of Saint-Petersburg State Technology Institute, p. 411-413 (submitted with the English translation of the Office Action, where cited).
Sabrautzki et al., "New mouse models for metabolic bone diseases generated by genome-wide ENU mutagenesis," Mamm. Genome, 23:416-430 (2012).
Sands and Davidson, "Gene Therapy for Lysosomal Storage Diseases," Molecular Therapy, May 2006, 13(5):839-849.
Sibilia et al., Mice humanised for the EGF receptor display hypomorphic phenotypes in skin, bone and heart, Development,130(19):4515-4525 (2003).
Spiess et al., "Sequence of Human Asialoglycoprotein Receptor cDNA," J. Biol. Chem., 1985, 260(4):1979-1982.
Sun et al., "Expression pattern of asialoglycoprotein receptor in human testis," Cell Tissue Res., 2013, 352:761-768.
Tan et al., "Antibody targeted gene transfer to endothelium," Journal of Gene Medicine, 2003, 5:311-323.
Trahtenherts and Benhar, "An Internalizing Antibody Specific for the Human Asialoglycoprotein Receptor," Hybridoma, 28(4):225-233 (2009).
Wang et al., "One-Step Generation of Mice Carrying Mutations in Multiple Genes by CRISPR/Cas-Mediated Genome Engineering," Cell, 153:910-918 (2013).
Wang et al., "TALEN-mediated editing of the Mouse Y Chromosome," Nat. Biotechnol., 31:530-532 (2013).
Zhou et al., "Developing tTA transgenic rats for inducible and reversible gene expression," International Journal of Biological Sciences, 5:171-181 (2009).
International Search Report and Written Opinion with respect to PCT/US2018/039864 mailed Sep. 14, 2018.
English Translation of Office Action with respect to Russia Application No. 2020101936 mailed Mar. 1, 2022.
Liu., "Cis-Regulatory Elements in Mammals," International Journal of Molecular Sciences, 25(343):1-21, (2023).

* cited by examiner

TM

```
hASGR1      1  MTKEYQDLQHLDNEESDHHQLRKGPPPPPQLLQRLCSGPRLLLLSLGLSLILLLVVVCVIG   60
mAsgrl      1  MTKDYQDFQHLDND-NDHHQLRRGPPPTPRLLQRLCSGSRLLLLSSSLSILLLVVVCVIT   59
7302 humIn  1  MTKDYQDFQHLDND-NDHHQLRRGPPPTPRLLQRLCSGSRLLLLSSSLSILLLVVVCVIT   59
               ***  ****  ****   ****** *****  ********* **   ** **********
```

Coiled-coil

```
hASGR1     61  SQNSQLQEELRGLRETFSNFTASTEAQVKGLSTQGGNVGRKMKSLESQLEKQQKDLSEDH  120
mAsgrl     60  SQNSQLREDILALRQNESNLTVSTEDQVKALSTQGSSVGRKMKLVESKLEKQQKDLTEDH  119
7302 humIn 60  SQNSQLQEELRGLRETFSNFTASTEAQVKGLSTQGGNVGRKMKSLESQLEKQQKDLSEDH  119
               ******  *   * *  *** ****  *** ****** ******  **  ********* ***
```

Coiled-coil      C-type lectin

```
hASGR1    121  SSLLLHVKQFVSDLRSLSCQMAALQGNGSERTCCPVNWVEHERSCYWFSRSGKAWADADN  180
mAsgrl    120  SSLLLHVKQLVSDVRSLSCQMAAFRGNGSERTCCPINWVEYEGSCYWFSSSVRPWTEADK  179
7302 humIn 120 SSLLLHVKQFVSDLRSLSCQMAALQGNGSERTCCPVNWVEHERSCYWFSRSGKAWADADN  179
               *********  ***  ********* ***********  ****  *  *****   *   *  **
```

C-type lectin

```
hASGR1    181  YCRLEDAHLVVVTSWEEQKFVQHHIGPVNTWMGLHDQNGPWKWVDGTDYETGFKNWRPEQ  240
mAsgrl    180  YCQLENAHLVVVTSRDEQNFLQRHMGPLNTWIGLTDQNGPWKWVDGTDYETGFQNWRPEQ  239
7302 humIn 180 YCRLEDAHLVVVTSWEEQKFVQHHIGPVNTWMGLHDQNGPWKWVDGTDYETGFKNWRPEQ  239
               **  **  ******** **  *  **  ** *** ** ********************** ****
```

C-type lectin

```
hASGR1    241  PDDWYGHGLGGGEDCAHFTDDGRWNDDVCQRPYRWVCETELDKASQEPPLL  291  (SEQ ID NO: 1)
mAsgrl    240  PDNWYGHGLGGGEDCAHFTDGRWNDDVCRRPYRWVCETKLDKAN-----  284  (SEQ ID NO: 2)
7302 humIn 240 PDDWYGHGLGGGEDCAHFTDDGRWNDDVCQRPYRWVCETELDKASQEPPLL  290  (SEQ ID NO: 3)
               **  ************* **  ******** ********* ***  **
```

FIG. 3

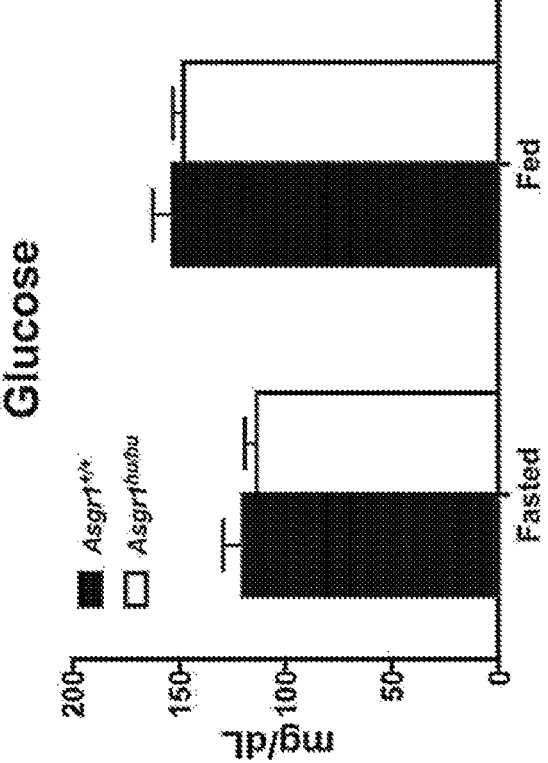
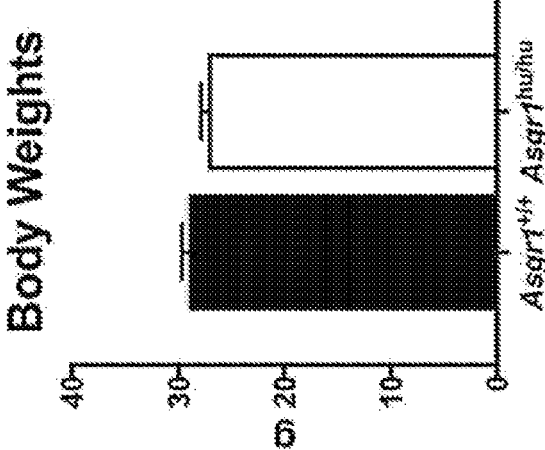
*FIG. 5*

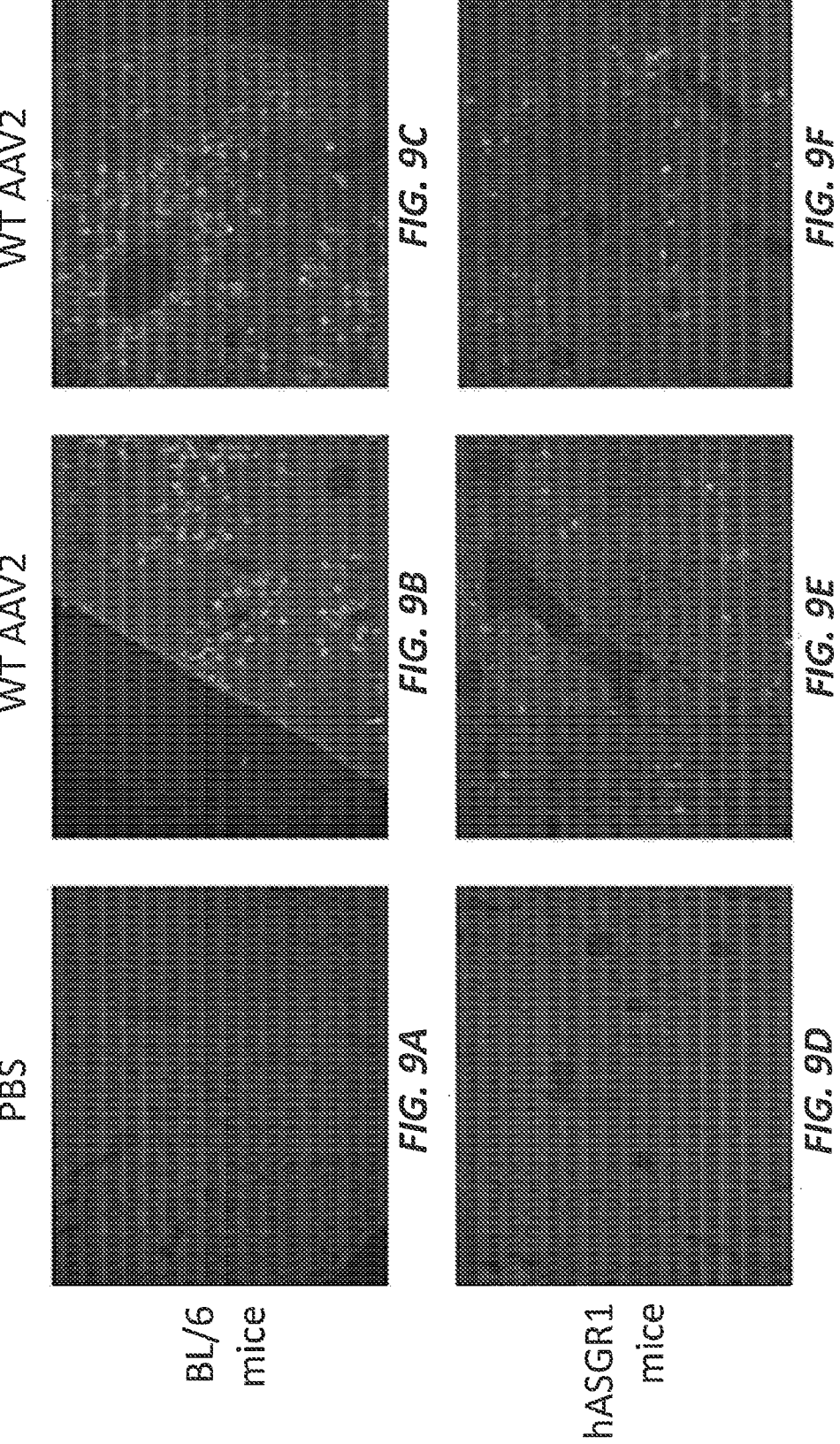

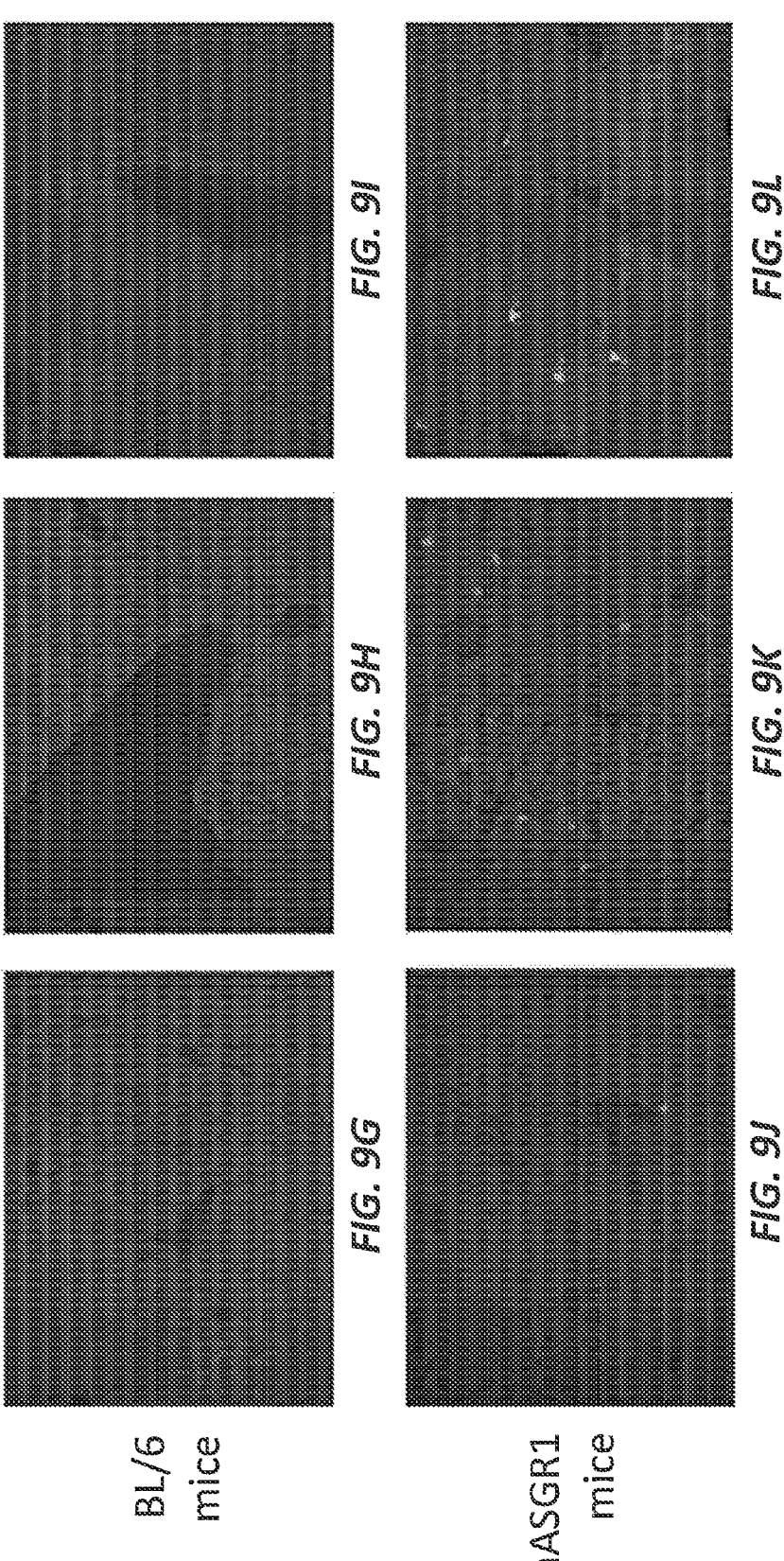

AAV2 N587Myc CAGG GFP + Myc x ASGR1 bispecific antibody

BL/6 mice hASGR1 mice

NON-HUMAN ANIMALS COMPRISING A HUMANIZED ASGR1 LOCUS

This application is a division of U.S. application Ser. No. 16/625,168, filed Dec. 20, 2019, which is a U.S. National Phase Application filed under 35 U.S.C. § 371 of PCT Application No. PCT/US2018/039864, filed Jun. 27, 2018, which claims priority to U.S. Provisional Application Ser. No. 62/525,524, filed Jun. 27, 2017, each which are incorporated herein by reference in their entireties.

REFERENCE TO A SEQUENCE LISTING SUBMITTED AS A TEXT FILE VIA EFS WEB

A Sequence Listing in xml format entitled, "10362US02_Seq-Listing_ST26," created May 19, 2023 (size 87 Kb), is incorporated herein by reference in its entirety.

BACKGROUND

Many diseases are inadequately treated due to poor targeting of therapeutic molecules to the relevant tissue or organ. Delivery of biologically active agents to subjects is often hindered by difficulties in the components reaching the target cell or tissue.

Cell-type-specific internalization effectors such as cell-type-specific receptors like human ASGR1 that are indirectly or directly internalized by a target cell can be used to facilitate and enhance delivery of therapeutic molecules to specific target cells in vivo. Similarly, such cell-type-specific internalization effectors can be appropriated for therapeutic purposes to facilitate internalization of target cell surface receptor or target soluble proteins in vivo. However, there remains a need for suitable models for assessing the efficacy of such delivery mechanisms and therapeutic mechanisms in vivo.

SUMMARY

Non-human animals comprising a humanized Asgr1 locus and expressing a humanized or chimeric ASGR1 protein from the humanized Asgr1 locus are provided, as well as methods of using such non-human animals (e.g., a rodent, e.g., a rat or a mouse), cells and/tissues derived from such non-human animals, and nucleotides (e.g., targeting vectors, genomes, etc) useful for making such animals.

In one aspect, provided are non-human animals comprising a genetically modified endogenous Asgr1 locus encoding a modified Asgr1 protein, wherein the modified Asgr1 protein comprises a cytoplasmic domain, a transmembrane domain, and an extracellular domain, and all or part of the extracellular domain is encoded by a segment of the endogenous Asgr1 locus that has been deleted and replaced with an orthologous human ASGR1 sequence. In some such non-human animals, the extracellular domain comprises a coiled-coil domain and a C-type lectin domain, and all or part of the C-type lectin domain is encoded by the segment of the endogenous Asgr1 locus that has been deleted and replaced with an orthologous human ASGR1 sequence. Optionally, the C-type lectin domain is a human ASGR1 C-type lectin domain. Optionally, the C-type lectin domain comprises the sequence set forth in SEQ ID NO: 28.

In some such animals, the extracellular domain comprises a coiled-coil domain and a C-type lectin domain, and all or part of the coiled-coil domain is encoded by the segment of the endogenous Asgr1 locus that has been deleted and replaced with an orthologous human ASGR1 sequence. Optionally, the coiled-coil domain is a human ASGR1 coiled-coil domain. Optionally, the coiled-coil domain comprises the sequence set forth in SEQ ID NO: 27.

In some such animals, all or part of both the coiled-coil domain and the C-type lectin domain are encoded by the segment of the endogenous Asgr1 locus that has been deleted and replaced with an orthologous human ASGR1 sequence. Optionally, the C-type lectin domain is a human ASGR1 C-type lectin domain, and the coiled-coil domain is a human ASGR1 coiled-coil domain. Optionally, the C-type lectin domain comprises the sequence set forth in SEQ ID NO: 28, and the coiled-coil domain comprises the sequence set forth in SEQ ID NO: 27.

In some such animals, the orthologous human ASGR1 sequence comprises exons 3-8 of a human ASGR1 gene. Optionally, the orthologous human ASGR1 sequence encodes an ASGR1 protein segment comprising the sequence set forth in SEQ ID NO: 31.

In some such animals, all or part of the cytoplasmic domain is encoded by an endogenous non-human animal Asgr1 sequence. In some such animals, all or part of the transmembrane domain is encoded by an endogenous non-human animal Asgr1 sequence. Optionally, all or part of both the cytoplasmic domain and the transmembrane domain are encoded by an endogenous non-human animal Asgr1 sequence.

In another aspect, provided are non-human animal cells or tissues (e.g., non-human hepatocytes, non-human embryonic stem (ES) cells or other pluripotent cells, such as germ cells) comprising a humanized Asgr1 locus, and in vitro compositions comprising same. In one aspect, provided are non-human animal cells comprising a genetically modified endogenous Asgr1 locus encoding a modified Asgr1 protein, wherein the modified Asgr1 protein comprises a cytoplasmic domain, a transmembrane domain, and an extracellular domain, and all or part of the extracellular domain is encoded by a segment of the endogenous Asgr1 locus that has been deleted and replaced with an orthologous human ASGR1 sequence. In some such non-human animal cells, the extracellular domain comprises a coiled-coil domain and a C-type lectin domain, and all or part of the C-type lectin domain is encoded by the segment of the endogenous Asgr1 locus that has been deleted and replaced with an orthologous human ASGR1 sequence. Optionally, the C-type lectin domain is a human ASGR1 C-type lectin domain. Optionally, the C-type lectin domain comprises the sequence set forth in SEQ ID NO: 28.

In some such non-human animal cells, the extracellular domain comprises a coiled-coil domain and a C-type lectin domain, and all or part of the coiled-coil domain is encoded by the segment of the endogenous Asgr1 locus that has been deleted and replaced with an orthologous human ASGR1 sequence. Optionally, the coiled-coil domain is a human ASGR1 coiled-coil domain. Optionally, the coiled-coil domain comprises the sequence set forth in SEQ ID NO: 27.

In some such non-human animal cells, all or part of both the coiled-coil domain and the C-type lectin domain are encoded by the segment of the endogenous Asgr1 locus that has been deleted and replaced with an orthologous human ASGR1 sequence. Optionally, the C-type lectin domain is a human ASGR1 C-type lectin domain, and the coiled-coil domain is a human ASGR1 coiled-coil domain. Optionally, the C-type lectin domain comprises the sequence set forth in SEQ ID NO: 28, and the coiled-coil domain comprises the sequence set forth in SEQ ID NO: 27.

In some such non-human animal cells, the orthologous human ASGR1 sequence comprises exons 3-8 of a human ASGR1 gene. Optionally, the orthologous human ASGR1 sequence encodes an ASGR1 protein segment comprising the sequence set forth in SEQ ID NO: 31

In some such non-human animal cells, all or part of the cytoplasmic domain is encoded by an endogenous non-human animal Asgr1 sequence. In some such animal cells, all or part of the transmembrane domain is encoded by an endogenous non-human animal Asgr1 sequence. Optionally, all or part of both the cytoplasmic domain and the transmembrane domain are encoded by an endogenous non-human animal Asgr1 sequence.

Some such animals and/or animal cells are heterozygous for the genetically modified endogenous Asgr1 locus. Some such animals and/or animal cells are homozygous for the genetically modified endogenous Asgr1 locus.

Some such non-human animals and/or animal cells are mammals and/or mammalian cells. Optionally, the mammal is a rodent. Optionally, the rodent is a rat or mouse. Optionally, the rodent is a mouse. Optionally, all or part of the cytoplasmic domain is encoded by an endogenous mouse Asgr1 sequence. Optionally, the cytoplasmic domain comprises the sequence set forth in SEQ ID NO: 29. Optionally, all or part of transmembrane domain is encoded by an endogenous mouse Asgr1 sequence. Optionally, the transmembrane domain comprises the sequence set forth in SEQ ID NO: 30. Optionally, all or part of both the cytoplasmic domain and the transmembrane domain are encoded by an endogenous mouse Asgr1 sequence. Optionally, the cytoplasmic domain comprises the sequence set forth in SEQ ID NO: 29, and the transmembrane domain comprises the sequence set forth in SEQ ID NO: 30. Optionally, the extracellular domain comprises a coiled-coil domain and a C-type lectin domain, and wherein all or part of both the coiled-coil domain and the C-type lectin domain are encoded by the segment of the endogenous Asgr1 locus that has been deleted and replaced with an orthologous human ASGR1 sequence, and all or part of both the cytoplasmic domain and the transmembrane domain are encoded by an endogenous mouse Asgr1 sequence. Optionally, the C-type lectin domain is a human ASGR1 C-type lectin domain, and the coiled-coil domain is a human ASGR1 coiled-coil domain, the cytoplasmic domain is a mouse Asgr1 cytoplasmic domain, and the transmembrane domain is a mouse Asgr1 transmembrane domain. Optionally, the C-type lectin domain comprises the sequence set forth in SEQ ID NO: 28, the coiled-coil domain comprises the sequence set forth in SEQ ID NO: 27, the cytoplasmic domain comprises the sequence set forth in SEQ ID NO: 29, and the transmembrane domain comprises the sequence set forth in SEQ ID NO: 30. Optionally, the modified Asgr1 protein comprises the sequence set forth in SEQ ID NO: 3.

In another aspect, provided are methods of assessing delivery of a therapeutic complex to the liver via human-ASGR1-mediated internalization in vivo. Some such methods comprise: (a) administering the therapeutic complex to any of the above non-human animals, wherein the therapeutic complex comprises a therapeutic molecule and an antigen-binding protein or ligand that specifically binds human ASGR1; and (b) assessing delivery of the therapeutic molecule to the liver of the non-human animal. Optionally, the therapeutic molecule is a lysosomal replacement protein or enzyme or a nucleic acid encoding the lysosomal replacement protein or enzyme, and step (b) comprises assessing the presence or activity of the lysosomal replacement protein or enzyme in the liver of the non-human animal. Optionally, the therapeutic molecule is a nucleic acid encoding the therapeutic secreted protein, and step (b) comprises assessing serum levels or activity of the therapeutic secreted protein in the non-human animal.

In another aspect, provided are methods of assessing efficacy of a therapeutic molecule targeting a liver cell surface protein or a soluble protein in the liver for internalization via human ASGR1 in vivo. Some such methods comprise: (a) administering the therapeutic molecule to any of the above non-human animals, wherein the therapeutic molecule comprises a bispecific antigen-binding protein that specifically binds the liver cell surface protein or the soluble protein and specifically binds human ASGR1; and (b) assessing cell surface levels or activity of the liver cell surface protein in the liver of the non-human animal or assessing expression or activity of the soluble protein in the liver of the non-human animal.

In another aspect, provided are nucleic acids, e.g., targeting vectors for creating a humanized Asgr1 locus as described herein, an endogenous non-human animal Asgr1 locus expressing a humanized or chimeric ASGR1 protein and/or a non-human animal genome comprising a human Asgr1 locus as described herein. Some such nucleic acids comprises a sequence selected from the group comprising of SEQ ID NO: 18, SEQ ID NO: 19, SEQ ID NO: 20, SEQ ID NO: 22, SEQ ID NO:23, and a combination thereof. Some such nucleic acids comprise a sequence that encodes an amino acid sequence set forth as SEQ ID NO: 3, e.g., comprises a sequence set forth as SEQ ID NO: 24.

BRIEF DESCRIPTION OF THE FIGURES

FIG. 3 shows an alignment of the human ASGR1 protein (hASGR1; SEQ ID NO: 1), the mouse Asgr1 protein (mAsgr1; SEQ ID NO: 2), and the humanized mouse Asgr1 protein (7302 humIn; SEQ ID NO: 3). The underscored residues are those encoded by the introduced human exons. The boxed residues constitute the transmembrane domain. The dotted line denotes the C-type lectin domain. The heavy solid line denotes the coiled-coil region.

FIG. 5 shows humanized Asgr1 mice (Asgr1$^{hu/hu}$) have similar body weights and blood glucose to their wild-type littermates.

FIGS. 9A-9R provide immunofluorescence microscopy images of liver samples taken from C57BL/6 mice transgenically modified to express human ASGR1 by liver cells (FIG. 9D-9F, 9J-9L, 9P-9R) or wildtype C57BL/6 mice (FIGS. 9A-9C, 9G-9I, 9M-9O) four weeks post intravenous injection with 2.18×10$^{11}$ wild-type ssAAV2-CAGG-eGFP (FIGS. 9B, 9C, 9E, 9F), saline (FIGS. 9A, 9D), 2.18×10$^{11}$ ssAAV2-N587myc-CAGG-eGFP viral vectors alone (FIGS. 9G-9I, 9J-9L), or ssAAV2-N587myc-CAGG-eGFP viral vectors with bispecific anti-myc-ASGR1 antibody (FIGS. 9M-9O, 9P-9R). Each image represents one mouse.

DEFINITIONS

Figures 1A, 1B:
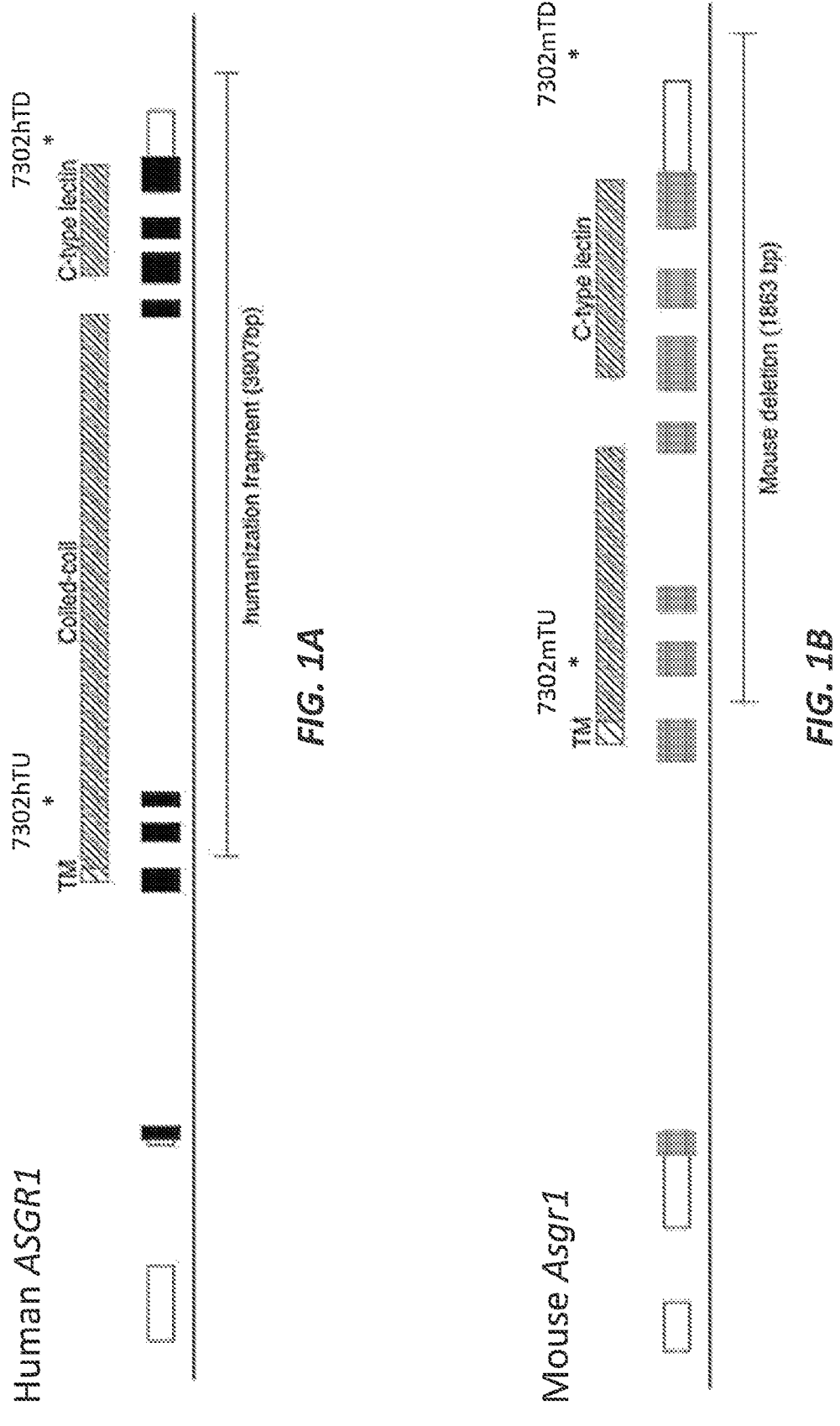
FIG. 1A shows a schematic of the human ASGR1 locus. The eight exons are indicated by the black boxes, the untranslated regions (UTRs) are indicated by the white boxes, and the transmembrane, coiled-coil, and C-type lectin domains are indicated at the top of the figure. The asterisks indicate the locations of the upstream (7302hTU) and downstream (7302hTD) primers for the gain-of-allele assay. The fragment to be inserted into the mouse Asgr1 locus for humanization is shown at the bottom.
FIG. 1B shows a schematic of the mouse Asgr1 locus. The eight exons are indicated by the black boxes, the UTRs are indicated by the white boxes, and the transmembrane, coiled-coil, and C-type lectin domains are indicated at the top of the figure. The asterisks indicate the locations of the upstream (7302mTU) and downstream (7302mTD) primers for the loss-of-allele assay. The fragment to deleted and replaced by the corresponding fragment from the human ASGR1 locus is shown at the bottom.

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones. The term "domain" refers to any part of a protein or polypeptide having a particular function or structure.

Proteins are said to have an "N-terminus" and a "C-terminus." The term "N-terminus" relates to the start of a protein or polypeptide, terminated by an amino acid with a free amine group (—NH2). The term "C-terminus" relates to the end of an amino acid chain (protein or polypeptide), terminated by a free carboxyl group (—COOH).

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

Nucleic acids are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. An end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. A nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements.

The term "genomically integrated" refers to a nucleic acid that has been introduced into a cell such that the nucleotide sequence integrates into the genome of the cell and is capable of being inherited by progeny thereof. Any protocol may be used for the stable incorporation of a nucleic acid into the genome of a cell.

The term "targeting vector" refers to a recombinant nucleic acid that can be introduced by homologous recombination, non-homologous-end-joining-mediated ligation, or any other means of recombination to a target position in the genome of a cell.

The term "viral vector" refers to a recombinant nucleic acid that includes at least one element of viral origin and includes elements sufficient for or permissive of packaging into a viral vector particle. The vector and/or particle can be utilized for the purpose of transferring DNA, RNA, or other nucleic acids into cells either ex vivo or in vivo. Numerous forms of viral vectors are known.

The term "wild type" includes entities having a structure and/or activity as found in a normal (as contrasted with mutant, diseased, altered, or so forth) state or context. Wild type genes and polypeptides often exist in multiple different forms (e.g., alleles).

The term "endogenous" refers to a nucleic acid sequence that occurs naturally within a cell or non-human animal. For example, an endogenous Asgr1 sequence of a non-human animal refers to a native Asgr1 sequence that naturally occurs at the Asgr1 locus in the non-human animal.

"Exogenous" molecules or sequences include molecules or sequences that are not normally present in a cell in that form. Normal presence includes presence with respect to the particular developmental stage and environmental conditions of the cell. An exogenous molecule or sequence, for example, can include a mutated version of a corresponding endogenous sequence within the cell, such as a humanized version of the endogenous sequence, or can include a sequence corresponding to an endogenous sequence within the cell but in a different form (i.e., not within a chromosome). In contrast, endogenous molecules or sequences include molecules or sequences that are normally present in that form in a particular cell at a particular developmental stage under particular environmental conditions.

The term "heterologous" when used in the context of a nucleic acid or a protein indicates that the nucleic acid or protein comprises at least two portions that do not naturally occur together in the same molecule. For example, the term "heterologous," when used with reference to portions of a nucleic acid or portions of a protein, indicates that the nucleic acid or protein comprises two or more sub-sequences that are not found in the same relationship to each other (e.g., joined together) in nature. As one example, a "heterologous" region of a nucleic acid vector is a segment of nucleic acid within or attached to another nucleic acid molecule that is not found in association with the other molecule in nature. For example, a heterologous region of a nucleic acid vector could include a coding sequence flanked by sequences not found in association with the coding sequence in nature. Likewise, a "heterologous" region of a protein is a segment of amino acids within or attached to another peptide molecule that is not found in association with the other peptide molecule in nature (e.g., a fusion protein, or a protein with a tag). Similarly, a nucleic acid or protein can comprise a heterologous label or a heterologous secretion or localization sequence.

"Codon optimization" takes advantage of the degeneracy of codons, as exhibited by the multiplicity of three-base pair codon combinations that specify an amino acid, and generally includes a process of modifying a nucleic acid sequence for enhanced expression in particular host cells by replacing at least one codon of the native sequence with a codon that is more frequently or most frequently used in the genes of the host cell while maintaining the native amino acid sequence. For example, a nucleic acid encoding a Cas9 protein can be modified to substitute codons having a higher frequency of usage in a given prokaryotic or eukaryotic cell, including a bacterial cell, a yeast cell, a human cell, a non-human cell, a mammalian cell, a rodent cell, a mouse cell, a rat cell, a hamster cell, or any other host cell, as compared to the naturally occurring nucleic acid sequence. Codon usage tables are readily available, for example, at the "Codon Usage Database." These tables can be adapted in a number of ways. See Nakamura et al. (2000) Nucleic Acids Research 28:292, herein incorporated by reference in its entirety for all purposes. Computer algorithms for codon optimization of a particular sequence for expression in a particular host are also available (see, e.g., Gene Forge).

The term "locus" refers to a specific location of a gene (or significant sequence), DNA sequence, polypeptide-encoding sequence, or position on a chromosome of the genome of an organism. For example, an "Asgr1 locus" may refer to the specific location of an Asgr1 gene, Asgr1 DNA sequence, Asgr1-encoding sequence, or Asgr1 position on a chromosome of the genome of an organism that has been identified as to where such a sequence resides. An "Asgr1 locus" may comprise a regulatory element of an Asgr1 gene, including, for example, an enhancer, a promoter, 5' and/or 3' untranslated region (UTR), or a combination thereof.

The term "gene" refers to a DNA sequence in a chromosome that codes for a product (e.g., an RNA product and/or a polypeptide product) and includes the coding region interrupted with non-coding introns and sequence located adjacent to the coding region on both the 5' and 3' ends such that the gene corresponds to the full-length mRNA (including the 5' and 3' untranslated sequences). The term "gene" also includes other non-coding sequences including regulatory sequences (e.g., promoters, enhancers, and transcription factor binding sites), polyadenylation signals, internal ribosome entry sites, silencers, insulating sequence, and matrix attachment regions. These sequences may be close to the coding region of the gene (e.g., within 10 kb) or at distant sites, and they influence the level or rate of transcription and translation of the gene.

The term "allele" refers to a variant form of a gene. Some genes have a variety of different forms, which are located at the same position, or genetic locus, on a chromosome. A diploid organism has two alleles at each genetic locus. Each pair of alleles represents the genotype of a specific genetic locus. Genotypes are described as homozygous if there are two identical alleles at a particular locus and as heterozygous if the two alleles differ.

A "promoter" is a regulatory region of DNA usually comprising a TATA box capable of directing RNA polymerase II to initiate RNA synthesis at the appropriate transcription initiation site for a particular polynucleotide sequence. A promoter may additionally comprise other regions which influence the transcription initiation rate. The promoter sequences disclosed herein modulate transcription of an operably linked polynucleotide. A promoter can be active in one or more of the cell types disclosed herein (e.g., a eukaryotic cell, a non-human mammalian cell, a human cell, a rodent cell, a pluripotent cell, a one-cell stage embryo, a differentiated cell, or a combination thereof). A promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter). Examples of promoters can be found, for example, in WO 2013/176772, herein incorporated by reference in its entirety for all purposes.

"Operable linkage" or being "operably linked" includes juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors. Operable linkage can include such sequences being contiguous with each other or acting in trans (e.g., a regulatory sequence can act at a distance to control transcription of the coding sequence).

The term "variant" refers to a nucleotide sequence differing from the sequence most prevalent in a population (e.g., by one nucleotide) or a protein sequence different from the sequence most prevalent in a population (e.g., by one amino acid).

The term "fragment" when referring to a protein means a protein that is shorter or has fewer amino acids than the full-length protein. The term "fragment" when referring to a nucleic acid means a nucleic acid that is shorter or has fewer nucleotides than the full-length nucleic acid. A fragment can be, for example, an N-terminal fragment (i.e., removal of a portion of the C-terminal end of the protein), a C-terminal fragment (i.e., removal of a portion of the N-terminal end of the protein), or an internal fragment.

"Sequence identity" or "identity" in the context of two polynucleotides or polypeptide sequences makes reference to the residues in the two sequences that are the same when aligned for maximum correspondence over a specified comparison window. When percentage of sequence identity is used in reference to proteins, residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

"Percentage of sequence identity" includes the value determined by comparing two optimally aligned sequences (greatest number of perfectly matched residues) over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. Unless otherwise specified (e.g., the shorter sequence includes a linked heterologous sequence), the comparison window is the full length of the shorter of the two sequences being compared.

Unless otherwise stated, sequence identity/similarity values include the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" includes any sequence comparison program that, for any two sequences in question, generates an alignment having identical nucleotide or amino acid residue matches and an identical percent sequence identity when compared to the corresponding alignment generated by GAP Version 10.

The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, or leucine for another non-polar residue. Likewise, examples of conservative substitutions include the substitution of one polar (hydrophilic) residue for another such as between arginine and lysine, between glutamine and asparagine, or between glycine and serine. Additionally, the substitution of a basic residue such as lysine, arginine, or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue. Typical amino acid categorizations are summarized below.

| Alanine | Ala | A | Nonpolar | Neutral | 1.8 |
|---|---|---|---|---|---|
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

A "homologous" sequence (e.g., nucleic acid sequence) includes a sequence that is either identical or substantially similar to a known reference sequence, such that it is, for example, at least 50%, at least 55%, at least 60%, at least 65%, at least 70%, at least 75%, at least 80%, at least 85%, at least 90%, at least 95%, at least 96%, at least 97%, at least 98%, at least 99%, or 100% identical to the known reference sequence. Homologous sequences can include, for example, orthologous sequence and paralogous sequences. Homologous genes, for example, typically descend from a common ancestral DNA sequence, either through a speciation event (orthologous genes) or a genetic duplication event (paralogous genes). "Orthologous" genes include genes in different species that evolved from a common ancestral gene by speciation. Orthologs typically retain the same function in the course of evolution. "Paralogous" genes include genes related by duplication within a genome. Paralogs can evolve new functions in the course of evolution.

The term "in vitro" includes artificial environments and to processes or reactions that occur within an artificial environment (e.g., a test tube). The term "in vivo" includes natural environments (e.g., a cell or organism or body) and to processes or reactions that occur within a natural environment. The term "ex vivo" includes cells that have been removed from the body of an individual and to processes or reactions that occur within such cells.

The term "reporter gene" refers to a nucleic acid having a sequence encoding a gene product (typically an enzyme) that is easily and quantifiably assayed when a construct comprising the reporter gene sequence operably linked to a heterologous promoter and/or enhancer element is introduced into cells containing (or which can be made to contain) the factors necessary for the activation of the promoter and/or enhancer elements. Examples of reporter genes include, but are not limited, to genes encoding beta-galactosidase (lacZ), the bacterial chloramphenicol acetyl-transferase (cat) genes, firefly luciferase genes, genes encoding beta-glucuronidase (GUS), and genes encoding fluorescent proteins. A "reporter protein" refers to a protein encoded by a reporter gene.

The term "fluorescent reporter protein" as used herein means a reporter protein that is detectable based on fluorescence wherein the fluorescence may be either from the reporter protein directly, activity of the reporter protein on a fluorogenic substrate, or a protein with affinity for binding to a fluorescent tagged compound. Examples of fluorescent proteins include green fluorescent proteins (e.g., GFP, GFP-2, tagGFP, turboGFP, eGFP, Emerald, Azami Green, Monomeric Azami Green, CopGFP, AceGFP, and ZsGreen1), yellow fluorescent proteins (e.g., YFP, eYFP, Citrine, Venus, YPet, PhiYFP, and ZsYellow1), blue fluorescent proteins (e.g., BFP, eBFP, eBFP2, Azurite, mKalamal, GFPuv, Sapphire, and T-sapphire), cyan fluorescent proteins (e.g., CFP, eCFP, Cerulean, CyPet, AmCyan1, and Midoriishi-Cyan), red fluorescent proteins (e.g., RFP, mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, and Jred), orange fluorescent proteins (e.g., mOrange, mKO, Kusabira-Orange, Monomeric Kusabira-Orange, mTangerine, and tdTomato), and any other suitable fluorescent protein whose presence in cells can be detected by flow cytometry methods.

The term "recombination" includes any process of exchange of genetic information between two polynucleotides and can occur by any mechanism. Recombination in response to double-strand breaks (DSBs) occurs principally through two conserved DNA repair pathways: non-homologous end joining (NHEJ) and homologous recombination (HR). See Kasparek & Humphrey (2011) *Seminars in Cell & Dev. Biol.* 22:886-897, herein incorporated by reference in its entirety for all purposes. Likewise, repair of a target nucleic acid mediated by an exogenous donor nucleic acid can include any process of exchange of genetic information between the two polynucleotides.

NHEJ includes the repair of double-strand breaks in a nucleic acid by direct ligation of the break ends to one another or to an exogenous sequence without the need for a homologous template. Ligation of non-contiguous sequences by NHEJ can often result in deletions, insertions, or translocations near the site of the double-strand break. For example, NHEJ can also result in the targeted integration of an exogenous donor nucleic acid through direct ligation of the break ends with the ends of the exogenous donor nucleic acid (i.e., NHEJ-based capture). Such NHEJ-mediated targeted integration can be preferred for insertion of an exogenous donor nucleic acid when homology directed repair (HDR) pathways are not readily usable (e.g., in non-dividing cells, primary cells, and cells which perform homology-based DNA repair poorly). In addition, in contrast to homology-directed repair, knowledge concerning large regions of sequence identity flanking the cleavage site is not needed, which can be beneficial when attempting targeted insertion into organisms that have genomes for which there is limited knowledge of the genomic sequence. The integration can proceed via ligation of blunt ends between the exogenous donor nucleic acid and the cleaved genomic sequence, or via ligation of sticky ends (i.e., having 5' or 3' overhangs) using an exogenous donor nucleic acid that is flanked by overhangs that are compatible with those generated by a nuclease agent in the cleaved genomic sequence. See, e.g., US 2011/020722, WO 2014/033644, WO 2014/089290, and Maresca et al. (2013) *Genome Res.* 23(3):539-546, each of which is herein incorporated by reference in its entirety for all purposes. If blunt ends are ligated, target and/or donor resection may be needed to generation regions of microhomology needed for fragment joining, which may create unwanted alterations in the target sequence.

Recombination can also occur via homology directed repair (HDR) or homologous recombination (HR). HDR or HR includes a form of nucleic acid repair that can require nucleotide sequence homology, uses a "donor" molecule as a template for repair of a "target" molecule (i.e., the one that experienced the double-strand break), and leads to transfer of genetic information from the donor to target. Without wishing to be bound by any particular theory, such transfer can involve mismatch correction of heteroduplex DNA that forms between the broken target and the donor, and/or synthesis-dependent strand annealing, in which the donor is used to resynthesize genetic information that will become part of the target, and/or related processes. In some cases, the donor polynucleotide, a portion of the donor polynucleotide, a copy of the donor polynucleotide, or a portion of a copy of the donor polynucleotide integrates into the target DNA. See Wang et al. (2013) *Cell* 153:910-918; Mandalos et al. (2012) *PLOS ONE* 7:e45768:1-9; and Wang et al. (2013) *Nat Biotechnol.* 31:530-532, each of which is herein incorporated by reference in its entirety for all purposes.

The term "antigen-binding protein" includes any protein that binds to an antigen. Examples of antigen-binding proteins include an antibody, an antigen-binding fragment of an antibody, a multi specific antibody (e.g., a bi-specific antibody), an scFV, a bis-scFV, a diabody, a triabody, a tetrabody, a V-NAR, a VHH, a VL, a F(ab), a F(ab)$_2$, a DVD (dual variable domain antigen-binding protein), an SVD (single variable domain antigen-binding protein), a bispecific T-cell engager (BiTE), or a Davisbody (U.S. Pat. No. 8,586,713, herein incorporated by reference herein in its entirety for all purposes).

The term "multi-specific" or "bi-specific" with reference to an antigen-binding protein means that the protein recognizes different epitopes, either on the same antigen or on different antigens. A multi-specific antigen-binding protein can be a single multifunctional polypeptide, or it can be a multimeric complex of two or more polypeptides that are covalently or non-covalently associated with one another. For example, an antibody or fragment thereof can be functionally linked (e.g., by chemical coupling, genetic fusion, non-covalent association or otherwise) to one or more other molecular entities, such as a protein or fragment thereof to produce a bispecific or a multi-specific antigen-binding molecule with a second binding specificity.

The term "antigen" refers to a substance, whether an entire molecule or a domain within a molecule, which is capable of eliciting production of antibodies with binding specificity to that substance. The term antigen also includes substances, which in wild type host organisms would not elicit antibody production by virtue of self-recognition, but can elicit such a response in a host animal with appropriate genetic engineering to break immunological tolerance.

The term "epitope" refers to a site on an antigen to which an antigen-binding protein (e.g., antibody) binds. An epitope can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996), herein incorporated by reference in its entirety for all purposes.

An antibody paratope as described herein generally comprises at a minimum a complementarity determining region (CDR) that specifically recognizes the heterologous epitope (e.g., a CDR3 region of a heavy and/or light chain variable domain).

The term "antibody" includes immunoglobulin molecules comprising four polypeptide chains, two heavy (H) chains and two light (L) chains inter-connected by disulfide bonds. Each heavy chain comprises a heavy chain variable domain and a heavy chain constant region ($C_H$). The heavy chain constant region comprises three domains: $C_H1$, $C_H2$ and $C_H3$. Each light chain comprises a light chain variable domain and a light chain constant region (CO. The heavy chain and light chain variable domains can be further subdivided into regions of hypervariability, termed complementarity determining regions (CDR), interspersed with regions that are more conserved, termed framework regions (FR). Each heavy and light chain variable domain comprises three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3). The term "high affinity" antibody refers to an antibody that has a $K_D$ with respect to its target epitope about of $10^{-9}$ M or lower (e.g., about $1 \times 10^{-9}$ M, $1 \times 10^{-10}$ M, $1 \times 10^{-11}$ M, or about $1 \times 10^{-12}$ M). In one embodiment, $K_D$ is measured by surface plasmon resonance, e.g., BIACORE™; in another embodiment, $K_D$ is measured by ELISA.

The term "bispecific antibody" includes an antibody capable of selectively binding two or more epitopes. Bispecific antibodies generally comprise two different heavy chains, with each heavy chain specifically binding a different epitope either on two different molecules (e.g., on two different antigens) or on the same molecule (e.g., on the same antigen). If a bispecific antibody is capable of selectively binding two different epitopes (a first epitope and a second epitope), the affinity of the first heavy chain for the first epitope will generally be at least one to two or three or four orders of magnitude lower than the affinity of the first heavy chain for the second epitope, and vice versa. The epitopes recognized by the bispecific antibody can be on the same or a different target (e.g., on the same or a different protein). Bispecific antibodies can be made, for example, by combining heavy chains that recognize different epitopes of the same antigen. For example, nucleic acid sequences encoding heavy chain variable sequences that recognize different epitopes of the same antigen can be fused to nucleic acid sequences encoding different heavy chain constant regions, and such sequences can be expressed in a cell that expresses an immunoglobulin light chain. A typical bispecific antibody has two heavy chains each having three heavy chain CDRs, followed by (N-terminal to C-terminal) a CH1 domain, a hinge, a CH2 domain, and a CH3 domain, and an immunoglobulin light chain that either does not confer antigen-binding specificity but that can associate with each heavy chain, or that can associate with each heavy chain and that can bind one or more of the epitopes bound by the heavy chain antigen-binding regions, or that can associate with each heavy chain and enable binding or one or both of the heavy chains to one or both epitopes.

The term "heavy chain," or "immunoglobulin heavy chain" includes an immunoglobulin heavy chain sequence, including immunoglobulin heavy chain constant region sequence, from any organism. Heavy chain variable domains include three heavy chain CDRs and four FR regions, unless otherwise specified. Fragments of heavy chains include CDRs, CDRs and FRs, and combinations thereof. A typical heavy chain has, following the variable domain (from N-terminal to C-terminal), a $C_H1$ domain, a hinge, a $C_H2$ domain, and a $C_H3$ domain. A functional fragment of a heavy chain includes a fragment that is capable of specifically recognizing an epitope (e.g., recognizing the epitope with a $K_D$ in the micromolar, nanomolar, or picomolar range), that is capable of expressing and secreting from a cell, and that comprises at least one CDR. Heavy chain variable domains are encoded by variable region nucleotide sequence, which generally comprises $V_H$, $D_H$, and $J_H$ segments derived from a repertoire of $V_H$, $D_H$, and $J_H$ segments present in the germline. Sequences, locations and nomenclature for V, D, and J heavy chain segments for various organisms can be found in IMGT database, which is accessible via the internet on the World Wide Web (www) at the URL "imgt.org."

The term "light chain" includes an immunoglobulin light chain sequence from any organism, and unless otherwise specified includes human kappa ($\kappa$) and lambda ($\lambda$) light chains and a VpreB, as well as surrogate light chains. Light chain variable domains typically include three light chain CDRs and four framework (FR) regions, unless otherwise specified. Generally, a full-length light chain includes, from amino terminus to carboxyl terminus, a variable domain that includes FR1-CDR1-FR2-CDR2-FR3-CDR3-FR4, and a light chain constant region amino acid sequence. Light chain variable domains are encoded by the light chain variable region nucleotide sequence, which generally comprises light chain $V_L$ and light chain $J_L$ gene segments, derived from a repertoire of light chain V and J gene segments present in the germline. Sequences, locations and nomenclature for light chain V and J gene segments for various organisms can be found in IMGT database, which is accessible via the internet on the World Wide Web (www) at the URL "imgt.org." Light chains include those, e.g., that do not selectively bind either a first or a second epitope selectively bound by the epitope-binding protein in which they appear. Light chains also include those that bind and recognize, or assist the heavy chain with binding and recognizing, one or more epitopes selectively bound by the epitope-binding protein in which they appear.

The term "complementary determining region" or "CDR," as used herein, includes an amino acid sequence encoded by a nucleic acid sequence of an organism's immunoglobulin genes that normally (i.e., in a wild type animal) appears between two framework regions in a variable region of a light or a heavy chain of an immunoglobulin molecule (e.g., an antibody or a T cell receptor). A CDR can be encoded by, for example, a germline sequence or a rearranged sequence, and, for example, by a naïve or a mature B cell or a T cell. A CDR can be somatically mutated (e.g., vary from a sequence encoded in an animal's germline), humanized, and/or modified with amino acid substitutions, additions, or deletions. In some circumstances (e.g., for a CDR3), CDRs can be encoded by two or more sequences (e.g., germline sequences) that are not contiguous (e.g., in an unrearranged nucleic acid sequence) but are contiguous in a B cell nucleic acid sequence, e.g., as a result of splicing or connecting the sequences (e.g., V-D-J recombination to form a heavy chain CDR3.

Specific binding of an antigen-binding protein to its target antigen includes binding with an affinity of at least $10^6$, $10^7$, $10^8$, $10^9$, or $10^{10}$ M$^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas non-specific binding is usually the result of van der Waals forces. Specific binding does not however necessarily imply that an antigen-binding protein binds one and only one target.

Compositions or methods "comprising" or "including" one or more recited elements may include other elements not specifically recited. For example, a composition that "comprises" or "includes" a protein may contain the protein alone or in combination with other ingredients. The transitional phrase "consisting essentially of" means that the scope of a claim is to be interpreted to encompass the specified elements recited in the claim and those that do not materially affect the basic and novel characteristic(s) of the claimed invention. Thus, the term "consisting essentially of" when used in a claim of this invention is not intended to be interpreted to be equivalent to "comprising."

"Optional" or "optionally" means that the subsequently described event or circumstance may or may not occur and that the description includes instances in which the event or circumstance occurs and instances in which it does not.

Designation of a range of values includes all integers within or defining the range, and all subranges defined by integers within the range.

Unless otherwise apparent from the context, the term "about" encompasses values within a standard margin of error of measurement (e.g., SEM) of a stated value.

The term "and/or" refers to and encompasses any and all possible combinations of one or more of the associated listed items, as well as the lack of combinations when interpreted in the alternative ("or").

The term "or" refers to any one member of a particular list and also includes any combination of members of that list.

The singular forms of the articles "a," "an," and "the" include plural references unless the context clearly dictates otherwise. For example, the term "a protein" or "at least one protein" can include a plurality of proteins, including mixtures thereof.

Statistically significant means p<0.05.

DETAILED DESCRIPTION

I. Overview

Disclosed herein are non-human animal cells and non-human animals comprising a humanized Asgr1 locus and methods of using such non-human animal cells and non-human animals. Non-human animal cells or non-human animals comprising a humanized Asgr1 locus express a human ASGR1 protein or an chimeric Asgr1 protein comprising one or more fragments of a human ASGR1 protein (e.g., all or part of the human ASGR1 extracellular domain). As a high efficiency endocytosis liver-specific receptor, human ASGR1 can be utilized for liver-specific delivery of therapeutics such as antibodies, small molecules (as a part of antibody-drug conjugates), and DNA. However, antigen-binding proteins or bispecific antigen-binding proteins that specifically bind human ASGR1 often will not bind to orthologous non-human animal Asgr1 proteins such as mouse Asgr1 due to the sequence differences between human ASGR1 and the non-human animal Asgr1. For example, antibodies generated against the human ASGR1 extracellular domain do not bind to the mouse Asgr1 ortholog (data not shown). Because of this, in vivo efficacy of human-ASGR1-mediated delivery mechanisms or therapeutic mechanisms cannot be effectively assessed in wild type non-human animals with unmodified endogenous (i.e., native) Asgr1 loci. Humanized Asgr1 non-human animals (e.g., humanized Asgr1 mice) can be used for validation of liver-specific delivery of different therapeutics via human-ASGR1-mediated internalization utilizing a number of different approaches. For example, non-human animals comprising the humanized Asgr1 locus can be used to assess in vivo efficacy of human-ASGR1-mediated delivery of therapeutic molecules or therapeutic complexes to the liver. Similarly, non-human animals comprising the humanized Asgr1 locus can be used to assess the efficacy of therapeutic molecules or therapeutic complexes acting via human-ASGR1-mediated mechanisms.

II. Non-Human Animals Comprising a Humanized Asgr1 Locus

The cells and non-human animals disclosed herein comprise a humanized Asgr1 locus. Cells or non-human animals comprising a humanized Asgr1 locus express a human ASGR1 protein or a partially humanized, chimeric Asgr1 protein in which one or more fragments of the native Asgr1 protein have been replaced with corresponding fragments from human ASGR1 (e.g., all or part of the extracellular domain).

A. Asialoglycoprotein Receptor 1 (ASGR1)

The cells and non-human animals described herein comprise a humanized Asgr1 locus. Asialoglycoprotein receptor 1 (C-type lectin domain family 4 member H1, hepatic lectin H1, HL-1, ASGP-R 1, ASGPR 1, ASGR1) is encoded by the ASGR1 (CLEC4H1) gene and is the major subunit of asialoglycoprotein receptor (ASGPR or ASGR). ASGPR is a heterooligomeric protein expressed mainly on the cell surface of hepatocytes, with approximately $1\text{-}5\times10^5$ binding sites/cell and a role in internalization and degradation of desialylated glycoproteins to remove them from circulation. ASGPR is a well-characterized C-type hepatic lectin, primarily expressed on the sinusoidal surface of hepatocytes. ASGPR is responsible for the selective binding and internalization of galactose-terminating and N-acetylgalactosamine-terminating glycoproteins by hepatic parenchymal cells via receptor-mediated endocytosis. It comprises two proteins, asialoglycoprotein receptor 1 and 2 (ASGR1 and ASGR2), encoded by the genes ASGR1 and ASGR2. Both subunits are type II, single pass proteins that broadly comprise an N-terminal cytoplasmic domain, a single transmembrane domain, and a C-terminal extracellular carbohydrate recognition domain (CRD). ASGR1 contains an N-terminal cytoplasmic domain (~40 amino acids), a single-pass transmembrane domain (~20 amino acids), an extracellular coiled-coil stalk (oligomerization) region (~80 amino acids), and a functional C-type (calcium-dependent) carbohydrate recognition domain (C-type lectin domains) (~140 amino acids). The CRD binds to glycoproteins with terminal galactose or N-acetylgalactosamine (GalNac) motifs. The CRD has low affinity for desialylated glycoproteins in the monomeric state.

The genes encoding ASGR1 and ASGR2 (ASGR1 and ASGR2, respectively) are located on the short arm of chromosome 17, approximately 58.6 kilobases (kb) apart. The genes are evolutionarily related but differ significantly in their structural organization: ASGR1 comprises 8 exons and is approximately 6 kb long, and ASGR2 contains 9 exons and is approximately 13.5 kb long.

An exemplary coding sequence for human ASGR1 is assigned NCBI Accession Number NM_001671 (SEQ ID NO: 5). An exemplary coding sequence for mouse Asgr1 is assigned NCBI Accession Number NM_009714 (SEQ ID NO: 4). An exemplary human ASGR1 protein is assigned UniProt Accession No. P07306 (SEQ ID NO: 1). An exemplary mouse Asgr1 protein is assigned UniProt Accession No. P34927 (SEQ ID NO: 2). An exemplary mouse Asgr1 protein with humanized coiled-coil and C-type lectin domains is set forth in SEQ ID NO: 3. An exemplary rat Asgr1 protein is assigned UniProt Accession No.: P02706. An exemplary orangutan Asgr1 protein is assigned UniProt Accession No. Q5RBQ8.

B. Humanized Asgr1 Loci

A humanized Asgr1 locus can be an Asgr1 locus in which the entire Asgr1 gene is replaced with the corresponding orthologous human ASGR1 sequence, or it can be an Asgr1 locus in which only a portion of the Asgr1 gene is replaced with the corresponding orthologous human ASGR1 sequence (i.e., humanized). Optionally, the corresponding orthologous human ASGR1 sequence is modified to be codon-optimized based on codon usage in the non-human animal. Replaced (i.e., humanized) regions can include coding regions such as an exon, non-coding regions such as an intron, an untranslated region, or a regulatory region (e.g., a promoter, an enhancer, or a transcriptional repressor-binding element), or any combination thereof. As one example, exons corresponding to 1, 2, 3, 4, 5, 6, 7, or all 8 exons of the human ASGR1 gene can be humanized. For example, exons corresponding to exons 3-8 of the human ASGR1 gene can be humanized. Alternatively, a region of Asgr1 encoding an epitope recognized by an anti-human-ASGR1 antigen-binding protein can be humanized. As another example, one or more or all of the N-terminal cytoplasmic domain, the transmembrane domain, the coiled-coil domain, or the C-type lectin domain can be humanized. For example, all or part of the region of the Asgr1 locus encoding the coiled-coil domain can be humanized, all or part of the region of the Asgr1 locus encoding the C-type lectin domain can be humanized, all or part of the region of the Asgr1 locus encoding the transmembrane domain can be humanized, and/or all or part of the region of the Asgr1 locus encoding the cytoplasmic domain can be humanized. In one example, only all or part of the region of the Asgr1 locus encoding the coiled-coil domain is humanized, only all or part of the region of the Asgr1 locus encoding the C-type lectin domain is humanized, or only all or part of the region of the Asgr1 locus encoding the extracellular region (i.e., the coiled-coil domain and the C-type lectin domain). For example, the regions of the Asgr1 locus encoding the coiled-coil domain and the C-type lectin domain can be humanized such that a chimeric Asgr1 protein is produce with an endogenous N-terminal cytoplasmic domain, an endogenous transmembrane domain, a humanized coiled-coil domain, and a humanized C-type lectin domain. Likewise, introns corresponding to 1, 2, 3, 4, 5, 6, or all 7 introns of the human ASGR1 gene can be humanized. Flanking untranslated regions including regulatory sequences can also be humanized. For example, the 5' untranslated region (UTR), the 3'UTR, or both the 5' UTR and the 3' UTR can be humanized, or the 5' UTR, the 3'UTR, or both the 5' UTR and the 3' UTR can remain endogenous. In one specific example, the 3' UTR is humanized, but the 5' UTR remains endogenous. Depending on the extent of replacement by orthologous sequences, regulatory sequences, such as a promoter, can be endogenous or supplied by the replacing human orthologous sequence. For example, the humanized Asgr1 locus can include the endogenous non-human animal Asgr1 promoter.

The Asgr1 protein encoded by the humanized Asgr1 locus can comprise one or more domains that are from a human ASGR1 protein. For example, the Asgr1 protein can comprise one or more or all of a human ASGR1 coiled-coil domain, a human ASGR1 C-type lectin domain, a human ASGR1 transmembrane domain, and a human ASGR1 cytoplasmic domain. As one example, the Asgr1 protein can comprise only a human ASGR1 coiled-coil domain, only a human ASGR1 C-type lectin domain, or only a human ASGR1 extracellular domain (i.e., coiled-coil domain and C-type lectin domain). Optionally, the Asgr1 protein encoded by the humanized Asgr1 locus can also comprise one or more domains that are from the endogenous (i.e., native) non-human animal Asgr1 protein. As one example, the Asgr1 protein encoded by the humanized Asgr1 locus can comprise a coiled-coil domain from a human ASGR1 protein, a C-type lectin domain from a human ASGR1 protein, an N-terminal cytoplasmic domain from the endogenous (i.e., native) non-human animal Asgr1 protein, and a transmembrane domain from the endogenous (i.e., native) non-human animal Asgr1 protein. Domains from a human ASGR1 protein can be encoded by a fully humanized sequence (i.e., the entire sequence encoding that domain is replaced with the orthologous human ASGR1 sequence) or can be encoded by a partially humanized sequence (i.e., some of the sequence encoding that domain is replaced with the orthologous human ASGR1 sequence, and the remaining endogenous (i.e., native) sequence encoding that domain encodes the same amino acids as the orthologous human ASGR1 sequence such that the encoded domain is identical to that domain in the human ASGR1 protein).

As one example, the Asgr1 protein encoded by the humanized Asgr1 locus can comprise a human ASGR1 coiled-coil domain. Optionally, the human ASGR1 coiled-coil domain comprises, consists essentially of, or consists of a sequence that is at least 85%, 90%, 95%, 96%, 97%, 98%, 99%, or 100% identical to SEQ ID NO: 27 and the Asgr1 protein retains the activity of the native Asgr1 (i.e., retains the ability to selectively bind and internalize galactose-terminating and N-acetylgalactosamine-terminating glyco-proteins via receptor-mediated endocytosis). As another example, the Asgr1 protein encoded by the humanized Asgr1 locus can comprise a human ASGR1 C-type lectin domain. Optionally, the human ASGR1 C-type lectin domain comprises, consists essentially of, or consists of a sequence that is at least 85%, 90%, 95%, 96%, 97%, 98%, 99%, or 100% identical to SEQ ID NO: 28 and the Asgr1 protein retains the activity of the native Asgr1. For example, the region of the Asgr1 protein that is from human ASGR1 can comprise, consist essentially of, or consist of a sequence that is at least 85%, 90%, 95%, 96%, 97%, 98%, 99%, or 100% identical to SEQ ID NO: 31 and the Asgr1 protein retains the activity of the native Asgr1. As another example, the Asgr1 protein encoded by the humanized Asgr1 locus can comprise an endogenous non-human animal Asgr1 cytoplasmic domain (e.g., a mouse Asgr1 cytoplasmic domain). Optionally, the non-human animal Asgr1 cytoplasmic domain comprises, consists essentially of, or consists of a sequence that is at least 85%, 90%, 95%, 96%, 97%, 98%, 99%, or 100% identical to SEQ ID NO: 29 and the Asgr1 protein retains the activity of the native Asgr1. As another example, the Asgr1 protein encoded by the humanized Asgr1 locus can comprise an endogenous non-human animal Asgr1 transmembrane domain (e.g., a mouse Asgr1 trans-membrane domain). Optionally, the non-human animal Asgr1 transmembrane domain comprises, consists essentially of, or consists of a sequence that is at least 85%, 90%, 95%, 96%, 97%, 98%, 99%, or 100% identical to SEQ ID NO: 30 and the Asgr1 protein retains the activity of the native Asgr1. For example, the Asgr1 protein encoded by the humanized Asgr1 locus can comprise, consist essentially of, or consist of a sequence that is at least 85%, 90%, 95%, 96%, 97%, 98%, 99%, or 100% identical to SEQ ID NO: 3 and the Asgr1 protein retains the activity of the native Asgr1.

Optionally, a humanized Asgr1 locus can comprise other elements. Examples of such elements can include selection cassettes, reporter genes, recombinase recognition sites, or other elements. Alternatively, the humanized Asgr1 locus can lack other elements (e.g., can lack a selection marker or selection cassette). Examples of suitable reporter genes and reporter proteins are disclosed elsewhere herein. Examples of suitable selection markers include neomycin phospho-transferase (neo$_r$), hygromycin B phosphotransferase (hyg$_r$), puromycin-N-acetyltransferase (puro$_r$), blasticidin S deaminase (bsr$_r$), xanthine/guanine phosphoribosyl transferase (gpt), and herpes simplex virus thymidine kinase (HSV-k). Examples of recombinases include Cre, Flp, and Dre recombinases. One example of a Cre recombinase gene is Crei, in which two exons encoding the Cre recombinase are separated by an intron to prevent its expression in a prokaryotic cell. Such recombinases can further comprise a nuclear localization signal to facilitate localization to the nucleus (e.g., NLS-Crei). Recombinase recognition sites include nucleotide sequences that are recognized by a site-specific recombinase and can serve as a substrate for a recombination event. Examples of recombinase recognition sites include FRT, FRT11, FRT71, attp, att, rox, and lox sites such as loxP, lox511, lox2272, lox66, lox71, loxM2, and lox5171.

Other elements such as reporter genes or selection cassettes can be self-deleting cassettes flanked by recombinase recognition sites. See, e.g., U.S. Pat. No. 8,697,851 and US 2013/0312129, each of which is herein incorporated by reference in its entirety for all purposes. As an example, the self-deleting cassette can comprise a Crei gene (comprises two exons encoding a Cre recombinase, which are separated by an intron) operably linked to a mouse Prm1 promoter and a neomycin resistance gene operably linked to a human ubiquitin promoter. By employing the Prm1 promoter, the self-deleting cassette can be deleted specifically in male germ cells of F0 animals. The polynucleotide encoding the selection marker can be operably linked to a promoter active in a cell being targeted. Examples of promoters are described elsewhere herein. As another specific example, a self-deleting selection cassette can comprise a hygromycin resistance gene coding sequence operably linked to one or more promoters (e.g., both human ubiquitin and EM7 promoters) followed by a polyadenylation signal, followed by a Crei coding sequence operably linked to one or more promoters (e.g., an mPrm1 promoter), followed by another polyadenylation signal, wherein the entire cassette is flanked by loxP sites.

The humanized Asgr1 locus can also be a conditional allele. For example, the conditional allele can be a multi-functional allele, as described in US 2011/0104799, herein incorporated by reference in its entirety for all purposes. For example, the conditional allele can comprise: (a) an actuating sequence in sense orientation with respect to transcription of a target gene; (b) a drug selection cassette (DSC) in sense or antisense orientation; (c) a nucleotide sequence of interest (NSI) in antisense orientation; and (d) a conditional by inversion module (COIN, which utilizes an exon-splitting intron and an invertible gene-trap-like module) in reverse orientation. See, e.g., US 2011/0104799. The conditional allele can further comprise recombinable units that recombine upon exposure to a first recombinase to form a conditional allele that (i) lacks the actuating sequence and the DSC; and (ii) contains the NSI in sense orientation and the COIN in antisense orientation. See, e.g., US 2011/0104799.

One exemplary humanized Asgr1 locus (e.g., a humanized mouse Asgr1 locus) is one in which coding exons 3-8 are replaced with the corresponding human sequence. These exons encode the coiled-coil and C-type lectin domains of Asgr1. Optionally, the humanized sequence can be through the stop codon and 3' UTR, and optionally into the sequence just downstream of the 3' UTR. Optionally, a portion of the intron upstream of coding exon 3 is also humanized. See FIGS. 2A and 2B and SEQ ID NOS: 21 and 24.

C. Non-Human Cells and Non-Human Animals Comprising a Humanized Asgr1 Locus

Non-human animal cells and non-human animals comprising a humanized Asgr1 locus as described elsewhere herein are provided. The cells or non-human animals can be heterozygous or homozygous for the humanized Asgr1 locus. A diploid organism has two alleles at each genetic locus. Each pair of alleles represents the genotype of a specific genetic locus. Genotypes are described as homozygous if there are two identical alleles at a particular locus and as heterozygous if the two alleles differ.

The non-human animal cells provided herein can be, for example, any non-human cell comprising an Asgr1 locus or a genomic locus homologous or orthologous to the human ASGR1 locus. The cells can be eukaryotic cells, which include, for example, fungal cells (e.g., yeast), plant cells, animal cells, mammalian cells, non-human mammalian cells, and human cells. The term "animal" includes mammals, fishes, and birds. A mammalian cell can be, for example, a non-human mammalian cell, a rodent cell, a rat cell, a mouse cell, or a hamster cell. Other non-human mammals include, for example, non-human primates, monkeys, apes, orangutans, cats, dogs, rabbits, horses, bulls, deer, bison, livestock (e.g., bovine species such as cows, steer, and so forth; ovine species such as sheep, goats, and so forth; and porcine species such as pigs and boars). Birds include, for example, chickens, turkeys, ostrich, geese, ducks, and so forth. Domesticated animals and agricultural animals are also included. The term "non-human" excludes humans.

The cells can also be any type of undifferentiated or differentiated state. For example, a cell can be a totipotent cell, a pluripotent cell (e.g., a human pluripotent cell or a non-human pluripotent cell such as a mouse embryonic stem (ES) cell or a rat ES cell), or a non-pluripotent cell. Totipotent cells include undifferentiated cells that can give rise to any cell type, and pluripotent cells include undifferentiated cells that possess the ability to develop into more than one differentiated cell types. Such pluripotent and/or totipotent cells can be, for example, ES cells or ES-like cells, such as an induced pluripotent stem (iPS) cells. ES cells include embryo-derived totipotent or pluripotent cells that are capable of contributing to any tissue of the developing embryo upon introduction into an embryo. ES cells can be derived from the inner cell mass of a blastocyst and are capable of differentiating into cells of any of the three vertebrate germ layers (endoderm, ectoderm, and mesoderm).

The cells provided herein can also be germ cells (e.g., sperm or oocytes). The cells can be mitotically competent cells or mitotically-inactive cells, meiotically competent cells or meiotically-inactive cells. Similarly, the cells can also be primary somatic cells or cells that are not a primary somatic cell. Somatic cells include any cell that is not a gamete, germ cell, gametocyte, or undifferentiated stem cell. For example, the cells can be liver cells, such as hepatoblasts or hepatocytes.

Suitable cells provided herein also include primary cells. Primary cells include cells or cultures of cells that have been isolated directly from an organism, organ, or tissue. Primary cells include cells that are neither transformed nor immortal. They include any cell obtained from an organism, organ, or tissue which was not previously passed in tissue culture or has been previously passed in tissue culture but is incapable of being indefinitely passed in tissue culture. Such cells can be isolated by conventional techniques and include, for example, hepatocytes.

Other suitable cells provided herein include immortalized cells. Immortalized cells include cells from a multicellular organism that would normally not proliferate indefinitely but, due to mutation or alteration, have evaded normal cellular senescence and instead can keep undergoing division. Such mutations or alterations can occur naturally or be intentionally induced. A specific example of an immortalized cell line is the HepG2 human liver cancer cell line. Numerous types of immortalized cells are well known. Immortalized or primary cells include cells that are typically used for culturing or for expressing recombinant genes or proteins.

The cells provided herein also include one-cell stage embryos (i.e., fertilized oocytes or zygotes). Such one-cell stage embryos can be from any genetic background (e.g., BALB/c, C57BL/6, 129, or a combination thereof for mice), can be fresh or frozen, and can be derived from natural breeding or in vitro fertilization.

The cells provided herein can be normal, healthy cells, or can be diseased or mutant-bearing cells.

Non-human animals comprising a humanized Asgr1 locus as described herein can be made by the methods described elsewhere herein. The term "animal" includes mammals, fishes, and birds. Non-human mammals include, for example, non-human primates, monkeys, apes, orangutans, cats, dogs, horses, bulls, deer, bison, sheep, rabbits, rodents (e.g., mice, rats, hamsters, and guinea pigs), and livestock (e.g., bovine species such as cows and steer; ovine species such as sheep and goats; and porcine species such as pigs and boars). Birds include, for example, chickens, turkeys, ostrich, geese, and ducks. Domesticated animals and agricultural animals are also included. The term "non-human animal" excludes humans. Preferred non-human animals include, for example, rodents, such as mice and rats.

The non-human animals can be from any genetic background. For example, suitable mice can be from a 129 strain, a C57BL/6 strain, a mix of 129 and C57BL/6, a BALB/c strain, or a Swiss Webster strain. Examples of 129 strains include 129P1, 129P2, 129P3, 129X1, 129S1 (e.g., 129S1/SV, 129S1/Svlm), 129S2, 129S4, 129S5, 129S9/SvEvH, 129S6 (129/SvEvTac), 129S7, 129S8, 129T1, and 129T2. See, e.g., Festing et al. (1999) *Mammalian Genome* 10:836, herein incorporated by reference in its entirety for all purposes. Examples of C57BL strains include C57BL/A, C57BL/An, C57BL/GrFa, C57BL/Kal_wN, C57BL/6, C57BL/6J, C57BL/6ByJ, C57BL/6NJ, C57BL/10, C57BL/10ScSn, C57BL/10Cr, and C57BL/Ola. Suitable mice can also be from a mix of an aforementioned 129 strain and an aforementioned C57BL/6 strain (e.g., 50% 129 and 50% C57BL/6). Likewise, suitable mice can be from a mix of aforementioned 129 strains or a mix of aforementioned BL/6 strains (e.g., the 129S6 (129/SvEvTac) strain).

Similarly, rats can be from any rat strain, including, for example, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. Rats can also be obtained from a strain derived from a mix of two or more strains recited above. For example, a suitable rat can be from a DA strain or an ACI strain. The ACI rat strain is characterized as having black agouti, with white belly and feet and an $RT1^{av1}$ haplotype. Such strains are available from a variety of sources including Harlan Laboratories. The Dark Agouti (DA) rat strain is characterized as having an agouti coat and an $RT1^{av1}$ haplotype. Such rats are available from a variety of sources including Charles River and Harlan Laboratories. Some suitable rats can be from an inbred rat strain. See, e.g., US 2014/0235933, herein incorporated by reference in its entirety for all purposes.

III. Methods of Using Non-Human Animals Comprising a Humanized Asgr1 Locus for Assessing In Vivo Efficacy of Human-ASGR1-Mediated Delivery of Therapeutic Complexes to the Liver and Therapeutic Molecules Acting Via Human-ASGR1-Mediated Mechanisms Various methods are provided for using the non-human animals comprising a humanized Asgr1 locus as described elsewhere herein for assessing the in vivo efficacy of human-ASGR1-mediated delivery of therapeutic molecules or complexes to the liver or of human-ASGR1-mediated therapeutic mechanisms. Because the non-human animals comprise a humanized Asgr1 locus, the non-human animals will more accurately reflect delivery mediated by human ASGR1 or human-ASGR1-mediated therapeutic mechanisms than non-human animals with a non-humanized Asgr1 locus. As one example, the methods can assess delivery of a therapeutic complex to the liver via human-ASGR1-mediated internalization in vivo, comprising administering the therapeutic complex to a non-human animal comprising a humanized Asgr1 locus, wherein the therapeutic complex comprises a therapeutic molecule and an antigen-binding protein or ligand that specifically binds human ASGR1, and then assessing delivery of the therapeutic molecule to the liver of the non-human animal. As another example, the methods can the in vivo efficacy of therapeutic molecules or complexes designed to act via human-ASGR1-mediated internalization, such as therapeutic complexes designed to internalize a target liver cell surface protein via human ASGR1.

A. Methods of Assessing In Vivo Efficacy of Delivery of Therapeutic Molecules to the Liver Via Human-ASGR1-Mediated Internalization Various methods are provided for using the non-human animals comprising a humanized Asgr1 locus as described elsewhere herein for assessing the in vivo efficacy of delivery of therapeutic molecules to the liver via human-ASGR1-mediated internalization. For example, such methods can comprise: (a) administering a therapeutic complex to the non-human animal comprising a humanized Asgr1 locus, wherein the therapeutic complex comprises a therapeutic molecule and an antigen-binding protein or ligand that specifically binds human ASGR1; and (b) assessing delivery of the therapeutic molecule to the liver of the non-human animal.

The therapeutic molecule can be any biological or chemical agent used in the treatment or prophylaxis of any disease or disorder. For example, the therapeutic molecule can be therapeutic nucleic acids (e.g., CRISPR/Cas guide RNAs, short hairpin RNAs (shRNAs), or small interfering RNAs (siRNAs)) or nucleic acids encoding therapeutic proteins (e.g., Cas proteins such as Cas9 proteins, replacement enzymes, secreted therapeutic proteins, and so forth). Alternatively, the therapeutic molecule can be a therapeutic protein, a therapeutic antibody or antigen-binding protein, or any other therapeutic large molecule or small molecule.

The therapeutic molecule and the human ASGR1 antigen-binding protein or ligand can be complexed together by any means. For example, the therapeutic molecule and the human ASGR1 antigen-binding protein or ligand can be coupled through direct covalent conjugation or can be coupled through a linker, such as a peptide linker or a chemical linker. The therapeutic molecule and the human ASGR1 antigen-binding protein or ligand can also be complexed together through formation of bonds between particular functional groups or particular spatial fit (e.g., lock and key type). As a specific example, the human ASGR1 antigen-binding protein can be a bispecific antigen-binding protein that also specifically binds the therapeutic molecule.

The administering of the therapeutic complex can be by any means as disclosed in more detail elsewhere herein and by any route of administration. Means of delivering therapeutic complexes and molecules and routes of administration are disclosed in more detail elsewhere herein.

Human ASGR1 antigen-binding proteins or human ASGR1 ligands that specifically bind human ASGR1 can be used. Because human ASGR1 protein is a transmembrane protein that mediates the endocytosis of certain glycoproteins in the liver, molecules that become complexed with human ASGR1 can be internalized together with human ASGR1. Examples of suitable antigen-binding proteins include a receptor-fusion molecule, a trap molecule, a receptor-Fc fusion molecule, an antibody, an Fab fragment, an F(ab')2 fragment, an Fd fragment, an Fv fragment, a single-chain Fv (scFv) molecule, a dAb fragment, an isolated complementarity determining region (CDR), a CDR3 peptide, a constrained FR3-CDR3-FR4 peptide, a domain-specific antibody, a single domain antibody, a domain-deleted antibody, a chimeric antibody, a CDR-grafted antibody, a diabody, a triabody, a tetrabody, a minibody, a nanobody, a monovalent nanobody, a bivalent nanobody, a small modular immunopharmaceutical (SMIP), a camelid antibody (VHH heavy chain homodimeric antibody), a shark variable IgNAR domain, and the like. In one particular example, the antigen-binding protein is a bispecific antibody which binds to human ASGR1 and to the therapeutic molecule (e.g., a replacement protein or enzyme or a delivery vehicle such as AAV). Alternatively, a ligand or portion of a ligand that specifically interacts with human ASGR1 (e.g., asialoorosomucoid (ASOR) or Beta-GalNAc or a receptor-binding portion thereof for ASGR1) can be used.

Delivery of the therapeutic molecule to the liver of the non-human animal can be assessed by any known means. As one example, the presence of the therapeutic molecule can be assessed in the liver. For example, if the therapeutic molecule is a therapeutic protein, presence of the therapeutic protein can be assessed in the liver of the non-human animal using known assays for detecting proteins. Similarly, if the therapeutic molecule is a nucleic acid encoding a therapeutic protein, expression of the nucleic acid (e.g., mRNA expression or protein expression) can be assessed in the liver of the non-human animal using known assays. If the encoded therapeutic protein is a secreted protein, serum levels of the therapeutic protein can be measured, or activity of the secreted therapeutic protein at its intended target cell type, tissue type, or organ can be assessed by known assays. Activity of the therapeutic molecule in the liver of the non-human animal can be assessed by known assays depending on the intended function of the therapeutic molecule. For example, if a genome editing agent such as CRISPR/Cas is being introduced, known assays can be used to assess genome editing at a particular target genomic locus.

In a specific example, the therapeutic complex can comprise viral vector compositions (e.g., liver-specific viral vector compositions). Such viral vector compositions can have reduced or abolished natural tropism that are designed to be directed to human ASGR1 for targeting the liver. For example, such a modified viral vector complex can comprise: (i) a modified viral vector comprising a nucleic acid encoding the therapeutic nucleic acid or protein, wherein the modified viral vector has abolished or reduced natural tropism and comprises a heterologous epitope; and (ii) a retargeting moiety comprising: (1) an antigen-binding protein (e.g., antibody) paratope that specifically binds the heterologous epitope; and (2) a targeting ligand that specifically binds human ASGR1.

As one example of how to accomplish this, a protein tagging system such as SpyCatcher-SpyTag can be used to covalently couple antibodies to the virus surface. Alternatively, bispecific antigen-binding proteins can be used (e.g., bispecific antibodies in which one arm of the antibody binds the virus and the other arm mediates binding to human ASGR1). In a specific example, the redirecting moiety is a bispecific antigen-binding protein (e.g., bispecific antibody) comprising a first and second antigen-binding domains, wherein the first antigen-binding domain comprises a paratope that specifically binds the heterologous epitope inserted into/displayed by a recombinant human viral capsid protein, and the second antigen-binding domain specifically binds human ASGR1.

An example of a suitable heterologous epitope is a Myc tag. For example, the Myc tag can be inserted after N587 of AAV2. Such an insertion abolishes the natural ligand-binding activity of AAV2 and also allows recognition of the modified AAV by anti-Myc antibody. Use of a bispecific antibody that specifically binds to both Myc and to human ASGR1 can then retarget the AAV (e.g., AAV2 N587 Myc) to liver cells expressing human ASGR1 (or humanized Asgr1).

In another example, the therapeutic complex comprises a lysosomal replacement enzyme or protein or a nucleic acid encoding a lysosomal replacement enzyme or protein. Lysosomal storage diseases are a class of rare diseases that affect the degradation of different substrates in the lysosome, including sphingolipids, mucopolysaccharides, glycoproteins, glycogen, and oligosaccharides, which can accumulate in the diseased cells, leading to cell death. Organs affected by lysosomal storage diseases include the liver. The pathogeneses of the diseases are ascribed to the buildup of incomplete degradation products in the lysosome, usually due to loss of protein function. Lysosomal storage diseases are generally caused by loss-of-function or attenuating variants in the proteins whose normal function is to degrade or coordinate degradation of lysosomal contents. Examples of lysosomal storage diseases are provided in WO 2017/100467, herein incorporated by reference in its entirety for all purposes. For example, one of the most common lysosomal storage diseases is Pompe disease. Pompe disease is caused by defective lysosomal enzyme alpha-glucosidase (GAA), which results in the deficient processing of lysosomal glycogen. Accumulation of lysosomal glycogen occurs predominantly in skeletal, cardiac, and hepatic tissues.

One option for treatment of lysosomal storage diseases is enzyme or protein replacement therapy. Replacement enzymes or proteins can be effectively delivered to the lysosome of a specific target cell when associated in a therapeutic complex with an antigen-binding protein or a ligand that specifically binds human ASGR1. See WO 2017/100467, herein incorporated by reference in its entirety for all purposes. Such a therapeutic complex can be administered to a subject, and the therapeutic complex can enter the lysosome of a targeted cell of the subject and provide an enzyme activity that replaces the enzymatic activity that is associated with the lysosomal storage disease. The human ASGR1 protein is a transmembrane protein that mediates the endocytosis and lysosomal degradation of glycoproteins with exposed terminal galactose or N-acetylgalactosamine residues in the liver. Consequently, proteins that bind to and are internalized together with human ASGR1 will be targeted to the lysosome. As such, delivery methods that direct therapeutic molecules or complexes to human ASGR1 can be used to target the therapeutics to lysosomes (e.g., lysosomes in the liver).

Accordingly, some of the methods provided herein are methods of assessing delivery of a therapeutic complex comprising a lysosomal replacement protein or enzyme to the liver via human ASGR1 in vivo. For example, such methods can comprise (a) administering a therapeutic molecule or therapeutic complex to the non-human animals described elsewhere herein, wherein the therapeutic molecule or the therapeutic complex comprises a lysosomal replacement protein or enzyme (or a nucleic acid encoding a lysosomal replacement protein or enzyme) and an antigen-binding protein that specifically binds human ASGR1, wherein ASGR1 mediates cell binding and uptake into a lysosome compartment; and (b) assessing the presence or activity of the lysosomal replacement protein or enzyme in the liver of the non-human animal. Activity of the replacement protein or enzyme in the liver of the non-human animal can be assessed by known assays for the particular replacement protein or enzyme or by measuring degradation of different affected substrates in the lysosome by known assays.

As another example, the therapeutic molecule can be a nucleic acid encoding a therapeutic secreted protein. The liver plays a major role in producing proteins that are secreted into the blood, including major plasma proteins, factors in hemostasis and fibrinolysis, carrier proteins, hormones, prohormones, and apolipoproteins. The human ASGR1 protein is a transmembrane protein that mediates the endocytosis of certain glycoproteins in the liver. Consequently, molecules that become complexed with human ASGR1 can be internalized together with human ASGR1. As such, a nucleic acid encoding a therapeutic secreted protein can be targeted to the liver by delivering it in a complex that targets human ASGR1. The nucleic acid can be internalized via ASGR1, and the liver can manufacture and secrete the therapeutic protein.

Accordingly, some of the methods provided herein are methods of assessing delivery of a nucleic acid encoding a therapeutic secreted protein to the liver via human ASGR1 in vivo. For example, such methods can comprise (a) administering a nucleic acid (e.g., DNA) encoding a therapeutic secreted protein to a non-human animal described elsewhere herein, wherein the nucleic acid is delivered in a therapeutic complex that specifically binds to human ASGR1, and ASGR1 mediates internalization of the complex; and (b) assessing the secreted levels (e.g., serum levels) or activity of the therapeutic secreted protein in the non-human animal.

Production and secretion of the therapeutic protein can be assessed by any known means. For example, expression of the introduced nucleic acid can be assessed by measuring levels of the encoded mRNA in the liver of the non-human animal or levels of the encoded therapeutic protein in the liver of the non-human animal using known assays. Secretion of the therapeutic protein can be assessed by measuring or serum levels of the encoded therapeutic protein in the non-human animal using known assays. In addition, if the secreted therapeutic protein acts on a particular cell type, tissue, or organ, activity of the secreted therapeutic protein can be assessed in the target cell type, tissue, or organ.

B. Methods of Assessing In Vivo Efficacy of a Therapeutic Complex for Internalizing a Target Liver Cell Surface Protein or a Target Soluble Protein in the Liver Via Human-ASGR1-Mediated Internalization Various methods are provided for using the non-human animals comprising a humanized Asgr1 locus as described elsewhere herein for assessing the in vivo efficacy of a therapeutic complex designed to internalize a target liver cell surface protein or a target soluble protein in the liver via human ASGR1. Therapeutic treatments often require the inactivation or blocking of one or more target molecules that act on or in the vicinity of a cell. For example, antibody-based therapeutics often function by binding to a particular antigen expressed on the surface of a cell, or to a soluble ligand, thereby interfering with the antigen's normal biological activity. Therapeutic agents of this type typically function by blocking the interaction between a cytokine and its receptor in order to attenuate or inhibit cellular signaling. In certain contexts, however, it would be therapeutically beneficial to inactivate or inhibit the activity of a target molecule in a manner that does not necessarily involve blocking its physical interaction with another component. One way in which such non-blocking attenuation of a target molecule could be achieved would be to reduce the extra-cellular or cell surface concentration of the target molecule. For example, a target molecule could be attenuated or inactivated by facilitating or bringing about a physical linkage between the target molecule and an internalizing effector protein such as ASGR1. This can be achieved, for example, through use of a multi specific (e.g., bispecific) antigen-binding molecule comprising a first antigen-binding domain and a second antigen-binding domain. Each antigen-binding domain binds a different molecule: the first specifically binds a target molecule, and the second specifically binds ASGR1. Through this type of physical intermolecular linkage, the target molecule can be forced to be internalized into the cell along with the ASGR1, and processed by the intracellular degradative machinery, or otherwise attenuated, sequestered, or inactivated. See WO 2013/138400 and US 2013/0243775, each of which herein incorporated by reference in its entirety for all purposes.

Because the human ASGR1 protein is a transmembrane protein that mediates the endocytosis and lysosomal degradation of glycoproteins with exposed terminal galactose or N-acetylgalactosamine residues in the liver, cell surface proteins that that become complexed with human ASGR1 can be internalized together with human ASGR1, re-routing the target cell surface protein or target soluble protein to a degradative compartment or sequestering the target cell surface protein or target soluble protein in internal compartments or exosomes.

Accordingly, provided herein are methods for using the non-human animals comprising a humanized Asgr1 locus as described elsewhere herein for assessing the in vivo efficacy of a therapeutic complex designed to internalize a target liver cell surface protein or a target soluble protein in the liver via human ASGR1. For example, such methods can comprise (a) administering the therapeutic complex to the non-human animals described elsewhere herein, wherein the therapeutic complex comprises a bispecific antigen-binding protein that specifically binds to the target cell surface protein or target soluble protein and specifically binds to human ASGR1, wherein ASGR1 mediates internalization of the target cell surface protein or target soluble protein; and (b) assessing the cell surface levels or activity of the target liver cell surface protein or assessing expression levels or activity of the target soluble protein in the liver of the non-human animal. The administering of the therapeutic complex can be by any suitable means, as described elsewhere herein.

Target cell surface proteins can include any cell surface protein expressed in the liver. Target soluble proteins can include any soluble protein expressed in the liver. The cell surface levels or activity of the target liver cell surface protein in the liver of the non-human animal can be assessed by known assays for measuring cell surface levels of receptors and other proteins. Likewise, levels of soluble proteins can be assessed by known assays.

C. Administering Molecules to Non-Human Animals

The methods disclosed herein comprise introducing into non-human animal one various molecules (therapeutic molecules or complexes), including nucleic acids, proteins, or protein complexes. The introducing can be accomplished by any means. For example, such molecules can be introduced into a non-human animal, for example, by vector delivery, particle-mediated delivery, exosome-mediated delivery, lipid-nanoparticle-mediated delivery, cell-penetrating-peptide-mediated delivery, or implantable-device-mediated delivery. As specific examples, a molecule can be introduced into a cell or non-human animal in a carrier such as a poly(lactic acid) (PLA) microsphere, a poly(D,L-lactic-co-glycolic-acid) (PLGA) microsphere, a liposome, a micelle, an inverse micelle, a lipid cochleate, or a lipid microtubule. Some specific examples of delivery to a non-human animal include hydrodynamic delivery, virus-mediated delivery (e.g., adeno-associated virus (AAV)-mediated delivery), and lipid-nanoparticle-mediated delivery.

Introduction of nucleic acids, proteins, or other components into non-human animals can be accomplished by hydrodynamic delivery (HDD). Hydrodynamic delivery has emerged as a perfect method for intracellular DNA delivery in vivo. For gene delivery to parenchymal cells, only essential DNA sequences need to be injected via a selected blood vessel, eliminating safety concerns associated with current viral and synthetic vectors. When injected into the bloodstream, DNA is capable of reaching cells in the different tissues accessible to the blood. Hydrodynamic delivery employs the force generated by the rapid injection of a large volume of solution into the incompressible blood in the circulation to overcome the physical barriers of endothelium and cell membranes that prevent large and membrane-impermeable compounds from entering parenchymal cells. In addition to the delivery of DNA, this method is useful for the efficient intracellular delivery of RNA, proteins, and other small compounds in vivo. See, e.g., Bonamassa et al. (2011) *Pharm. Res.* 28(4):694-701, herein incorporated by reference in its entirety for all purposes.

Introduction of nucleic acids can also be accomplished by virus-mediated delivery, such as AAV-mediated delivery or lentivirus-mediated delivery. Other exemplary viruses/viral vectors include retroviruses, adenoviruses, vaccinia viruses, poxviruses, and herpes simplex viruses. The viruses can infect dividing cells, non-dividing cells, or both dividing and non-dividing cells. The viruses can integrate into the host genome or alternatively do not integrate into the host genome. Such viruses can also be engineered to have reduced immunity. The viruses can be replication-competent or can be replication-defective (e.g., defective in one or more genes necessary for additional rounds of virion replication and/or packaging). Viruses can cause transient expression, long-lasting expression (e.g., at least 1 week, 2 weeks, 1 month, 2 months, or 3 months), or permanent expression (e.g., of Cas9 and/or gRNA). Exemplary viral titers (e.g., AAV titers) include $10^{12}$, $10^{13}$, $10^{14}$, $10^{15}$, and $10^{16}$ vector genomes/mL.

The ssDNA AAV genome consists of two open reading frames, Rep and Cap, flanked by two inverted terminal repeats that allow for synthesis of the complementary DNA strand. When constructing an AAV transfer plasmid, the transgene is placed between the two ITRs, and Rep and Cap can be supplied in trans. In addition to Rep and Cap, AAV can require a helper plasmid containing genes from adenovirus. These genes (E4, E2a, and VA) mediated AAV replication. For example, the transfer plasmid, Rep/Cap, and the helper plasmid can be transfected into HEK293 cells containing the adenovirus gene E1+ to produce infectious AAV particles. Alternatively, the Rep, Cap, and adenovirus helper genes may be combined into a single plasmid. Similar packaging cells and methods can be used for other viruses, such as retroviruses.

Multiple serotypes of AAV have been identified. These serotypes differ in the types of cells they infect (i.e., their tropism), allowing preferential transduction of specific cell types. Serotypes for liver tissue include AAV7, AAV8, and AAV9, and particularly AAV8.

Tropism can be further refined through pseudotyping, which is the mixing of a capsid and a genome from different viral serotypes. Use of pseudotyped viruses can improve transduction efficiency, as well as alter tropism. Hybrid capsids derived from different serotypes can also be used to alter viral tropism. For example, AAV-DJ contains a hybrid capsid from eight serotypes and displays high infectivity across a broad range of cell types in vivo. AAV serotypes can also be modified through mutations. Other pseudotyped/modified AAV variants include AAV2/1, AAV2/6, AAV2/7, AAV2/8, AAV2/9, AAV2.5, AAV8.2, and AAV/SASTG.

To accelerate transgene expression, self-complementary AAV (scAAV) variants can be used. Because AAV depends on the cell's DNA replication machinery to synthesize the complementary strand of the AAV's single-stranded DNA genome, transgene expression may be delayed. To address this delay, scAAV containing complementary sequences that are capable of spontaneously annealing upon infection can be used, eliminating the requirement for host cell DNA synthesis.

To increase packaging capacity, longer transgenes may be split between two AAV transfer plasmids, the first with a 3' splice donor and the second with a 5' splice acceptor. Upon co-infection of a cell, these viruses form concatemers, are spliced together, and the full-length transgene can be expressed. Although this allows for longer transgene expression, expression is less efficient. Similar methods for increasing capacity utilize homologous recombination. For example, a transgene can be divided between two transfer plasmids but with substantial sequence overlap such that co-expression induces homologous recombination and expression of the full-length transgene.

Introduction of nucleic acids and proteins can also be accomplished by lipid nanoparticle (LNP)-mediated delivery. For example, LNP-mediated delivery can be used to deliver a guide RNA in the form of RNA. Delivery through such methods results in transient presence of the guide RNA, and the biodegradable lipids improve clearance, improve tolerability, and decrease immunogenicity. Lipid formulations can protect biological molecules from degradation while improving their cellular uptake. Lipid nanoparticles are particles comprising a plurality of lipid molecules physically associated with each other by intermolecular forces. These include microspheres (including unilamellar and multilamellar vesicles, e.g., liposomes), a dispersed phase in an emulsion, micelles, or an internal phase in a suspension. Such lipid nanoparticles can be used to encapsulate one or more nucleic acids or proteins for delivery. Formulations which contain cationic lipids are useful for delivering polyanions such as nucleic acids. Other lipids that can be included are neutral lipids (i.e., uncharged or zwitterionic lipids), anionic lipids, helper lipids that enhance transfection, and stealth lipids that increase the length of time for which nanoparticles can exist in vivo. Examples of suitable cationic lipids, neutral lipids, anionic lipids, helper lipids, and stealth lipids can be found in WO 2016/010840 A1, herein incorporated by reference in its entirety for all purposes. An exemplary lipid nanoparticle can comprise a cationic lipid and one or more other components. In one example, the other component can comprise a helper lipid such as cholesterol. In another example, the other components can comprise a helper lipid such as cholesterol and a neutral lipid such as DSPC. In another example, the other components can comprise a helper lipid such as cholesterol, an optional neutral lipid such as DSPC, and a stealth lipid such as S010, S024, S027, S031, or S033.

The mode of delivery can be selected to decrease immunogenicity. Different modes may confer different pharmacodynamics or pharmacokinetic properties on the subject delivered molecule. For example, the different modes can result in different tissue distribution, different half-life, or different temporal distribution. Some modes of delivery (e.g., delivery of a nucleic acid vector that persists in a cell by autonomous replication or genomic integration) result in more persistent expression and presence of the molecule, whereas other modes of delivery are transient and less persistent (e.g., delivery of an RNA or a protein). Delivery of components in a more transient manner, for example as RNA or protein, can ensure that the components are only present and active for a short period of time and can reduce immunogenicity.

Administration in vivo can be by any suitable route including, for example, parenteral, intravenous, subcutaneous, intra-arterial, or intraperitoneal. Systemic modes of administration include, for example, parenteral routes, such as intravenous, intraarterial, subcutaneous, and intraperitoneal routes. A specific example is intravenous infusion. Local modes of administration can also be used.

Compositions comprising the nucleic acids or proteins can be formulated using one or more physiologically and pharmaceutically acceptable carriers, diluents, excipients or auxiliaries. The formulation can depend on the route of administration chosen. The term "pharmaceutically acceptable" means that the carrier, diluent, excipient, or auxiliary is compatible with the other ingredients of the formulation and not substantially deleterious to the recipient thereof.

The frequency of administration and the number of dosages can be depend on the half-life of the components introduced and the route of administration among other factors. The introduction of nucleic acids or proteins into the non-human animal can be performed one time or multiple times over a period of time. For example, the introduction can be performed at least two times over a period of time, at least three times over a period of time, at least four times over a period of time, at least five times over a period of time, at least six times over a period of time, at least seven times over a period of time, at least eight times over a period of time, at least nine times over a period of times, at least ten times over a period of time, at least eleven times, at least twelve times over a period of time, at least thirteen times over a period of time, at least fourteen times over a period of time, at least fifteen times over a period of time, at least sixteen times over a period of time, at least seventeen times over a period of time, at least eighteen times over a period of time, at least nineteen times over a period of time, or at least twenty times over a period of time.

IV. Methods of Making Non-Human Animals Comprising a Humanized Asgr1 Locus

Various methods are provided for making a non-human animal comprising a humanized Asgr1 locus as disclosed elsewhere herein. Any convenient method or protocol for producing a genetically modified organism is suitable for producing such a genetically modified non-human animal. See, e.g., Cho et al. (2009) *Current Protocols in Cell Biology* 42:19.11:19.11.1-19.11.22 and Gama Sosa et al. (2010) *Brain Struct. Funct.* 214(2-3):91-109, each of which is herein incorporated by reference in its entirety for all purposes. Such genetically modified non-human animals can be generated, for example, through gene knock-in at a targeted Asgr1 locus.

For example, the method of producing a non-human animal comprising a humanized Asgr1 locus can comprise: (1) modifying the genome of a pluripotent cell to comprise the humanized Asgr1 locus; (2) identifying or selecting the genetically modified pluripotent cell comprising the humanized Asgr1 locus; (3) introducing the genetically modified pluripotent cell into a non-human animal host embryo; and (4) implanting and gestating the host embryo in a surrogate mother. Optionally, the host embryo comprising modified pluripotent cell (e.g., a non-human ES cell) can be incubated until the blastocyst stage before being implanted into and gestated in the surrogate mother to produce an F0 non-human animal. The surrogate mother can then produce an F0 generation non-human animal comprising the humanized Asgr1 locus.

The methods can further comprise identifying a cell or animal having a modified target genomic locus. Various methods can be used to identify cells and animals having a targeted genetic modification.

The screening step can comprise, for example, a quantitative assay for assessing modification of allele (MOA) of a parental chromosome. For example, the quantitative assay can be carried out via a quantitative PCR, such as a real-time PCR (qPCR). The real-time PCR can utilize a first primer set that recognizes the target locus and a second primer set that recognizes a non-targeted reference locus. The primer set can comprise a fluorescent probe that recognizes the amplified sequence.

Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology (see, e.g., US 2005/0144655, incorporated herein by reference in its entirety for all purposes).

An example of a suitable pluripotent cell is an embryonic stem (ES) cell (e.g., a mouse ES cell or a rat ES cell). The modified pluripotent cell can be generated, for example, through recombination by (a) introducing into the cell one or more targeting vectors comprising an insert nucleic acid flanked by 5' and 3' homology arms corresponding to 5' and 3' target sites, wherein the insert nucleic acid comprises a humanized Asgr1 locus; and (b) identifying at least one cell comprising in its genome the insert nucleic acid integrated at the target genomic locus. Alternatively, the modified pluripotent cell can be generated by (a) introducing into the cell: (i) a nuclease agent, wherein the nuclease agent induces a nick or double-strand break at a recognition site within the target genomic locus; and (ii) one or more targeting vectors comprising an insert nucleic acid flanked by 5' and 3' homology arms corresponding to 5' and 3' target sites located in sufficient proximity to the recognition site, wherein the insert nucleic acid comprises the humanized Asgr1 locus; and (c) identifying at least one cell comprising a modification (e.g., integration of the insert nucleic acid) at the target genomic locus. Any nuclease agent that induces a nick or double-strand break into a desired recognition site can be used. Examples of suitable nucleases include a Transcription Activator-Like Effector Nuclease (TALEN), a zinc-finger nuclease (ZFN), a meganuclease, and Clustered Regularly Interspersed Short Palindromic Repeats (CRISPR)/CRISPR-associated (Cas) systems or components of such systems (e.g., CRISPR/Cas9). See, e.g., US 2013/0309670 and US 2015/0159175, each of which is herein incorporated by reference in its entirety for all purposes.

The donor cell can be introduced into a host embryo at any stage, such as the blastocyst stage or the pre-morula stage (i.e., the 4 cell stage or the 8 cell stage). Progeny that are capable of transmitting the genetic modification though the germline are generated. See, e.g., U.S. Pat. No. 7,294,754, herein incorporated by reference in its entirety for all purposes.

Alternatively, the method of producing the non-human animals described elsewhere herein can comprise: (1) modifying the genome of a one-cell stage embryo to comprise the humanized Asgr1 locus using the methods described above for modifying pluripotent cells; (2) selecting the genetically modified embryo; and (3) implanting and gestating the genetically modified embryo into a surrogate mother. Progeny that are capable of transmitting the genetic modification though the germline are generated.

Nuclear transfer techniques can also be used to generate the non-human mammalian animals. Briefly, methods for nuclear transfer can include the steps of: (1) enucleating an oocyte or providing an enucleated oocyte; (2) isolating or providing a donor cell or nucleus to be combined with the enucleated oocyte; (3) inserting the cell or nucleus into the enucleated oocyte to form a reconstituted cell; (4) implanting the reconstituted cell into the womb of an animal to form an embryo; and (5) allowing the embryo to develop. In such methods, oocytes are generally retrieved from deceased animals, although they may be isolated also from either oviducts and/or ovaries of live animals. Oocytes can be matured in a variety of well-known media prior to enucleation. Enucleation of the oocyte can be performed in a number of well-known manners. Insertion of the donor cell or nucleus into the enucleated oocyte to form a reconstituted cell can be by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell can be activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, can be cultured in well-known media and then transferred to the womb of an animal. See, e.g., US 2008/0092249, WO 1999/005266, US 2004/0177390, WO 2008/017234, and U.S. Pat. No. 7,612,250, each of which is herein incorporated by reference in its entirety for all purposes.

The various methods provided herein allow for the generation of a genetically modified non-human F0 animal wherein the cells of the genetically modified F0 animal comprise the humanized Asgr1 locus. It is recognized that depending on the method used to generate the F0 animal, the number of cells within the F0 animal that have the humanized Asgr1 locus will vary. The introduction of the donor ES cells into a pre-morula stage embryo from a corresponding organism (e.g., an 8-cell stage mouse embryo) via for example, the VELOCIMOUSE® method allows for a greater percentage of the cell population of the F0 animal to comprise cells having the nucleotide sequence of interest comprising the targeted genetic modification. For example, at least 50%, 60%, 65%, 70%, 75%, 85%, 86%, 87%, 87%, 88%, 89%, 90%, 91%, 92%, 93%, 94%, 95%, 96%, 97%, 98%, 99% or 100% of the cellular contribution of the non-human F0 animal can comprise a cell population having the targeted modification.

The cells of the genetically modified F0 animal can be heterozygous for the humanized Asgr1 locus or can be homozygous for the humanized Asgr1 locus.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, web site or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

BRIEF DESCRIPTION OF THE SEQUENCES

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

TABLE 1

Description of Sequences.

| SEQ ID NO | Type | Description |
|---|---|---|
| 1 | Protein | hASGR1 - P07306 |
| 2 | Protein | mAsgr1 - P34927 |
| 3 | Protein | 7302 Humanized Asgr1 |
| 4 | DNA | mAsgr1 Coding Sequence - NM_009714 (Nucleotides 154-1008) |
| 5 | DNA | hASGR1 Coding Sequence - NM_001671 (Nucleotides 401-1276) |
| 6 | DNA | 7302mTU Fwd |
| 7 | DNA | 7302mTU Probe (BHQ) |
| 8 | DNA | 7302mTU Rev |
| 9 | DNA | 7302mTD Fwd |
| 10 | DNA | 7302mTD Probe (BHQ) |
| 11 | DNA | 7302mTD Rev |
| 12 | DNA | 7302hTU Fwd |
| 13 | DNA | 7302hTU Probe (BHQ) |
| 14 | DNA | 7302hTU Rev |
| 15 | DNA | 7302hTD Fwd |
| 16 | DNA | 7302hTD Probe (BHQ) |
| 17 | DNA | 7302hTD Rev |
| 18 | DNA | 7302 Border A |
| 19 | DNA | 7302 Border B |
| 20 | DNA | 7302 Border C |
| 21 | DNA | 7302 Allele |
| 22 | DNA | 7303 Border A |
| 23 | DNA | 7303 Border D |
| 24 | DNA | 7303 Allele |
| 25 | Protein | c-Myc Epitope |
| 26 | DNA | c-Myc Epitope |
| 27 | Protein | hASGR1 Coiled-Coil Domain |
| 28 | Protein | hASGR1 C-Type Lectin Domain |
| 29 | Protein | mASGR1 Cytoplasmic Domain |
| 30 | Protein | mASGR1 Transmembrane Domain |
| 31 | Protein | ASGR1 Segment Encoded by Humanized Region of Asgr1 |
| 32 | DNA | PAAVRCBsiWF Primer |
| 33 | DNA | N587mycR Primer |
| 34 | DNA | N587mycF Primer |
| 35 | DNA | PAAVRCPmeR Primer |
| 36 | DNA | AAV2 ITR-F Primer |
| 37 | DNA | AAV2 ITR-R Primer |
| 38 | DNA | AAV2 ITR Probe |
| 39 | Protein | Macaca Asgr1 - XP_005582755.1 |
| 40 | DNA | Macaca Asgr1 Coding Sequence - XM_005582698.2 (Nucleotides 310-1185) |
| 41 | Protein | Rat Asgr1- NP_036635.1 |
| 42 | DNA | Rat Asgr1 Coding Sequence - NM_012503.2 (Nucleotides 66-920) |

EXAMPLES

Example 1. Generation of Mice Comprising a Humanized Asgr1 Locus

Asialoglycoprotein Receptor (Ashwell Receptor, ASGR) is a predominantly hepatic membrane bound carbohydrate binding protein receptor (~33 kDa) belonging to the C-type class of lectin receptors. ASGR binds to glycoproteins with terminal galactose or N-acetylgalactosamine (GalNac) motifs. It can remove desialylated glycoproteins from circulation by receptor mediated endocytosis. The ligand undergoes lysosomal degradation, while ASGR is recycled back to the cell surface. The receptor is a heterooligomer of two subunits, ASGR1 and ASGR2 (H1 and H2). As a high efficiency endocytosis liver-specific receptor, ASGR1 can be utilized for liver-specific delivery of therapeutics such as antibodies, small molecules (as a part of antibody-drug conjugates), and DNA. However, antibodies and bispecific antibodies that we have generated against the human ASGR1 extracellular domain do not bind to the mouse Asgr1 ortholog (Biacore data not shown). Thus, we generated humanized Asgr1 mice for use in validation of liver-specific delivery of different therapeutics utilizing a number of different approaches.

A large targeting vector comprising a 5' homology arm comprising 24 kb from bMQ-69B11 and 3' homology arm comprising 67 kb from bMQ-69B11 was generated to replace coding exons 3-8 (through the stop codon and 3' UTR, into the sequence just downstream of the 3' UTR) of mouse Asgr1 with the corresponding human sequence of ASGR1. The encoded Asgr1 protein will have a mouse Asgr1 transmembrane domain followed by human coiled-coil and C-type lectin domains. See FIGS. 2A and 3. To generate the mutant allele, CRISPR/Cas9 components were introduced into F1H4 mouse embryonic stem cells together with the large targeting vector. Loss-of-allele assays using the primers and probes set forth in Table 2 were performed to detect loss of the endogenous mouse allele, and gain-of-allele assays using the primers and probes set forth in Table 3 were performed to detect gain of the humanized allele. Loss-of-allele and gain-of-allele assays are described, for example, in US 2014/0178879; US 2016/0145646; WO 2016/081923; and Frendewey et al. (2010) *Methods Enzymol.* 476:295-307, each of which is herein incorporated by reference in its entirety for all purposes.

TABLE 2

Mouse TAQMAN® Loss-of-Allele Assays

| LOA Assay | Primer/ Probe | Sequence |
|---|---|---|
| 7302mTU | Fwd | TCCCAACTCCGGGAAGATC (SEQ ID NO: 6) |
| | Probe (BHQ) | TGCTGGCTCTAAGGCAGAA TTTCA (SEQ ID NO: 7) |
| | Rev | TCAGTGCTCACAGTGAGGTT (SEQ ID NO: 8) |
| 7302mTD | Fwd | GGGTTGGCTCATGTTAGGAA GG (SEQ ID NO: 9) |
| | Probe (BHQ) | TCAGCAGCCGAGCTGTGAAA (SEQ ID NO: 10) |
| | Rev | CAGGCTGTGCTACCCAAAGT TC (SEQ ID NO: 11) |

TABLE 3

Human TAQMAN® Gain-of-Allele Assays

| GOA Assay | Primer/ Probe | Sequence |
|---|---|---|
| 7302hTU | Fwd | GGAGGCAATGTGGGAAGAAAG (SEQ ID NO: 12) |
| | Probe (BHQ) | TGAAGTCGCTAGAGTCCCA GCTGG (SEQ ID NO: 13) |
| | Rev | TCAGGTCCTTCTGCTGTTTC (SEQ ID NO: 14) |
| 7302hTD | Fwd | GATTGGGAATCCGCCCATCT (SEQ ID NO: 15) |

TABLE 3-continued

Human TAQMAN® Gain-of-Allele Assays

| GOA Assay | Primer/ Probe | Sequence |
|---|---|---|
| | Probe (BHQ) | CCTCTTCTGCTTTCTCGGGA ATTTTCATC (SEQ ID NO: 16) |
| | Rev | AAAGCGCCACGGGTTTCAAG (SEQ ID NO: 17) |

Figures 2A, 2B:
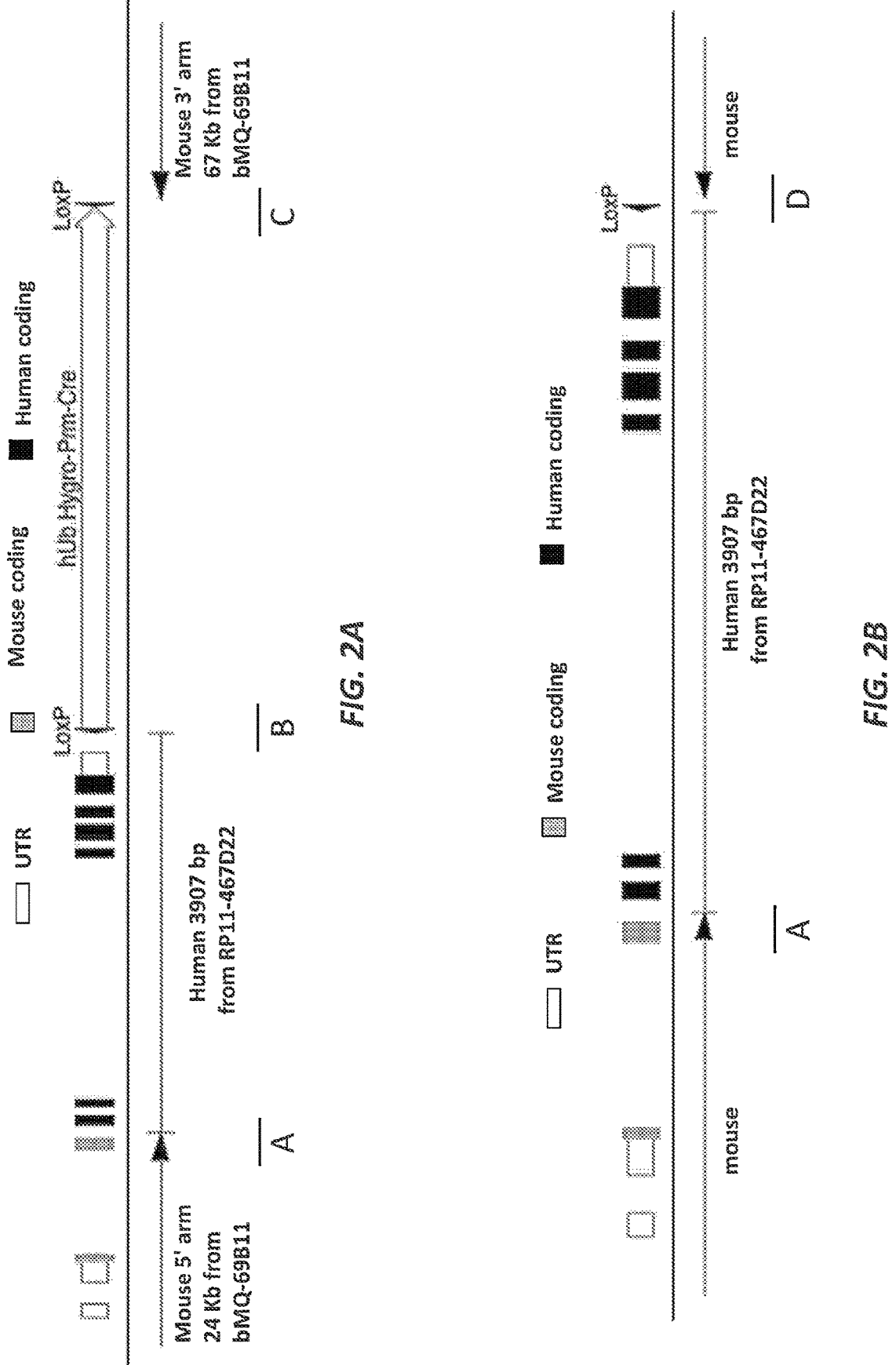
FIG. 2A shows a schematic of the large targeting vector for generating a humanized Asgr1 allele (7302 allele) containing a hygromycin resistance self-deleting cassette. The mouse exons are indicated by the gray boxes, the human exons are indicated by the black boxes, and the UTRs are indicated by the white boxes. The boundaries between the different regions (mouse/human, human/cassette, and cassette/mouse) are indicated by the lines labeled A, B, and C, respectively, at the bottom of the figure.
FIG. 2B shows a schematic of a cassette-deleted version of the humanized Asgr1 allele in FIG. 2A. The mouse exons are indicated by the gray boxes, the human exons are indicated by the black boxes, and the UTRs are indicated by the white boxes. The boundaries between the different regions (5' mouse/human boundary, 3' human/mouse boundary) are indicated by the lines labeled A and D, respectively, at the bottom of the figure.

F0 mice were then generated using the VELOCI-MOUSE® method. See, e.g., U.S. Pat. Nos. 7,576,259; 7,659,442; 7,294,754; US 2008/007800; and Poueymirou et al. (2007) *Nature Biotech.* 25(1):91-99, each of which is herein incorporated by reference in its entirety for all purposes. A portion of the intron upstream of coding exon 3 was also humanized. In all, 1863 bp of mouse Asgr1 sequence was replaced by 3907 bp of human ASGR1 sequence. A loxP-hUb1-em7-hygromycin resistance gene-polyadenylation signal-mPrm1-Crei-polyadenylation signal-loxP cassette (5218 bp) was also inserted downstream of the human 3' UTR, with a buffer of approximately 190 bp of 3' human sequence of the 3' UTR just before the cassette. The resulting partially humanized mouse Asgr1 allele with the hygromycin resistance self-deleting cassette is set forth in SEQ ID NO: 21 (referred to as the 7302 allele). The sequence border regions A, B, and C in FIG. 2A are set forth in SEQ ID NOS: 18, 19, and 20, respectively. A comparison of the human ASGR1 protein (SEQ ID NO: 1), the mouse Asgr1 protein (SEQ ID NO: 2), and the partially humanized mouse Asgr1 protein (SEQ ID NO: 3) are shown in FIG. 3.

Upon removal of the self-deleting cassette with Cre recombinase, the loxP and cloning sites (77 bp) remain downstream of the human 3' UTR, with a buffer of approximately 190 bp of 3' human sequence after the 3' UTR just before the remaining loxP. See FIG. 2B. The resulting partially humanized mouse, cassette-deleted Asgr1 allele is set forth in SEQ ID NO: 24 (referred to as the 7303 allele). The sequence border regions A and C in FIG. 2B are set forth in SEQ ID NOS: 22 and 23, respectively.

Example 2. Validation of Mice Comprising a Humanized Asgr1 Locus

Figure 4:
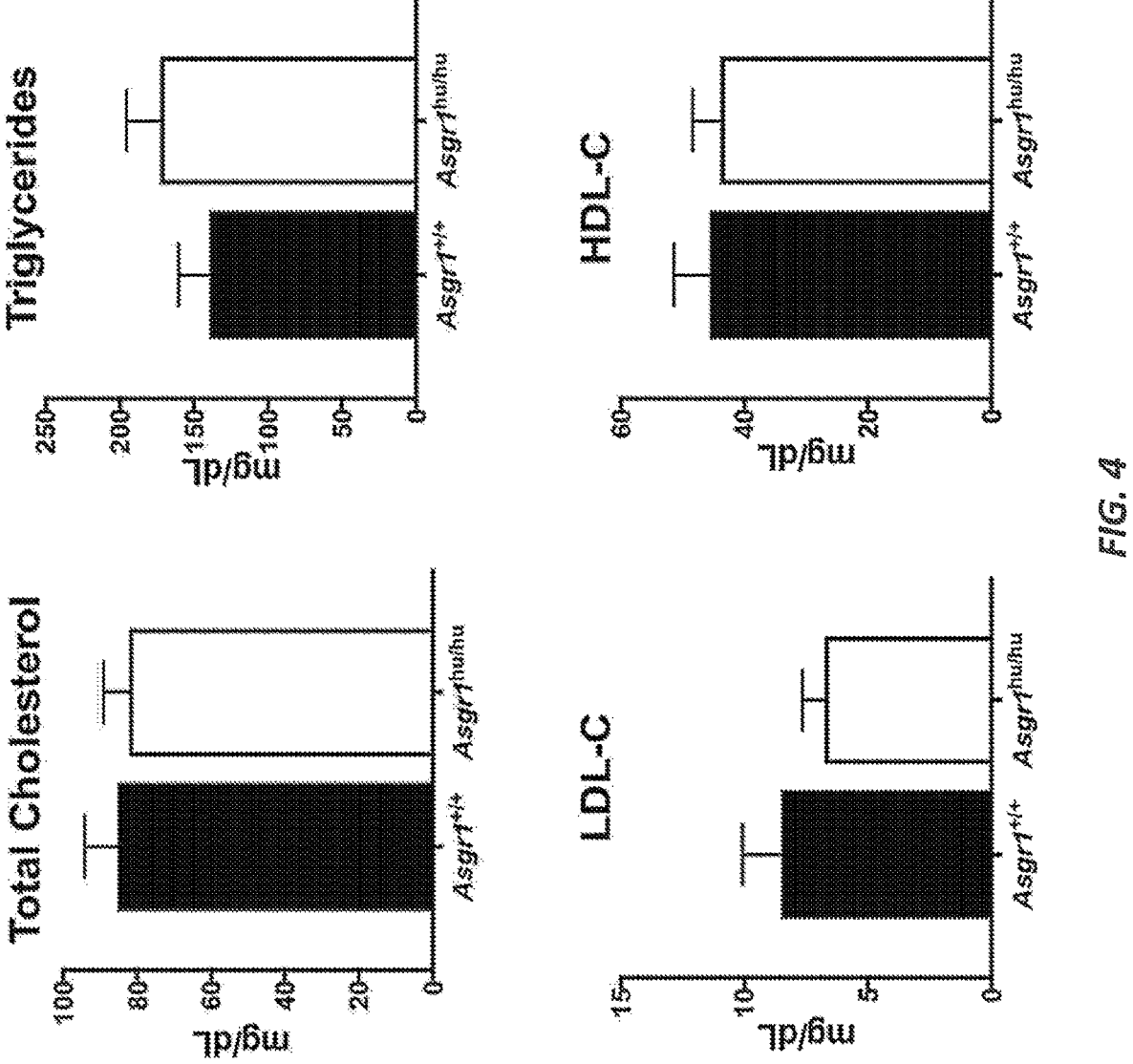
FIG. 4 shows humanized Asgr1 mice (Asgr1$^{hu/hu}$) have plasma lipid profiles (including total cholesterol, triglycerides, LDL-C, and HDL-C) similar to their wild-type (Asgr1$^{+/+}$) littermates.
Figure 6:
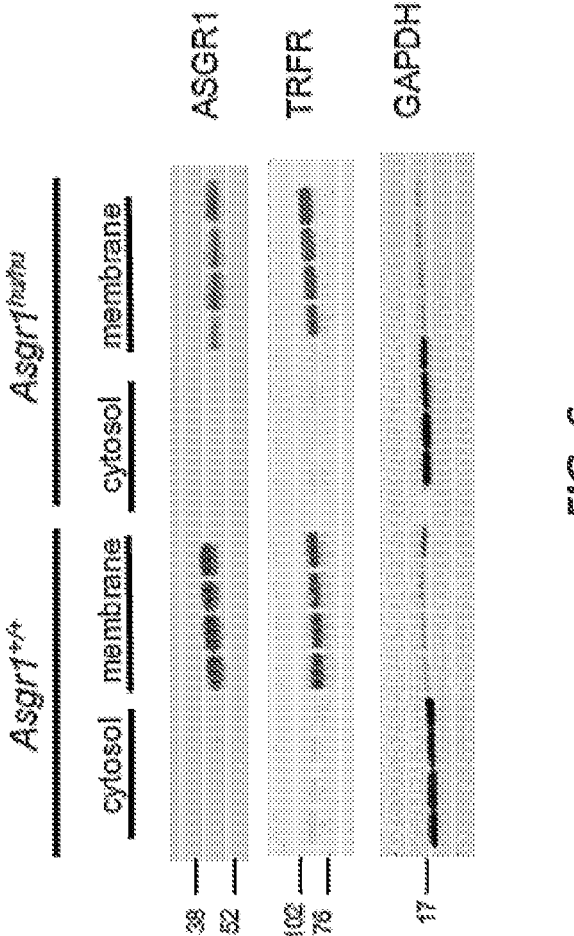
FIG. 6 shows that humanized Asgr1 protein in humanized Asgr1 mice (Asgr1$^{hu/hu}$) co-localizes to liver membranes, similar to mouse Asgr1. Transferrin receptor (TRFR) and glyceraldehyde-3-phosphate dehydrogenase (GAPDH) were used as loading controls for membrane and cytosol fractions of the livers, respectively. N=4 per group shown.
Figure 7:
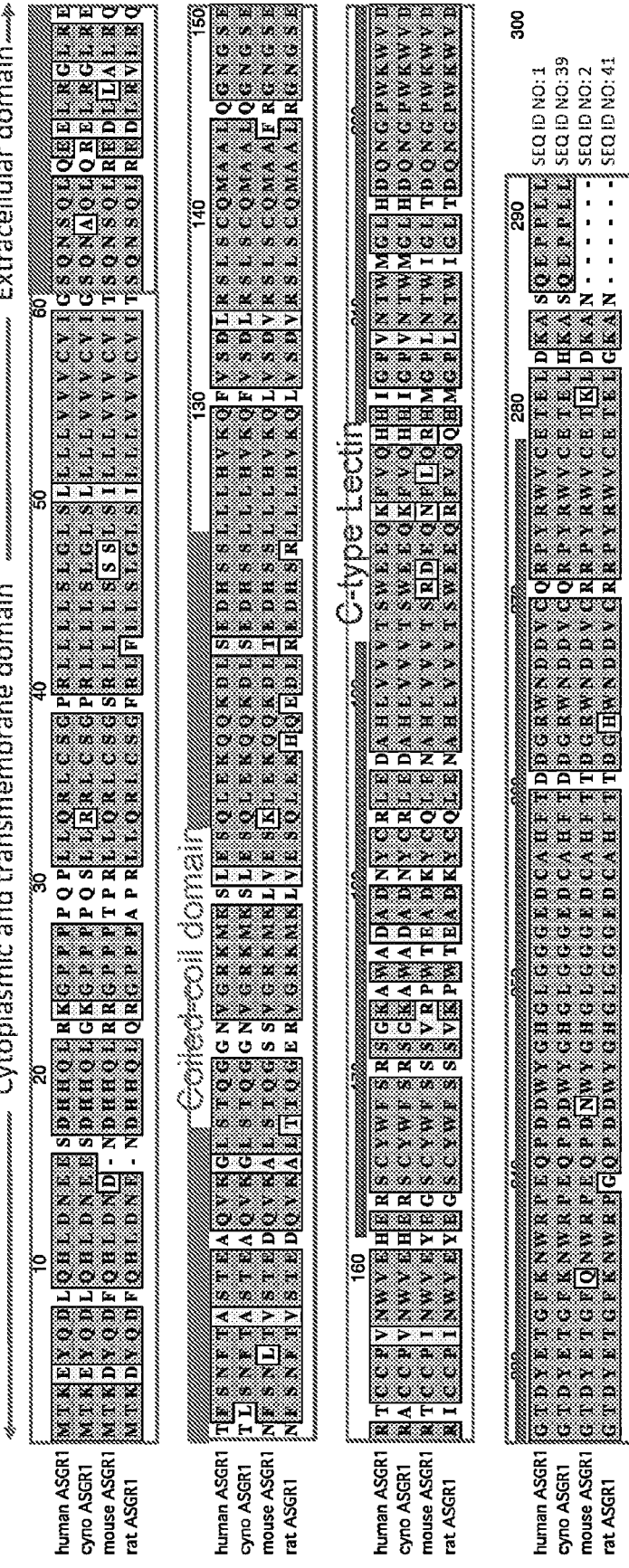
FIG. 7 shows an alignment of the human ASGR1 protein (SEQ ID NO: 1), the *Macaca fascicularis* (cyno) (SEQ ID NO: 39), the mouse Asgr1 protein (SEQ ID NO: 2), and the rat Asgr1 protein (SEQ ID NO: 41). The underscored residues are those encoded by the introduced human exons. There is 97.6% sequence identity between the human and cyno ASGR1 proteins (98.3% sequence identity in extracellular domain), 77% sequence identity between the human and mouse ASGR1 proteins, and 78.4% sequence identity between the human and rat ASGR1 proteins.

To validate humanized Asgr1 mice (Asgr1$^{hu/hu}$) as a valid model, Asgr1$^{hu/hu}$ mice were phenotyped, and their phenotype was compared to the phenotype of wild-type littermates. Asgr1$^{hu/hu}$ mice showed no difference in plasma lipid levels (total cholesterol, triglycerides, HDL-C, LDL-C) in comparison to wild-type littermates. See FIG. 4. Likewise, Asgr1$^{hu/hu}$ mice showed no difference in body weight or blood glucose level compared to wild-type littermates. See FIG. 5. Human ASGR1 protein was co-localized to liver membranes, similar to mouse Asgr1. See FIG. 6. In conclusion, the Asgr1$^{hu/hu}$ mice express human ASGR1 protein on liver membranes and have a normal plasma lipid profile.

Methods

Circulating lipids level evaluation in Asgr1 humanized mice. Plasma from male Asgr1 humanized mice (Asgr1$^{hum/hum}$) and their wild-type littermates (Asgr1$^{+/+}$) was collected at non-fasted conditions and analyzed for serum lipids (triglycerides (TG), total cholesterol, low-density lipoprotein cholesterol (LDL-C), high-density lipoprotein cholesterol (HDL-C)) using serum chemistry analyzer ADVIA® Chemistry XPT System (Siemens). N=8/group, 11 weeks old. Data expressed as Mean±SEM for each.

Blood glucose evaluation. Blood glucose was measured from tail tip using Accu-Chek glucometer (Roche) at fasted (16 hr) and fed (non-fasted) conditions.

Western blot evaluation of Asgr1. Whole liver was harvested from Asgr1 humanized mice and WT mice (n=8/genotype), and stored frozen at −80° C. until processing. For each sample, a ~40 mg piece of frozen liver was excised from the whole liver, and each piece was placed into a dounce homogenizer and homogenized until an even suspension was obtained. The cytosolic fractions and the membrane fractions of each liver sample were separated using a detergent-based commercial kit (Thermo #89842), according to the manufacturer "soft tissue" protocol. Once the cytosolic fraction and membrane fraction of each sample was isolated, a BCA protein quantification assay (Thermo #23225) was run on the two fractions of each sample, according to the kit protocol for microplate procedure. Western blot samples were prepared for each cytosolic fraction and membrane fraction of each sample, using 5× reducing dye. All samples were prepared at 0.8 μg/μL, and 20 μg of total protein of each sample was loaded into Western blot gels. hASGR1 was detected using rabbit anti-hASGR1 polyclonal antibody (Abgent #AP16133a, at 1:1,000 dilution in 2.5% blocking milk in TBS-T). Because the antibody showed cross-reactivity to the mouse protein, mouse Asgr1 in the littermate mice was detected with the same antibody. The secondary antibody for hASGR1 detection was donkey anti-rabbit IgG-HRP (Jackson #711-035-152, at 0.1 μg/mL in 2.5% blocking milk in TBS-T). As a loading control for cytosolic fractions, GAPDH was detected in all samples using rabbit anti-GAPDH monoclonal antibody (Cell Signaling #2118S, at 1:10,000 dilution in 2.5% blocking milk in TBS-T). The secondary antibody for GAPDH detection was donkey anti-rabbit IgG-HRP (Jackson #711-035-152, at 0.1 μg/mL in 2.5% blocking milk in TBS-T). As a loading control for the membrane fractions, transferrin receptor was detected in all samples using rabbit anti-transferrin receptor polyclonal antibody (R&D #AF2472, at 0.25 μg/mL in 2.5% blocking milk in TBS-T). The secondary antibody for transferrin receptor detection was donkey anti-goat IgG-HRP (Jackson #705-035-147, at 0.2 μg/mL in 2.5% blocking milk in TBS-T).

Example 3. Production of Adeno-Associated Viral Vectors with a Heterologous Epitope An experiment was then performed to determine whether a bispecific anti-myc-ASGR1 antibody could retarget scAAV-N587myc viral particles to liver cells expressing humanized ASGR1 in vivo in the mice produced in Example 1. To test this, viral particles were first produced.

AAV capsid proteins are modified to contain one of several heterologous epitopes: FLAG, c-myc, hexahistidine, etc. using PCR to generate a plasmid encoding a recombinant capsid protein. Briefly, the sequence encoding FLAG, c-myc or hexahistidine is inserted in frame after the codon encoding N587 of an AAV2 or Q585 of an AAV6 VP1 capsid protein.

Adeno-associated virus production is performed using a triple transfection method with HEK293 cells (see, e.g., Erik Arden and Joseph M. Metzger, *J Biol Methods.* 2016; 3(2)). Cells are plated one day prior to PEFpro (Polyplus transfection, New York, NY)-mediated transfection with appropriate vectors:

a helper plasmid, pHelper (Agilent, Cat #240074);

a plasmid encoding the wild-type or modified AAV rep/cap gene (pAAV RC2 (Cell biolabs, Cat #VPK-422), e.g., pAAV RC2/6 (Cell Biolabs, Cat #VPK-426), pAAV RC2-N587myc, pAAV RC2/6-Q585myc), etc.; and a plasmid encoding a nucleotide of interest and AAV ITR sequences, e.g., pscAAV-CMV-eGFP, pAAV-CMVGFP (Agilent Cat #240074), pAAV-EF1a-eGFP or pAAV-CAGG-eGFP), etc.

Seventy-two hours after transfection, medium is collected and cells are lysed in buffer [50 mM Tris-HCl, 150 mM NaCl and 0.5% Sodium Deoxycholate (Sigma, Cat #D6750-100G)]. Next, benzonase (Sigma, St. Louis, MO) is added to both medium and cell lysate to a final concentration of 0.5 U/µL before incubation at 37° C. for 60 minutes. Cell lysate is spun down at 4000 rpm for 30 min. Cell lysate and medium are combined together and precipitated with PEG 8000 (Teknova Cat #P4340) at a final concentration of 8%. Pellet is resuspended in 400 mM NaCl and centrifuged at 10000 g for 10 min. Viruses in the supernatant are pelleted by ultracentrifugation at 149,000 g for 3 hours and titered by qPCR.

For qPCR to titrate AAV genomes, AAV samples are treated with DNase1 (Thermofisher Scientific, Cat #EN0525) at 37° C. for one hour and lysed using DNA extract All Reagents (Thermofisher Scientific Cat #4403319). Encapsidated viral genomes are quantified using a QuantStudio 3 Real-Time PCR System (Thermofisher Scientific) using primers directed to the AAV2 ITRs. The sequences of the AAV2 ITRs primers are 5'-GGAACCCCTAGTGATGGAGTT-3' (fwd ITR; SEQ ID NO: 36) and 5'-CGGCCTCAGTGAGCGA-3' (rev ITR; SEQ ID NO: 37) (Aurnhammer et al., 2012), derived the left internal inverted repeat (ITR) sequence from of the AAV and the right internal inverted repeat (ITR) sequence from of the AAV, respectively. The sequence of the AAV2 ITRs probe is 5'-6-FAM-CACTCCCTCTCTGCGCGCTCG-TAMRA-3' (SEQ ID NO: 38) (Aurnhammer et al. (2012) *Hum. Gene Ther. Methods* 23:18-28). After a 95° C. activation step for 10 min, a two-step PCR cycle is performed at 95° C. for 15 seconds and 60° C. for 30 seconds for 40 cycles. The TaqMan Universal PCR Master Mix (Thermofisher Scientific, Cat #4304437) was used in the qPCR. DNA plasmid (Agilent, Cat #240074) is used as standard to determine absolute titers.

Adeno-associated viral vectors comprising a capsid in which a c-myc epitope was inserted were produced. In this example, a c-myc epitope (EQKLISEEDL; SEQ ID NO: 25) was inserted between amino acids N587 and R588 of the AAV2 VP1 capsid protein, i.e., the nucleotide sequence encoding the c-myc epitope (GAA CAA AAA CTC ATC TCA GAA GAG GAT CTG; SEQ ID NO: 26) was inserted into plasmid pAAV RC2 (Cell Biolabs, Inc., San Diego, CA), and the modified pAAV RC2-N587Myc plasmid was used to encode the modified capsid protein for AAV viral vectors with a neutralized tropism.

Specifically, a first polymerase chain reaction (PCR) product comprising (from 5' to 3') a BsiW1 restriction site, the nucleotide sequence between positions 3050 and 3773 of pAAV RC2, and a c-myc epitope overhang nucleotide sequence, and a second PCR product comprising (from 5' to 3') a c-myc epitope overhang nucleotide sequence, the nucleotide sequence between positions 3774 to 4370 of pAAV RC2, and a Pme1 restriction site were created using the primers set forth in Table 4. The pAAV RC2-N587Myc plasmid (i.e., a pAAV RC2 plasmid modified to encode the c-myc epitope between amino acids N587 and R588 of the VP1 capsid protein) was created by digesting pAAV RC2 with BsiW1 (New England Biolabs, R0553L) and Pme1 (New England Biolabs, R0560L), and inserting the two PCR products via ligation-independent cloning as described in Li et al. (2012) Methods Mol. Biol. 852:51-59.

TABLE 4

| PCR Product | Primer Name | 5'-Sequence-3' and SEQ ID NO |
|---|---|---|
| 3050-3773 PAAVRC2-cMyc | PAAVRCBsiWF | GGAGTACCAGCTCCCGT ACG (BsiW1) (SEQ ID NO: 32) |
| | N587myCR | CTCTTCTGAGATGAGTTTT TGTTCGTTGCCTCTCTGGA GGTTG (SEQ ID NO: 33) |
| cMyc-3774-4370 PAA VRC2 | N587mycF | AAACTCATCTCAGAAGAGG ATCTGAGACAAGCA GCTACCGCAG (SEQ ID NO: 34) |
| | PAAVRCPmeR | TCCGCCCGCTGTTTAAAC (Pme1) (SEQ ID NO: 35) |

Underlined sequences represent restriction enzyme recognition sites.

Specifically, a gblock DNA fragment comprising positions of 3700 and 3940 of pAAV RC2/6 with c-myc-epitope sequence inserted between 3757 and 3758 was ordered from Integrated DNA Technologies (Coralville, Iowa). pAAV RC2/6-Q585Myc plasmid was created by insertion of the gblock fragment into pAAV RC2/6 digested with MscI (New England Biolabs, Cat #R0534L) and AflII (New England Biolabs, Cat #R0520L) via ligation-independent cloning as described in Li et al. (2012) *Methods Mol. Biol.* 852:51-59.

Specifically, pscAAV-CMV-eGFP was produced by introducing the GFP fragment into pscAAV MCS vector (Cell Biolabs, Cat #VPK-430) using BamHI and NotI restriction sites. pAAV-EF1 a-eGFP plasmid and pAAV-CAGG-eGFP was made de novo synthesis from Thermofisher Scientific (Waltham, MA).

Example 4. Bispecific-Antibody-Mediated Internalization of scAAV-N587Myc Particles in Mice with Humanized ASGR1 Locus In Vivo To determine whether the bispecific anti-myc-ASGR1 antibody could retarget scAAV2-N587myc-CMV-eGFP viral vectors to liver cells expressing hASGR1 in vivo, mice genetically modified such that their liver cells express hASGR1 on C57BL/6 background, and control wild-type C57BL/6 mice were injected with $1 \times 10^{11}$ (titrated by qPCR) of wild-type scAAV2-CMV-eGFP alone or scAAV2-N587myc-CMV-eGFP viral vectors in combination with bispecific anti-myc-ASGR1 antibody and at 1:8 ratio of viral genome to antibody molecules intravascularly. Controls included mice injected with saline [250 mM NaCl] or with scAAV2-N587myc-CMV-eGFP viral vector alone. Ten days post-injection, mice were sacrificed and transcardial perfused with 4% PFA. Organs of livers, kidney and heart were collected and dehydrated in 15% sucrose followed by 30% sucrose. Then organs were cryo-sectioned on slides and stained with chicken anti-EGFP antibody (Jackson ImmunoResearch Labs, Inc. West Grove, PA) and Alexa-488 conjugated anti-chicken secondary antibody (Jackson ImmunoResearch Labs, Inc. West Grove, PA) (FIGS.

Figure 8A:
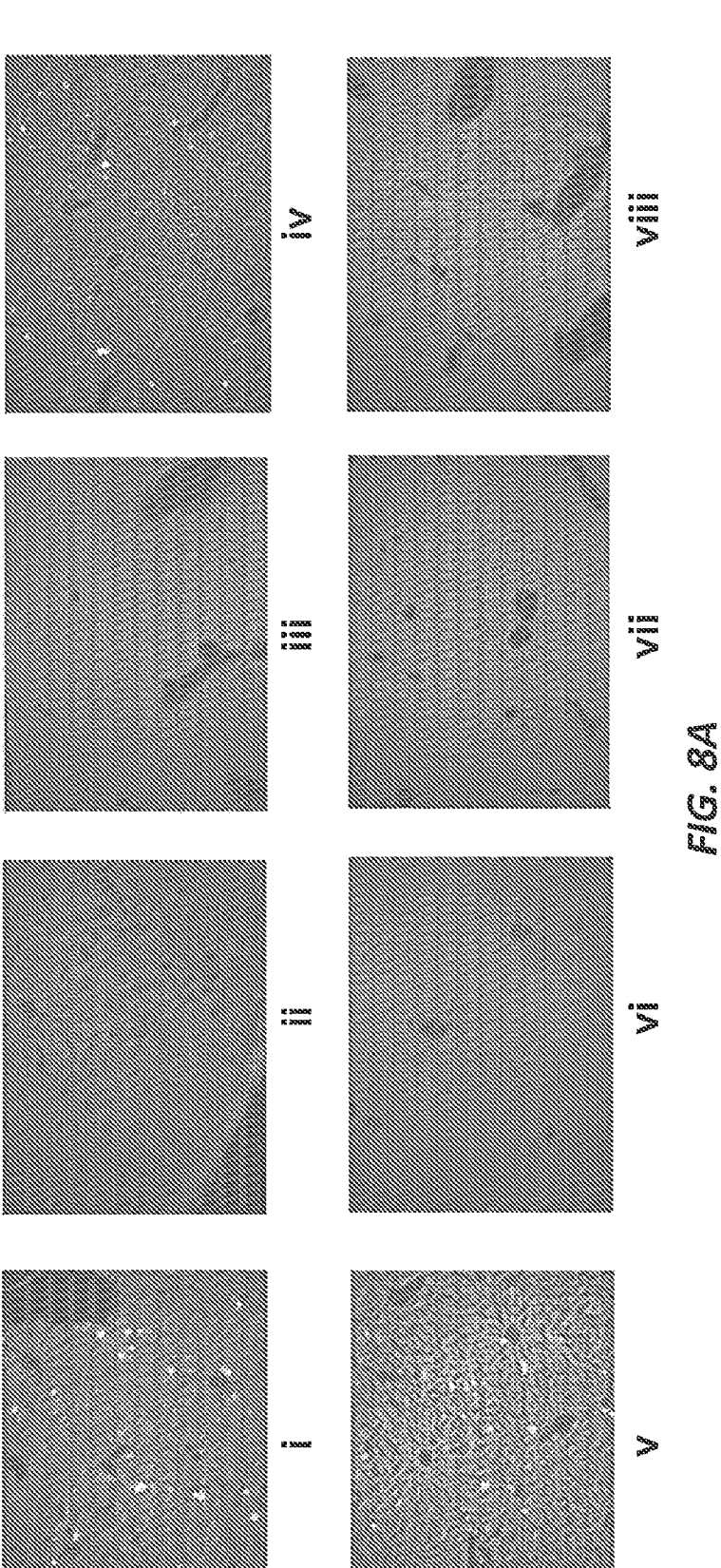
FIGS. 8A-8C provide immunofluorescence microscopy images of liver (A), spleen (B), or kidney (C) samples taken from C57BL/6 mice transgenically modified to express human ASGR1 by liver cells (i-iv) or wildtype C57BL/6 mice (v-viii) ten days post-intravenous-injection with 1×10$^{11}$ wild-type scAAV2-CMV-eGFP (i, v), saline (ii, vi), 1×10$^{11}$ scAAV2-N587myc-CMV-eGFP viral vectors alone (iii, vii), or scAAV2-N587myc-CMV-eGFP viral vectors with bispecific anti-myc-ASGR1 antibody (iv, viii).
Figure 8B:
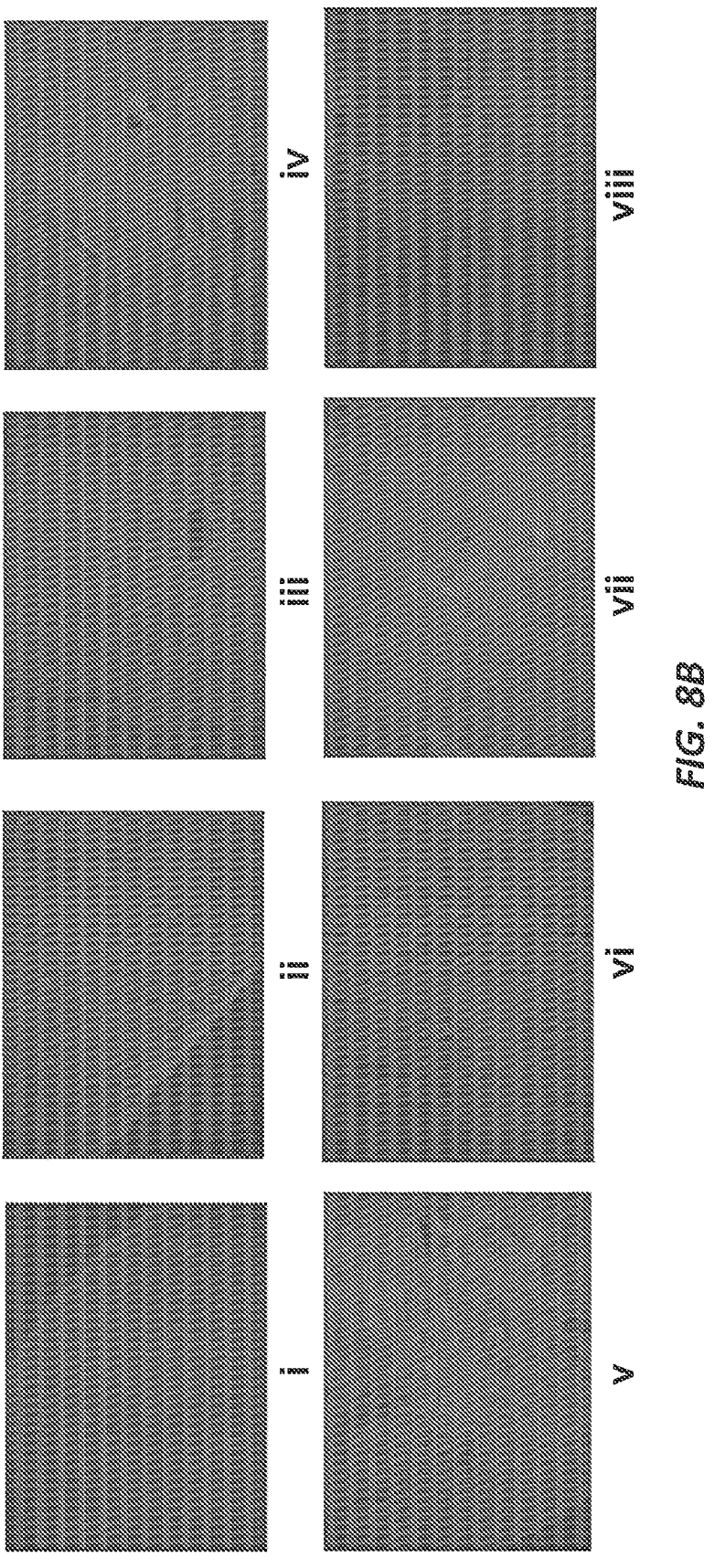
Figure 8C:
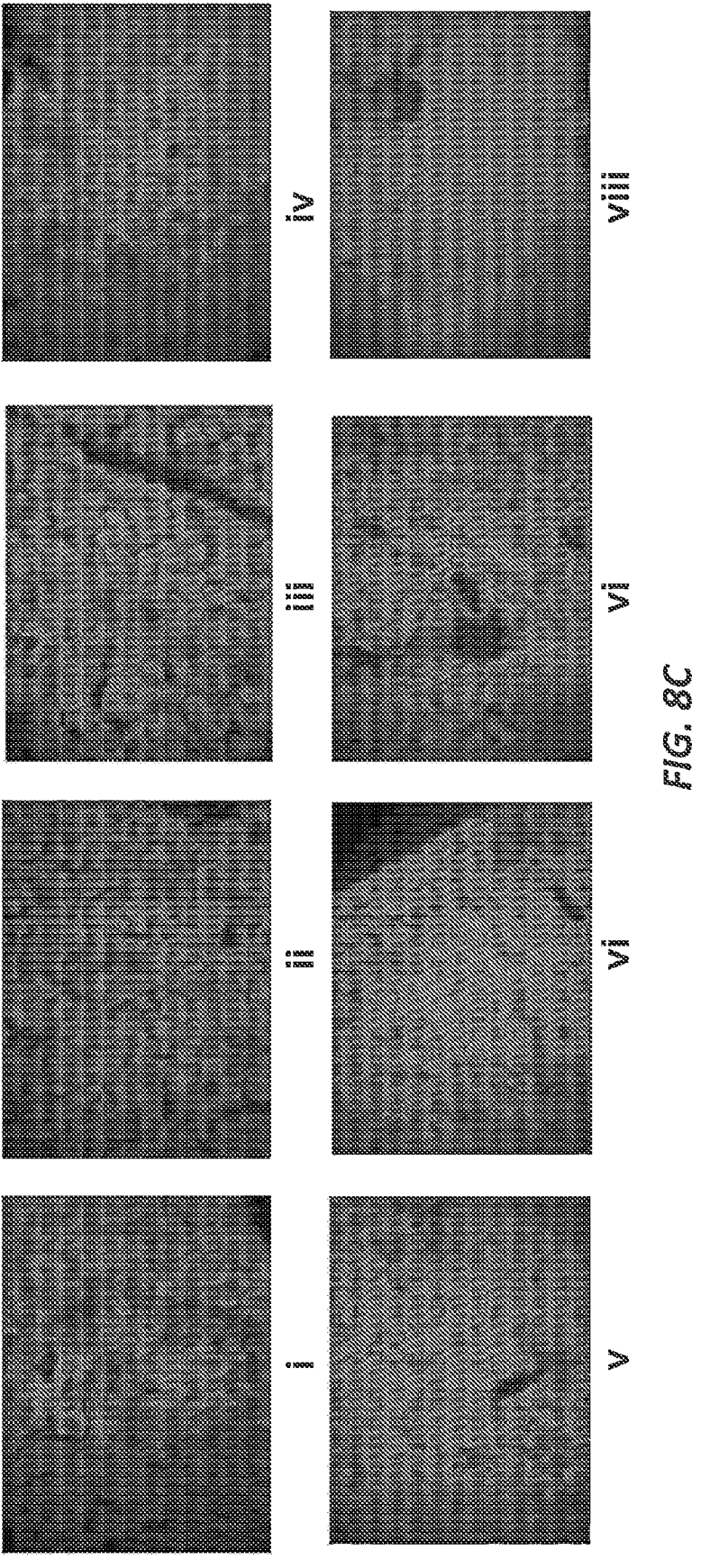

8A-8C). GFP-positive cells were detected in livers from those transgenic animals modified to express ASGR1 in the liver and injected with wildtype scAAV2-CMV-eGFP or scAAV2-N587myc-CMV-eGFP in combination with bispecific anti-myc-ASGR1 antibody (FIGS. 8A(i) and 8A(iv)), and in livers from wild-type C57BL/6 mice injected with wild-type scAAV2-CMV-eGFP (FIG. 8A(v)). GFP was not detected in any spleen or kidney samples (FIGS. 8B and 8C), nor in liver, spleen or kidney samples from any animal injected with saline or scAAV2-N587myc-CMV-eGFP viral vectors alone (FIGS. 8A(ii, iii, vi, vii)), nor in liver samples taken from wild-type C57BL/6 animals injected with scAAV2-N587myc-CMV-eGFP in combination with bispecific anti-myc-ASGR1 antibody (FIG. 8A(viii)). In summary, the combination of scAAV2-N587myc-CMV-eGFP viral vectors and bispecific anti-myc-ASGR1 antibody infected only those (liver) cells expressing hASGR1, strongly suggesting that the scAAV2-CMV-eGFP viral vector was inactivated by the modification of the capsid protein, e.g., natural tropism of the scAAV viral vector could be neutralized, e.g., with a c-myc epitope, and such viral vectors could be specifically reactivated, e.g., specifically retargeted, e.g., to liver cells in vivo, e.g., by bispecific anti-myc-ASGR1 antibodies.

Figures 9M, 9N, 9O, 9P, 9Q, 9R:
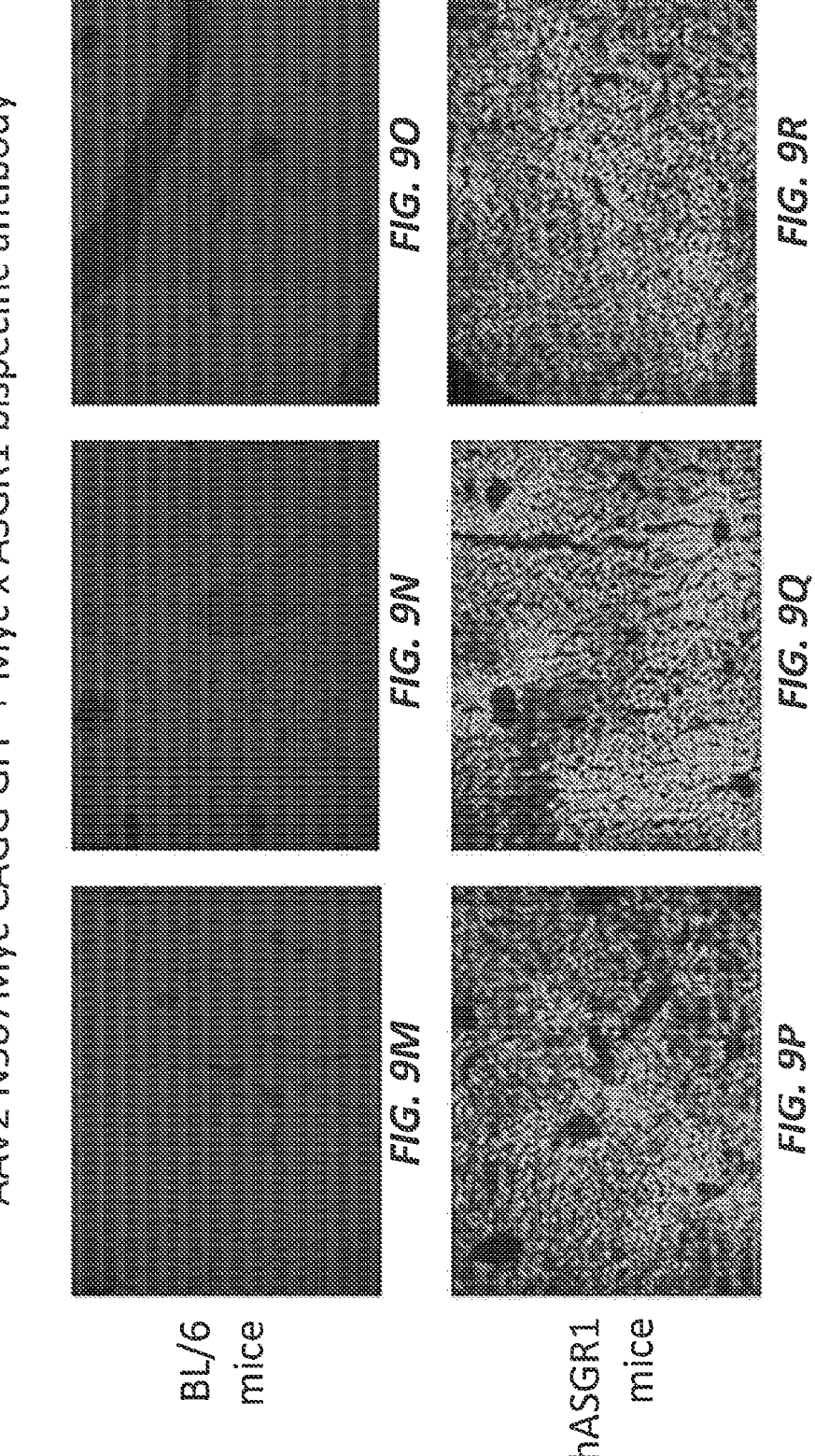

Similarly, to determine whether the bispecific anti-myc-ASGR1 antibody could retarget ssAAV2-N587myc-CAGG-eGFP viral vectors to liver cells expressing hASGR1 in vivo, mice genetically modified such that their liver cells express hASGR1 on C57BL/6 background, and control wild-type C57BL/6 mice were injected with 2.18×10$^{11}$ (titrated by qPCR) of wild-type ssAAV2-CAGG-eGFP alone or ssAAV2-N587myc-CAGG-eGFP viral vectors in combination with bispecific anti-myc-ASGR1 antibody and at 1:4 ratio of viral genome to antibody molecules intravascularly. Controls included mice injected with PBS or with ssAAV2-N587myc-CAGG-eGFP viral vector alone. Four weeks post-injection, mice were sacrificed and transcardial perfused with 4% PFA. Organs of livers, kidney and heart were collected and dehydrated in 15% sucrose followed by 30% sucrose. Then organs were cryo-sectioned on slides and stained with chicken anti-EGFP antibody (Jackson ImmunoResearch Labs, Inc. West Grove, PA) and Alexa-488 conjugated anti-chicken secondary antibody (Jackson ImmunoResearch Labs, Inc. West Grove, PA) (FIGS. 9A-9O). GFP-positive cells were detected in livers from those transgenic animals modified to express ASGR1 in the liver and injected with wildtype ssAAV2-CAGG-eGFP or ssAAV2-N587myc-CAGG-eGFP in combination with bispecific anti-myc-ASGR1 antibody (FIGS. 9E-9F, 9P-9R), and in livers from wild-type C57BL/6 mice injected with wild-type ssAAV2-CAGG-eGFP (FIG. 9B-9C). Surprisingly, the infection efficiency of ssAAV2-N587myc-CAGG-eGFP in combination with bispecific anti-myc-ASGR1 antibody is much higher than WT ssAAV2-CAGG-GFP (FIGS. 9E-9F, 9P-9R). GFP was not detected or barely detected in liver samples from any animal injected with saline or ssAAV2-N587myc-CAGG-eGFP viral vectors alone (FIGS. 9A, 9D, 9G-9L)), nor in liver samples taken from wild-type C57BL/6 animals injected with ssAAV2-N587myc-CAGG-eGFP in combination with bispecific anti-myc-ASGR1 antibody (FIG. 9M-9O). In summary, the combination of ssAAV2-N587myc-CAGG-eGFP viral vectors and bispecific anti-myc-ASGR1 antibody infected only those (liver) cells expressing hASGR1, strongly suggesting that the ssAAV2-N587myc-CAGG-eGFP viral vector was inactivated by the modification of the capsid protein, e.g., natural tropism of the scAAV viral vector could be neutralized, e.g., with a c-myc epitope, and such viral vectors could be specifically reactivated, e.g., specifically retargeted, e.g., to liver cells in vivo, e.g., by bispecific anti-myc-ASGR1 antibodies.

This example demonstrates that humanized ASGR1 mice may be used to test potential therapeutics that specifically bind to human ASGR1 for targeted delivery to liver cells.

---

We claim:

1. A nucleic acid comprising a first nucleic acid sequence that encodes the amino acid sequence as set forth in SEQ ID NO: 3, wherein the nucleic acid further comprises a second nucleic acid sequence selected from the group consisting of the nucleic acid sequence as set forth in SEQ ID NO: 18, the nucleic acid sequence as set forth in SEQ ID NO: 19, the nucleic acid sequence as set forth in SEQ ID NO: 20, and the nucleic acid sequence as set forth in SEQ ID NO:23.

2. The nucleic acid of claim 1, comprising the nucleic acid sequence as set forth in SEQ ID NO:24.

3. The nucleic acid of claim 1, comprising the nucleic acid sequence as set forth in SEQ ID NO: 21.

4. A targeting vector comprising the nucleic acid of claim 1 flanked by 5' and 3' homology arms corresponding to 5' and 3' target sites within an endogenous mouse Asgr1 locus.

5. A targeting vector comprising the nucleic acid of claim 2 flanked by 5' and 3' homology arms corresponding to 5' and 3' target sites within an endogenous mouse Asgr1 locus.

6. A targeting vector comprising the nucleic acid of claim 3 flanked by 5' and 3' homology arms corresponding to 5' and 3' target sites within an endogenous mouse Asgr1 locus.

* * * * *

SEQUENCE LISTING

```
Sequence total quantity: 42
SEQ ID NO: 1            moltype = AA  length = 291
FEATURE                 Location/Qualifiers
REGION                  1..40
                        note = MISC_FEATURE - Cytoplasmic Domain
REGION                  41..61
                        note = MISC_FEATURE - Transmembrane Domain
REGION                  61..123
                        note = MISC_FEATURE - Coiled-Coil Domain
REGION                  161..278
                        note = MISC_FEATURE - C-Type Lectin Domain
source                  1..291
                        mol_type = protein
                        organism = Homo sapiens
SEQUENCE: 1
MTKEYQDLQH LDNEESDHHQ LRKGPPPPQP LLQRLCSGPR LLLLSLGLSL LLLVVVCVIG   60
SQNSQLQEEL RGLRETFSNF TASTEAQVKG LSTQGGNVGR KMKSLESQLE KQQKDLSEDH  120
SSLLLHVKQF VSDLRSLSCQ MAALQGNGSE RTCCPVNWVE HERSCYWFSR SGKAWADADN  180
YCRLEDAHLV VVTSWEEQKF VQHHIGPVNT WMGLHDQNGP WKWVDGTDYE TGFKNWRPEQ  240
PDDWYGHGLG GGEDCAHFTD DGRWNDDVCQ RPYRWVCETE LDKASQEPPL L           291

SEQ ID NO: 2            moltype = AA  length = 284
FEATURE                 Location/Qualifiers
REGION                  1..39
                        note = MISC_FEATURE - Cytoplasmic Domain
REGION                  40..60
                        note = MISC_FEATURE - Transmembrane Domain
REGION                  60..122
                        note = MISC_FEATURE - Coiled-Coil Domain
REGION                  160..277
                        note = MISC_FEATURE - C-Type Lectin Domain
```

```
source                    1..284
                          mol_type = protein
                          organism = Mus musculus
SEQUENCE: 2
MTKDYQDFQH LDNDNDHHQL RRGPPPTPRL LQRLCSGSRL LLLSSSLSIL LLVVVCVITS    60
QNSQLREDLL ALRQNFSNLT VSTEDQVKAL STQGSSVGRK MKLVESKLEK QQKDLTEDHS   120
SLLLHVKQLV SDVRSLSCQM AAFRGNGSER TCCPINWVEY EGSCYWFSSS VRPWTEADKY   180
CQLENAHLVV VTSRDEQNFL QRHMGPLNTW IGLTDQNGPW KWVDGTDYET GFQNWRPEQP   240
DNWYGHGLGG GEDCAHFTTD GRWNDDVCRR PYRWVCETKL DKAN                    284

SEQ ID NO: 3              moltype = AA   length = 290
FEATURE                   Location/Qualifiers
REGION                    1..290
                          note = Synthetic
REGION                    1..39
                          note = MISC_FEATURE - Cytoplasmic Domain
REGION                    40..60
                          note = MISC_FEATURE - Transmembrane Domain
REGION                    60..122
                          note = MISC_FEATURE - Coiled-Coil Domain
REGION                    62..290
                          note = MISC_FEATURE - Residues Encoded by Introduced Human
                           Exons
REGION                    160..277
                          note = MISC_FEATURE - C-Type Lectin Domain
source                    1..290
                          mol_type = protein
                          organism = synthetic construct
SEQUENCE: 3
MTKDYQDFQH LDNDNDHHQL RRGPPPTPRL LQRLCSGSRL LLLSSSLSIL LLVVVCVITS    60
QNSQLQEELR GLRETFSNFT ASTEAQVKGL STQGGNVGRK MKSLESQLEK QQKDLSEDHS   120
SLLLHVKQFV SDLRSLSCQM AALQGNGSER TCCPVNWVEH ERSCYWFSRS GKAWADADNY   180
CRLEDAHLVV VTSWEEQKFV QHHIGPVNTW MGLHDQNGPW KWVDGTDYET GFKNWRPEQP   240
DDWYGHGLGG GEDCAHFTDD GRWNDDVCQR PYRWVCETEL DKASQEPPLL             290

SEQ ID NO: 4              moltype = DNA   length = 855
FEATURE                   Location/Qualifiers
source                    1..855
                          mol_type = genomic DNA
                          organism = Mus musculus
SEQUENCE: 4
atgacaaagg attatcaaga tttccagcac ctggacaatg ataatgacca tcatcaactc    60
cggagagggc cgcctcccac tccacggctc ttgcagcgac tctgctctgg atcccgcctc   120
ctcctgctct cctcgagcct cagcattctg ttgctggtgg ttgtctgtgt gatcacatcc   180
caaaattccc aactccggga agatctgctg gctctaaggc agaatttcag caacctcact   240
gtgagcactg aggaccaggt caaggccctg agcacccagg gaagtagtgt gggaagaaag   300
atgaagttag tggagtcgaa gctggaaaaa cagcagaagg atctgactga agatcactcc   360
agtttgctac tgcacgtgaa gcagttagtg tctgacgtgc gaagcttgag ctgccagatg   420
gctgcatttc ggggcaatgg ctctgaaagg acctgctgcc ccatcaactg ggtggagtat   480
gaaggcagct gctactggtt ctccagctct gtgaggcctt ggactgaagc tgacaagtac   540
tgccagctgg aaaatgccca tctggtggtg gtgacctcca gggatgagca gaacttcctc   600
cagcgccaca tgggccccTt aaacacttgg attggcctaa ctgaccagaa cgggccctgg   660
aaatgggtgg atggaacaga ctacgagaca ggcttccaga attggagacc agagcagcca   720
gataactggt acggacatgg gcttggagga ggcgaggact gtgcccactt cacgacggat   780
ggccgctgga atgacgacgt ctgcaggagg ccctaccgct gggtctgtga gacaaagttg   840
gataaggcta attag                                                    855

SEQ ID NO: 5              moltype = DNA   length = 876
FEATURE                   Location/Qualifiers
source                    1..876
                          mol_type = genomic DNA
                          organism = Homo sapiens
SEQUENCE: 5
atgaccaagg agtatcaaga ccttcagcat ctggacaatg aggagagtga ccaccatcag    60
ctcagaaaag ggccacctcc tccccagccc ctcctgcagc gtctctgctc cggacctcgc   120
ctcctcctgc tctccctggg cctcagcctc ctgctgcttg tggttgtctg tgtgatcgga   180
tcccaaaact cccagctgca ggaggagctg cggggcctga gagagacgtt cagcaacttc   240
acagcgagca cggaggccca ggtcaagggc ttgagcaccc agggaggcaa tgtgggaaga   300
aagatgaagt cgctagagtc ccagctggag aaacagcaga agacctgagc tgaagatcac   360
tccagcctgc tgctccacgt gaagcagttc gtgtctgacc tgcggagcct gagctgtcag   420
atggcggcgc tccagggcaa tggctcagaa aggacctgct gcccggtcaa ctgggtggag   480
cacgagcgca gctgctactg gttctctcgc tccgggaagg cctgggctga cgccgacaac   540
tactgccggc tggaggacgc gcacctggtg gtggtcacgt cctgggagga gcagaaattt   600
gtccagcacc acataggccc tgtgaacacc tggatgggcc tgcacgacca aaacgggccc   660
tggaagtggg tggacgggac ggactacgag acgggcttca gaactgagg ccggagcag   720
ccggacgact ggtacggcca cgggctcgga ggagcgagg actgtgccca cttcaccgac   780
gacgccgct ggaacgacga cgtctgccag aggccctacc gctgggtctg cgagacagag   840
ctggacaagg ccagccagga gccacctctc cttttaa                           876
```

-continued

```
SEQ ID NO: 6          moltype = DNA   length = 19
FEATURE               Location/Qualifiers
misc_feature          1..19
                      note = Synthetic
source                1..19
                      mol_type = other DNA
                      organism = synthetic construct
SEQUENCE: 6
tcccaactcc gggaagatc                                          19

SEQ ID NO: 7          moltype = DNA   length = 24
FEATURE               Location/Qualifiers
misc_feature          1..24
                      note = Synthetic
source                1..24
                      mol_type = other DNA
                      organism = synthetic construct
SEQUENCE: 7
tgctggctct aaggcagaat ttca                                    24

SEQ ID NO: 8          moltype = DNA   length = 20
FEATURE               Location/Qualifiers
misc_feature          1..20
                      note = Synthetic
source                1..20
                      mol_type = other DNA
                      organism = synthetic construct
SEQUENCE: 8
tcagtgctca cagtgaggtt                                         20

SEQ ID NO: 9          moltype = DNA   length = 22
FEATURE               Location/Qualifiers
misc_feature          1..22
                      note = Synthetic
source                1..22
                      mol_type = other DNA
                      organism = synthetic construct
SEQUENCE: 9
gggttggctc atgttaggaa gg                                      22

SEQ ID NO: 10         moltype = DNA   length = 20
FEATURE               Location/Qualifiers
misc_feature          1..20
                      note = Synthetic
source                1..20
                      mol_type = other DNA
                      organism = synthetic construct
SEQUENCE: 10
tcagcagccg agctgtgaaa                                         20

SEQ ID NO: 11         moltype = DNA   length = 22
FEATURE               Location/Qualifiers
misc_feature          1..22
                      note = Synthetic
source                1..22
                      mol_type = other DNA
                      organism = synthetic construct
SEQUENCE: 11
caggctgtgc tacccaaagt tc                                      22

SEQ ID NO: 12         moltype = DNA   length = 21
FEATURE               Location/Qualifiers
misc_feature          1..21
                      note = Synthetic
source                1..21
                      mol_type = other DNA
                      organism = synthetic construct
SEQUENCE: 12
ggaggcaatg tgggaagaaa g                                       21

SEQ ID NO: 13         moltype = DNA   length = 24
FEATURE               Location/Qualifiers
misc_feature          1..24
                      note = Synthetic
source                1..24
                      mol_type = other DNA
                      organism = synthetic construct
SEQUENCE: 13
tgaagtcgct agagtcccag ctgg                                    24
```

-continued

```
SEQ ID NO: 14              moltype = DNA   length = 20
FEATURE                    Location/Qualifiers
misc_feature               1..20
                           note = Synthetic
source                     1..20
                           mol_type = other DNA
                           organism = synthetic construct
SEQUENCE: 14
tcaggtcctt ctgctgtttc                                            20

SEQ ID NO: 15              moltype = DNA   length = 20
FEATURE                    Location/Qualifiers
misc_feature               1..20
                           note = Synthetic
source                     1..20
                           mol_type = other DNA
                           organism = synthetic construct
SEQUENCE: 15
gattgggaat ccgcccatct                                            20

SEQ ID NO: 16              moltype = DNA   length = 29
FEATURE                    Location/Qualifiers
misc_feature               1..29
                           note = Synthetic
source                     1..29
                           mol_type = other DNA
                           organism = synthetic construct
SEQUENCE: 16
cctcttctgc tttctcggga attttcatc                                  29

SEQ ID NO: 17              moltype = DNA   length = 20
FEATURE                    Location/Qualifiers
misc_feature               1..20
                           note = Synthetic
source                     1..20
                           mol_type = other DNA
                           organism = synthetic construct
SEQUENCE: 17
aaagcgccac gggtttcaag                                            20

SEQ ID NO: 18              moltype = DNA   length = 120
FEATURE                    Location/Qualifiers
misc_feature               1..120
                           note = Synthetic
misc_feature               1..60
                           note = Mouse Sequence
misc_feature               61..120
                           note = Human Sequence
source                     1..120
                           mol_type = other DNA
                           organism = synthetic construct
SEQUENCE: 18
catcccaaag tgggtggcca gggctgggca gagaaagggg gcaacttcgg gtgtgtgtga  60
caagggagtg gtgggtgcag tggtggcgga cacagcgatc ccgtttttctt ctctctgcac 120

SEQ ID NO: 19              moltype = DNA   length = 160
FEATURE                    Location/Qualifiers
misc_feature               1..160
                           note = Synthetic
misc_feature               1..60
                           note = Human Sequence
misc_feature               61..66
                           note = XhoI
misc_feature               67..100
                           note = loxP
misc_feature               101..160
                           note = Cassette
source                     1..160
                           mol_type = other DNA
                           organism = synthetic construct
SEQUENCE: 19
tgttatttac agatacgtga gtttgggcaa attattgttc tctgtgtccc agctgtaaac  60
ctcgagataa cttcgtataa tgtatgctat acgaagttat atgcatggcc tccgcgccgg 120
gttttggcgc ctcccgcggg cgcccccctc ctcacggcga                      160

SEQ ID NO: 20              moltype = DNA   length = 191
FEATURE                    Location/Qualifiers
misc_feature               1..191
```

-continued

```
                        note = Synthetic
misc_feature            1..60
                        note = Cassette
misc_feature            61..94
                        note = loxP
misc_feature            100..125
                        note = I-CeuI
misc_feature            126..131
                        note = NheI
misc_feature            132..191
                        note = Mouse Sequence
source                  1..191
                        mol_type = other DNA
                        organism = synthetic construct
SEQUENCE: 20
tttcactgca ttctagttgt ggtttgtcca aactcatcaa tgtatcttat catgtctgga    60
ataacttcgt ataatgtatg ctatacgaag ttatgctagt aactataacg gtcctaaggt   120
agcgagctag ccgtggacag atacagcaac gtgagctagt tattctgtcc taaagtctca   180
gttggaagat g                                                        191

SEQ ID NO: 21          moltype = DNA  length = 9692
FEATURE                Location/Qualifiers
misc_feature            1..9692
                        note = Synthetic
misc_feature            1..69
                        note = Mouse Sequence
misc_feature            70..3976
                        note = Human Sequence
misc_feature            3977..3982
                        note = XhoI
misc_feature            3983..4016
                        note = loxP
misc_feature            4023..5235
                        note = Human Ubiquitin Promoter
misc_feature            5236..5302
                        note = EM7 Promoter
misc_feature            5303..6328
                        note = Hygromycin Resistance Gene
misc_feature            6329..6813
                        note = PGK polyA
misc_feature            6825..7506
                        note = Prm Promoter
misc_feature            7507..8646
                        note = Crei
misc_feature            8909..9119
                        note = SV40 polyA
misc_feature            9124..9157
                        note = loxP
misc_feature            9163..9188
                        note = I-CeuI
misc_feature            9189..9194
                        note = NheI
misc_feature            9195..9692
                        note = Mouse Sequence
source                  1..9692
                        mol_type = other DNA
                        organism = synthetic construct
SEQUENCE: 21
gtgtgatcac atcccaaagt gggtggccag ggctgggcag agaaaggggg caacttcggg    60
tgtgtgtgac aagggagtgg tgggtgcagt ggtggcggac acagcgatcc cgtttttcttc  120
tctctgcacg ctgtcctggc cagactccca gctgcaggag gagctgcggg gcctgagaga   180
gacgttcagc aacttcacag cgagcacgga ggcccaggtc aagggcttga gcacccaggg   240
tgagggcgct ggggcggggc tggggctggg gctggggctg ggggctgtc gggaacgctg    300
agcgagcctc tcccgcagga ggcaatgtgg gaagaaagat gaagtcgcta gagtcccagc   360
tggagaaaca gcagaaggac ctgagtgaag gtcagagagg gagtgtgtgt gtgtgtgtgt   420
gtgtgtgaaa gagagtgaga atgtgtggat gtgtgtgaga aagtgtgagt gtgtgtggat   480
gtgtgtgaga atgagaggga gtgtgtgtgt gtgtgagtct gtgtgtgaga atgagggga    540
gtgtgttttg ggtgtgtgta tgagagcctt gtgtggatgt gagaatgaga gggagtgtgt   600
atgtctgtga gtgtgagaat gagatggagt gtgtgtgagt ctgtgtgtga gaatgaggtg   660
tgtgtgtgtg agaatgagat ggtgtgtgtg tgggaatgag aggggtgtgt gtctgagtg    720
tgagaatgag atagagtgtg tgtgagacag tctgtgtggaa tgagagggag tgtgtgtgag   780
agtgtgagaa tgacggagtg tgtctgtgag tgtgataatg aggtgtgtgt gagtctgagt   840
gtaagaatga gatggggtgt gtgtgtctgt gagtgtgaga gtgtgagaat gagggggtgtt  900
tgtgtctgag tgtgagtctg tgagtgtgag aatgagatgg ggtgtgtgag tgagtgtgag  960
aatgagatgg ggtgtgtgtg tctgtgagtg tgtgtgtgtt tgtgagtgtg agaatgagat  1020
ggggtgtgtg tgagtgtgag aatgagatgg ggtgtgtgtc tgtgtgtgag aatgagatgg  1080
gtgtgtgtgt gacagagtct gagtgtgaga atgagaggga gtgtgtgtga gtgtgagaat  1140
gagaaggagt ggatggggtgt gtgagtctgt gtgaatgagg gagtgggtgt gtgtacgagt  1200
gtgagtctgt gtttatgtgt gagaatgtgt cagtgtatgt gtgtgagaac gtgtgtatgt  1260
```

-continued

```
gtgttagtgt gtgttgcgtg tgtgggggaa tgagagggat tgtgtctgtg agtgtgagaa  1320
tgagatggag tgtctgtgag actgtgtgtg aggagtggga gtgtgtgtga gaatgagatg  1380
ggtgtgtgtg tctgagtgtg tgtctgtgag aatgagaggg agtgtgtgtg tgtgtgagag  1440
cctgtgtgaa aatgagaagg agtgtggatg ggtgtttgtg agtgggagag tctgtgtgtt  1500
tatgtgtgtg agaatgaggg agtgtgcgaa tgtgagtctg tgtttatgtg              1560
tgtgagaatg tgtcagtgta tgtgagaacg tgtgtgttag tgtgttgcgt gtgtgagaat  1620
gtaagtatat gtgtaagtgc atgtgagtgt gtgtatgtgc gtgttgtgtg aatgtgcatt  1680
gtgtgtgcat gtgtgaaaga gtatatgtgt gttgtgggtg agtgtgtgtg gtgtgtgtag  1740
tgggtgaggg tgtgttgtat gtgtgggtgt gcgttgtgtg aatgtgtgta tgtgggtgag  1800
ggtgtgtgtg cctgtgtgag ggtgtgttgt ggtttttgtg tgtgtttggg tgagggtgtg  1860
ttgtgtgtgt gtgtgggtga aggtgtgttg tgtgtgtcgt gggtgaaggt gtgttgtgtg  1920
tgtagtgact gtagattagg gtgtgttccg tgtgtgtgtg tgagggtgta tgttgtgggt  1980
gttttgtgtg tgagtgggtg tgtaagggtg tgttgtgtgt atgtgggtta aggtgtgtta  2040
tgcgtgaggg tgtattgtgt gtgtgttttg tgtgtgttgt gtgtatgtgg gttagggtgt  2100
gttgtgtgtt tgtgtgtttt gtgtgttgtc tgtgtatgtg ggttacggtg tgttgtgcgt  2160
gtgagggtgt gttgtgtatg gtgtgttgtg tgtgttgtgt gagtgtgtat gtgagttagg  2220
gtgtgttgtg tctatgtatg tgtgtgtaag ggtgtgttgt gtgtctgtgg gtgtgttttg  2280
tgtatgtggg ttagggtgtg ttgtgttgtc tgtattgtgt gttttatgtg ttgtctgtat  2340
gtgggttatg tgtgttgtgt gtgttgtgga tgtatgtggg ttagggtgtg ttgtgtgtct  2400
ctgtgtgttg tctgcgtttg tgtctgtggg ttagggtgtg ttgtatgtgt tgtgttttgt  2460
gtgttgtccg tgtgtgtgta tgtgggttag gttgtgtgtg tgtgtgttgt atattgtctg  2520
tgtgtgtgtg ttaggatgtg ttgtgtgtct gtgtgagtgt gtgtgtaagg gtgtgttgtg  2580
tgtgtaggag tgtgtgtgtg tgtgtgtatg ggggtctctc aggccaactc cgctgctgtt  2640
tgtggcaatg cgacgggtgt tcgggtccca gcaggaggat gtagggctga cctcgtttcc  2700
cgtttccctc cccgtggttt ccgcatctcc tcccgctccc ctccgcccgg tctccccaga  2760
tcactccagc ctgctgctcc acgtgaagca gttcgtgtct gaggtcgcga gcctgagctg  2820
tcagatggcg gcgctccagg gcaatggtaa ggaggccagc ccggcccgct ctctgcctcc  2880
ccccttctct gggcagcgct tagcccctgc gccccgtttc tcccgctcag gctcagaaag  2940
gacctgctgc ccggtcaact gggtggagca cgagcgcagc tgctactggt tctctcgctc  3000
cgggaaggcc tgggctgacg ccgacaacta ctgccgggcg gaggacgcgc acctggtggt  3060
ggtcacgtcc tgggaggagc aggtgaggac ccggagggtc tgggaggctg gctggcctcg  3120
gagagatcac cacccgcctt ctctctcctc agaaatttgt ccagcaccac ataggccctg  3180
tgaacacctg gatgggcctc cacgaccaaa acgggccctg gaagtggggtg gacgggacgg  3240
actacgagac gggcttcaag tgagtgcgcg ccctccctcg gcctgggtcc ggccgccttc  3300
gcgccctggg gccctgggct gaggagtctg gagcgacccg cctgcggatc cgacctcctg  3360
gggcccacag ctggctctgt ccccaggaac tggaggccgg agcagccgga cgactggtac  3420
ggccacgggc tcgaggagg cgaggactgt gcccacttca ccgacgacgg ccgctggaac  3480
gacgacgtct gccagaggcc ctaccgctgg gtctgcgaga cagagctgga caaggccagc  3540
caggagccac ctctccttta atttatttct tcaatgcctc gacctgccgc aggggtccgg  3600
gattgggaat ccgcccatct gggggcctct tctgctttct cgggaatttt catctaggat  3660
tttaagggaa ggggaaggat agggtgatgt tccgaaggtg aggagcttga aacccgtggc  3720
gctttctgca gtttgcaggt tatcattgtg aacttttttt ttttaagagt aaaaagaaat  3780
atacctaaac cttctgttag ttgtctggtt attggggatt cggaagcagg agtgggctgg  3840
ttggcattac gaagccttag cgggtgctgt ggcatcatga gaactgtgtg ggctttgggc  3900
cagaatggcc agactttgtt atttacagat acgtgagttt gggcaaatta ttgttctctg  3960
tgtcccagct gtaaacctcg agataacttc gtataatgta tgctatacga agttatatgc  4020
atggcctccg cgccgggttt tggcgcctcc cgcgggcgcc ccctccctca cggcgagcgc  4080
tgccacgtca gacgaagggc gcagcgagcg tcctgatcct tccgcccgga cgctcaggac  4140
agcggcccgc tgctcataag actcggcctt agaaccccag tatcagcaga aggacatttt  4200
aggacggac ttgggtgact ctagggcact ggttttcttt ccagagagcg gaacaggcga  4260
ggaaaagtag tcccttctcg gcgattctgc ggagggatct ccgtggggcg gtgaacgccg  4320
atgattatat aaggacgcgc gcgggtgtggc acagctagtt ccgtcgcagc cgggatttgg  4380
gtcgcggttc ttgtttgtgg atcgctgtga tcgtcacttg gtgagtagcg ggctgctggg  4440
ctggccgggg cttttcgtgg c cgccgggccg ctcggtggga cggaagcgtg tggagagacc  4500
gccaagggct gtagtctggg tccgcgagca aggttgcccg gaactgggtg ttgggggagg  4560
cgcagcaaaa tggcggctgt tcccgagtct tgaatggaag acgcttgtga ggcgggctgt  4620
gaggtcgttg aaacaaggtg gggggcatgg tgggcggcaa gaaccaagg tcttgaggcc  4680
ttcgctaatg cgggaaagct cttattcggg tgagatgggc tggggcacca tctgggacc  4740
ctgacgtgaa gtttgtcact gactggagaa ctcggtttgt cgtctgttgc ggggcggca  4800
gttatggcgg tgccgttggg cagtgcaccc gtacctttgg gagcgcgcgc cctcgtcgtg  4860
tcgtgacgtc acccgttctg ttggcttata atgcagggtg gggccacctg ccggtaggtg  4920
tgcggtaggc ttttctccgt cgcaggacgc agggttcggg cctagggtag gctctcctga  4980
atcgacaggc gccggacctc tggtgagggg agggataagt gaggcgtcag tttctttggt  5040
cggttttatg tacctatctt cttaagtagc tgaagctccg cttggtgaact atgcgctcgg  5100
ggttggcgag tgtgttttgt gaagttttttt aggcacctttt tgaaatgtaa tcatttgggt  5160
caatatgtaa ttttcagtgt tagactagta aattgtccgc taaattctgg ccgttttttgg  5220
cttttttgtt agacgtgttg acaattaatc atcggcatag tatatcggca tagtataata  5280
cgacaaggtg aggaactaaa ccatgaaaaa gcctgaactc accgcgacgt ctgtcgagaa  5340
gtttctgatc gaaaagttcg acagcgtgtc cgacctgatg cagctctcgg agggcgaaga  5400
atctcgtgct ttcagcttcg atgtaggagg gcgtggatat gtcctgcggg taaatagctc  5460
cgccgatggt ttctacaaag atcgttatgt ttatcggcac tttgcatcgg ccgcgctccc  5520
gattccggaa gtgcttgaca ttggggaatt cagcgagagc ctgacctatt gcatctcccg  5580
ccgtgcacag ggtgtcacgt tgcaagacct gcctgaaacc gaactgcccg ctgttctgca  5640
gccggtcgcg gaggccatgg atgcgattgc tgcggccgat cttagccaga cgagcgggtt  5700
cggcccattc ggaccgcaag gaatcggtca atacactcca tggcgtgatt tcatatgcgc  5760
gattgctgat ccccatgtgt atcactggca aactgtgatg gacgacaccg tcagtgcgtc  5820
cgtcgcgcag gctctcgatg agctgatgct ttgggccgag gactgccccg aagtccggca  5880
cctcgtgcac gcggatttcg gctccaacaa tgtcctgacg gacaatggcc gcataacagc  5940
ggtcattgac tggagcgagg cgatgttcgg ggattcccaa tacgaggtcg ccaacatctt  6000
```

```
cttctggagg ccgtggttgg cttgtatgga gcagcagacg cgctacttcg agcggaggca   6060
tccggagctt gcaggatcgc cgcggctccg ggcgtatatg ctccgcattg gtcttgacca   6120
actctatcag agcttggttg acggcaattt cgatgatgca gcttgggcgc agggtcgatg   6180
cgacgcaatc gtccgatccg gagccgggac tgtcgggcgt acacaaatcg cccgcagaag   6240
cgcggccgtc tggaccgatg gctgtgtaga agtactcgcc gatagtggaa accgacgccc   6300
cagcactcgt ccgagggcaa aggaataggg ggatccgctg taagtctgca gaaattgatg   6360
atctattaaa caataaagat gtccactaaa atggaagttt ttcctgtcat actttgttaa   6420
gaagggtgag aacagagtac ctacattttg aatggaagga ttggagctac gggggtgggg   6480
gtggggtggg attagataaa tgcctgctct ttactgaagg ctctttacta ttgctttatg   6540
ataatgtttc atagttggat atcataattt aaacaagcaa aaccaaatta agggccagct   6600
cattcctccc actcatgatc tatagatcta tagatctctc gtgggatcat tgttttttctc   6660
ttgattccca ctttgtggtt ctaagtactg tggtttccaa atgtgtcagt ttcatagcct   6720
gaagaacgag atcagcagcc tctgttccac atacacttca ttctcagtat tgtttttgcca   6780
agttctaatt ccatcagacc tcgacctgca gccctagcc cgggcgccag tagcagcacc   6840
cacgtccacc ttctgtctag taatgtccaa cacctccctc agtccaaaca ctgctctgca   6900
tccatgtggc tcccatttat acctgaagca cttgatgggg cctcaatgtt ttactagagc   6960
ccacccccct gcaactctga gaccctctgg atttgtctgt cagtgcctca ctggggcgtt   7020
ggataatttc ttaaaaggtc aagttccctc agcagcattc tctgagcagt ctgaagatgt   7080
gtgctttttca cagttcaaat ccatgtggct gtttcaccca cctgcctggc cttgggttat   7140
ctatcaggac ctagcctaga agcaggtgtg tggcacttaa cacctaagct gagtgactaa   7200
ctgaacactc aagtggatgc catctttgtc acttcttgac tgtgacacaa gcaactcctg   7260
atgccaaagc cctgcccacc cctctcatgc ccatatttgg acatggtaca ggtcctcact   7320
ggccatggtc tgtgaggtcc tggtcctctt tgacttcata attcctaggg gccactagta   7380
tctataagag gaagagggtg ctggctccca ggccacagcc cacaaaattc cacctgctca   7440
caggttggct ggctcgaccc aggtggtgtc ccctgctctg agccagctcc cggccaagcc   7500
agcaccatgg gtaccccaa gaagaagagg aaggtgcgta ccgatttaaa ttccaattta   7560
ctgaccgtac accaaaattt gcctgcatta ccggtcgatg caacgagtga tgaggttcgc   7620
aagaacctga tggacatgtt cagggatcgc caggcgtttt ctgagcatac ctggaaaatg   7680
cttctgtccg tttgccggtc gtgggcggca tggtgcaagt tgaataaccg gaaatggttt   7740
cccgcagaac ctgaagatgt tcgcgattat cttctatatc ttcaggcgcg cggtctggca   7800
gtaaaaacta tccagcaaca tttgggccag ctaaacatgc ttcatcgtcg gtccgggctg   7860
ccacgaccaa gtgacagcaa tgctgtttca ctggttatgc ggcggatccg aaaagaaaac   7920
gttgatgccg gtgaacgtgc aaaacaggct ctagcgttcg aacgcactga tttcgaccag   7980
gttcgttcac tcatggaaaa tagtgatcgc tgccaggata ctgctaatct ggcatttctg   8040
gggattgctt ataacaccct gttacgtata gccgaaattg ccaggatcag ggttaaagat   8100
atctcacgta ctgacggtgg gagaatgtta atccatattg gcagaacgaa aacgctggtt   8160
agcaccgcag gtgtagagaa ggcacttagc ctgggggtaa ctaaactggt cgagcgatgg   8220
atttccgtct ctggtgtagc tgatgatccg aataactacc tgttttgccg ggtcagaaaa   8280
aatggtgttg ccgcgccatc tgccaccagc cagctatcaa ctcgcgccct ggaagggatt   8340
tttgaagcaa ctcatcgatt gatttacggc gctaaggtaa atataaaatt tttaagtgta   8400
taatgtgtta aactactgat tctaattgtt tgtgtatttt aggatgactc tggtcagaga   8460
tacctggcct ggtctggaca cagtgcccgt gtcgagccg cgcgagatat ggcccgcgct   8520
ggagtttcaa taccggagat catgcaagct ggtggctgga ccaatgtaaa tattgtcatg   8580
aactatatcc gtaacctgga tagtgaaaca ggggcaatgg tgcgcctgct ggaagatggc   8640
gattgatcta gataagtaat gatcataatc agccatatca catctgtaga ggttttactt   8700
gctttaaaaa acctcccaca cctccccctg aacctgaaac ataaaatgaa tgcaattgtt   8760
gttgttaaac ctgcccagt tgcggccaat tccagctgag cgtgcctccg caccattacc   8820
agttggtctg gtgtcaaaaa taataataac cgggcagggg ggatctaagc tctagataag   8880
taatgatcat aatcagccat atcacatctg tagaggtttt acttgcttta aaaaacctcc   8940
cacacctccc cctgaacctg aaacataaaa tgaatgcaat tgttgttgtt aacttgttta   9000
ttgcagctta taatggttac aaataaagca atagcatcac aaatttcaca aataaagcat   9060
ttttttcact gcattctagt tgtggtttgt ccaaactcat caatgtatct tatcatgtct   9120
ggaataactt cgtataatgt atgctatacg aagttatgct agtaactata acggtcctaa   9180
ggtagcgagc tagccgtgga cagatacagc aacgtgagct agttattctg tcctaaagtc   9240
tcagttggaa gatgggagga ttttttgacct ctgtctgctg ggggcaggac caaccaccag   9300
ggaactgcag ccccctgtg ctgagtgcat cagagacttg gaatggaaca cactggcctg   9360
cgacactcat cacaacgaac agaaactgct ttgtacactg aataaacgca gtgaataccc   9420
agctcaggat cacagacaca tgaatgcaaa gttatattag tataaccaag ggtgggaatg   9480
agggcaatta cagataactt atagacatga attactaaca aacaagggca aaatgtttgc   9540
tcataaataa catgaaaata caatatatag tcatatgtat atatacatgt atatatataa   9600
atgacataat atgtatatat ttttacaaat acactgcagg aaaataatat ttttcctcta   9660
cagaagagat tggcaaatct gacatctaaa at                                 9692
```

```
SEQ ID NO: 22            moltype = DNA   length = 160
FEATURE                  Location/Qualifiers
misc_feature             1..160
                         note = Synthetic
misc_feature             1..90
                         note = Mouse Sequence
misc_feature             91..160
                         note = Human Sequence
source                   1..160
                         mol_type = other DNA
                         organism = synthetic construct
SEQUENCE: 22
catgatgttt ctttcttagg aaagccaggg catttctcta ttctccaatc tcttggctca   60
atgcccttgc cctctctttt gttccactag tgaagcctct ccagccaggg gctgaggtcc   120
cggtggtgtg ggcccaggag ggggctcctg cccagctccc                          160
```

-continued

```
SEQ ID NO: 23          moltype = DNA   length = 197
FEATURE                Location/Qualifiers
misc_feature           1..197
                       note = Synthetic
misc_feature           1..60
                       note = Human Sequence
misc_feature           61..66
                       note = XhoI
misc_feature           67..100
                       note = loxP
misc_feature           106..131
                       note = I-CeuI
misc_feature           132..137
                       note = NheI
misc_feature           138..197
                       note = Mouse Sequence
source                 1..197
                       mol_type = other DNA
                       organism = synthetic construct
SEQUENCE: 23
tgttatttac agatacgtga gtttgggcaa attattgttc tctgtgtccc agctgtaaac   60
ctcgagataa cttcgtataa tgtatgctat acgaagttat gctagtaact ataacggtcc  120
taaggtagcg agctagccgt ggacagatac agcaacgtga gctagttatt ctgtcctaaa  180
gtctcagttg gaagatg                                                  197

SEQ ID NO: 24          moltype = DNA   length = 4551
FEATURE                Location/Qualifiers
misc_feature           1..4551
                       note = Synthetic
misc_feature           1..69
                       note = Mouse Sequence
misc_feature           70..3976
                       note = Human Sequence
misc_feature           3977..3982
                       note = XhoI
misc_feature           3983..4016
                       note = LoxP
misc_feature           4022..4047
                       note = I-CeuI
misc_feature           4048..4053
                       note = NheI
misc_feature           4054..4551
                       note = Mouse Sequence
source                 1..4551
                       mol_type = other DNA
                       organism = synthetic construct
SEQUENCE: 24
gtgtgatcac atcccaaagt gggtggccag ggctgggcag agaaaggggg caacttcggg   60
tgtgtgtgac aagggagtgg tgggtgcagt ggtggcggac acagcgatcc cgttttcttc  120
tctctgcacg ctgtcctggc cagactccca gctgcaggag gagctgcggg gcctgagaga  180
gacgttcagc aacttcacag cgagcacgga ggcccaggtc aagggcttga gcacccaggg  240
tgagggcgct ggggcggggc tggggctggg gctggggctg gggggctgtc gggaacgctg  300
agcgagcctc tcccgcagga ggcaatgtgg gaagaaagat gaagtcgcta gagtcccagc  360
tggagaaaca gcagaaggac ctgagtgaag gtcagagagg gagtgtgtgt gtgtgtgtgt  420
gtgtgtgaaa gagagtgaga atgtgtggat gtgtgtgaga aagtgtgaga gtgtgtgaat  480
gtgtgtgaga atgagaggga gtgtgtgtgt gtgtgagtct gtgtgtgaga atgagggggga  540
gtgtgttttg ggtgtgtgta tgagagcctt gtgtggatgt gagaatgaga gggagtgtgt  600
atgtctgtga gtgtgagaat gagatggagt gtgtgtgagt ctgtgtgtga gaatgaggtg  660
tgtgtgtgtg agaatgagat ggtgtgtgtg tgggaatgag aggggggtgtg tgtctgagtg  720
tgagaatgag atagagtgtg tgtgagacag tctgtgtgag tgagagggga gtgtgtgtag  780
agtgtgagaa tgacggagtg tgtctgtgag tgtgataatg aggtgtgtgt gagtctgagt  840
gtaagaatga gatggggtgt gtgtgtctgt gagtgtgaga gtgtgagaat gagggggtgtt  900
tgtgtctgag tgtgagtctg tgagtgtgag aatgagatgg ggtgtgtgag tgagtgtgag  960
aatgagatgg ggtgtgtgtt tctgtgagtg tgtgtgagtg tgttgcgtg agaatgagat 1020
ggggtgtgtg tgagtgtgag aatgagatgg ggtgtgtgtc tgtgtgtgag aatgagatgg 1080
gtgtgtgtgt gacagagtct gagtgtgaga atgagaggga gtgtgtgtga gtgtgagaat 1140
gagaaggagt ggatgggtgt gtgagtctgt gtgaatgagg gagtgggtgt gtgtacgagt 1200
gtgagtctgt gtttatgtgt gagaatgtgt cagtgtatgt gtgtgagaac gtgtgtatgt 1260
gtgttagtgt gtgttgcgtg tgtgggggaa tgagagggat tgtgtctgtg agtgtgagaa 1320
tgagatggag tgtctgtgag actgtgtgtg aggagtgtga gtgtgtgtga gaatgagatg 1380
ggtgtgtgtg tctgagtgtg tgtctgtgag aatgagaggg agtgtgtgtg tgtgtgagag 1440
cctgtgtgaa aatgagaagg agtgtggatg ggtgtttgtg agtgggagag tctgtgtgtt 1500
tatgtgtgtg agaatgaggg agtgtgggtg tgtgtgcgaa tgtgagtctg tgtttatgtg 1560
tgtgagaatg tgtcagtgta tgtgagaacg tgtgtgttag tgtgttgcgt gtgtgagaat 1620
gtaagtatat gtgtaagtgc atgtgagtcg tgtgtatgtgc gtgttgtgtg aatgtgcatt 1680
gtgtgtgcat gtgtgaaaga gtatatgtgt gttgtgggtg agtgtgtgtg gtgtgtgtag 1740
tgggtgaggg tgtgttgtat gtgtgggtgt gcgttgtgtg aatgtgtgta tgtgggtgag 1800
ggtgtgtgtg cctgtgtgag ggtgtgttgt ggttttttgtg tgtgtttggg tgagggtgtg 1860
ttgtgtgtgt gtgtgggtga aggtgtgttg tgtgtgtcgt gggtgaaggt gtgttgtgtg 1920
```

-continued

```
tgtagtgact gtagattagg gtgtgttccg tgtgtgtgtg tgagggtgta tgttgtgggt   1980
gttttgtgtg tgagtgggtg tgtaagggtg tgttgtgtgt atgtgggtta aggtgtgtta   2040
tgcgtgaggg tgtattgtgt gtgtgtttg tgtgtgttgt gtgtatgtgg gttagggtgt     2100
gttgtgtgtt tgtgtgtttt gtgtgttgtc tgtgtatgtg ggttacggtg tgttgtgcgt    2160
gtgagggtgt gttgtgtatg gtgtgtttg tgtgttgtgt gagtgtgtat gtgagttagg      2220
gtgtgttgtg tctatgtatg tgtgtgtaag ggtgtgttgt gtgtctgtgg gtgtgttttg     2280
tgtatgtggg ttagggtgtg ttgtgtgttc tgtattgtgt gttttatgtg ttgtctgtat    2340
gtgggttatg tgtgttgtgt gtgttgtgga tgtatgtggg ttagggtgtg ttgtgtgtct    2400
ctgtgtgttg tctgcgtttg tgtctgtggg ttagggtgtg ttgtatgtgt tgtgttttgt    2460
gtgttgtccg tgtgtgtgta tgtgggttag gttgtgttgt tgtgtgttgt atattgtctg    2520
tgtgtgtgtg ttaggatgtg ttgtgtgtct gtgtgagtgt gtgtgtaagg gtgtgttgtg    2580
tgtgtaggag tgtgtgtgtg tgtgtgtatg ggggtctctc aggccaactc cgctgctgtt    2640
tgtggcaatg cgacgggtgt tcgggtccca gcaggaggat gtagggctga cctcgtttcc    2700
cgtttccctc cccgtggttt ccgcatctcc tcccgctccc ctccgcccgg tctccccaga    2760
tcactccagc ctgctgctcc acgtgaagca gttcgtgtct gacctgcgga gcctgagctg    2820
tcagatggcg gcgctccagg gcaatggtaa ggaggccagc ccggcccgct ctctgcctcc    2880
cccccttctct gggcagcgct tagccctgc gccccgtttc tcccgctcag gctcagaaag     2940
gacctgctgc ccggtcaact gggtggagca cgagcgcagc tgctactggt tctctcgctc    3000
cgggaaggcc tgggctgacg ccgacaacta ctgccggctg gaggacgcgc acctggtggt    3060
ggtcacgtcc tgggaggagc aggtgaggac ccggagggtc tgggaggctg gctggcctcg    3120
gagagatcac caccgccctt ctctctcctc agaaatttgt ccagcaccac ataggccctg    3180
tgaacacctg gatgggcctc cacgaccaaa acgggccccg gaagtgggtg gacgggacgg    3240
actacgagac gggcttcaag tgagtgcgcg ccctccctcg gcctgggtcc ggccgccttc    3300
gcgccctggg gccctgggct gaggagtctg gagcgacccg cctgcggatc cgacctcctg    3360
gggcccacag ctggctctgt ccccaggaac tggaggccgg agcagccgga cgactggtac    3420
ggccacgggc tcggaggagg cgaggactgt gcccacttca ccgacgacgg ccgctggaac    3480
gacgacgtct gccagaggcc ctaccgctgg gtctgcgaga cagagctgga caaggccagc    3540
caggagccac ctctcctta atttatttct tcaatgcctc gacctgccgc aggggtccgg      3600
gattgggaat ccgcccatct gggggcctct tctgctttct cgggaatttt catctaggat    3660
tttaagggaa ggggaaggat agggtgatgt tccgaaggtg aggagcttga aacccgtggc   3720
gctttctgca gtttgcaggt tatcattgtg aactttttt tttaagagt aaaaagaaat       3780
atacctaaac cttctgttag ttgtctggtt attggggatt cggaagcagg agtgggctgg    3840
ttggcattac gaagccttag cgggtgctgt ggcatcatga gaactgtgtg ggctttgggc    3900
cagaatggcc agactttgtt atttacagat acgtgagttt gggcaaatta ttgttctctg    3960
tgtcccagct gtaaacctcg agataacttc gtataatgta tgctatacga agttatgcta    4020
gtaactataa cggtcctaag gtagcgagct agccgtggac agatacagca acgtgagcta   4080
gttattctgt cctaaagtct cagttggaag atgggaggat ttttgacctc tgtctgctgg    4140
gggcaggacc aaccaccagg gaactgcagc cccctgtgc tgagtgcatc agagacttgg      4200
aatgaaacac actggcctgc gacactcatc acaacgaaac tgctt tgtacactga           4260
ataaacgcag tgaataccca gctcaggatc acagacacat gaatgcaaag ttatattagt    4320
ataaccaagg gtgggaatga gggcaattac agataactta tagacatgaa ttactaacaa    4380
aacagggcaa aatgtttgct cataaataac atgaaaatac aatatatagt catatgtata    4440
tacacatgta tatatataaa tgacataata tgtatatatt tttacaaata cactgcagga    4500
aaataatatt tttcctctac agaagagatt ggcaaatctg acatctaaaa t             4551
```

```
SEQ ID NO: 25                 moltype = AA   length = 10
FEATURE                       Location/Qualifiers
REGION                        1..10
                              note = Synthetic
source                        1..10
                              mol_type = protein
                              organism = synthetic construct
SEQUENCE: 25
EQKLISEEDL                                                              10

SEQ ID NO: 26                 moltype = DNA   length = 30
FEATURE                       Location/Qualifiers
misc_feature                  1..30
                              note = Synthetic
source                        1..30
                              mol_type = other DNA
                              organism = synthetic construct
SEQUENCE: 26
gaacaaaaac tcatctcaga agaggatctg                                       30

SEQ ID NO: 27                 moltype = AA   length = 63
FEATURE                       Location/Qualifiers
source                        1..63
                              mol_type = protein
                              organism = Homo sapiens
SEQUENCE: 27
SQNSQLQEEL RGLRETFSNF TASTEAQVKG LSTQGGNVGR KMKSLESQLE KQQKDLSEDH   60
SSL                                                                    63

SEQ ID NO: 28                 moltype = AA   length = 118
FEATURE                       Location/Qualifiers
source                        1..118
                              mol_type = protein
                              organism = Homo sapiens
```

```
SEQUENCE: 28
HERSCYWFSR SGKAWADADN YCRLEDAHLV VVTSWEEQKF VQHHIGPVNT WMGLHDQNGP    60
WKWVDGTDYE TGFKNWRPEQ PDDWYGHGLG GGEDCAHFTD DGRWNDDVCQ RPYRWVCE     118

SEQ ID NO: 29              moltype = AA   length = 39
FEATURE                    Location/Qualifiers
source                     1..39
                           mol_type = protein
                           organism = Mus musculus
SEQUENCE: 29
MTKDYQDFQH LDNDNDHHQL RRGPPPTPRL LQRLCSGSR                           39

SEQ ID NO: 30              moltype = AA   length = 21
FEATURE                    Location/Qualifiers
source                     1..21
                           mol_type = protein
                           organism = Mus musculus
SEQUENCE: 30
LLLLSSSLSI LLLVVVCVIT S                                             21

SEQ ID NO: 31              moltype = AA   length = 229
FEATURE                    Location/Qualifiers
source                     1..229
                           mol_type = protein
                           organism = Homo sapiens
SEQUENCE: 31
NSQLQEELRG LRETFSNFTA STEAQVKGLS TQGGNVGRKM KSLESQLEKQ QKDLSEDHSS    60
LLLHVKQFVS DLRSLSCQMA ALQGNGSERT CCPVNWVEHE RSCYWFSRSG KAWADADNYC   120
RLEDAHLVVV TSWEEQKFVQ HHIGPVNTWM GLHDQNGPWK WVDGTDYETG FKNWRPEQPD   180
DWYGHGLGGG EDCAHFTDDG RWNDDVCQRP YRWVCETELD KASQEPPLL              229

SEQ ID NO: 32              moltype = DNA   length = 20
FEATURE                    Location/Qualifiers
misc_feature               1..20
                           note = Synthetic
source                     1..20
                           mol_type = other DNA
                           organism = synthetic construct
SEQUENCE: 32
ggagtaccag ctcccgtacg                                              20

SEQ ID NO: 33              moltype = DNA   length = 43
FEATURE                    Location/Qualifiers
misc_feature               1..43
                           note = Synthetic
source                     1..43
                           mol_type = other DNA
                           organism = synthetic construct
SEQUENCE: 33
ctcttctgag atgagttttt gttcgttgcc tctctggagg ttg                    43

SEQ ID NO: 34              moltype = DNA   length = 43
FEATURE                    Location/Qualifiers
misc_feature               1..43
                           note = Synthetic
source                     1..43
                           mol_type = other DNA
                           organism = synthetic construct
SEQUENCE: 34
aaactcatct cagaagagga tctgagacaa gcagctaccg cag                    43

SEQ ID NO: 35              moltype = DNA   length = 18
FEATURE                    Location/Qualifiers
misc_feature               1..18
                           note = Synthetic
source                     1..18
                           mol_type = other DNA
                           organism = synthetic construct
SEQUENCE: 35
tccgcccgct gtttaaac                                                18

SEQ ID NO: 36              moltype = DNA   length = 21
FEATURE                    Location/Qualifiers
misc_feature               1..21
                           note = Synthetic
source                     1..21
                           mol_type = other DNA
                           organism = synthetic construct
SEQUENCE: 36
```

```
ggaacccccta gtgatggagt t                                                  21

SEQ ID NO: 37              moltype = DNA   length = 16
FEATURE                    Location/Qualifiers
misc_feature               1..16
                           note = Synthetic
source                     1..16
                           mol_type = other DNA
                           organism = synthetic construct
SEQUENCE: 37
cggcctcagt gagcga                                                         16

SEQ ID NO: 38              moltype = DNA   length = 21
FEATURE                    Location/Qualifiers
misc_feature               1..21
                           note = Synthetic
source                     1..21
                           mol_type = other DNA
                           organism = synthetic construct
SEQUENCE: 38
cactccctct ctgcgcgctc g                                                   21

SEQ ID NO: 39              moltype = AA   length = 291
FEATURE                    Location/Qualifiers
source                     1..291
                           mol_type = protein
                           organism = Macaca fascicularis
SEQUENCE: 39
MTKEYQDLQH LDNEESDHHQ LGKGPPPPQS LLRRLCSGPR LLLLSLGLSL LLLVVVCVIG         60
SQNAQLQREL RGLRETLSNF TASTEAQVKG LSTQGGNVGR KMKSLESQLE KQQKDLSEDH         120
SSLLLHVKQF VSDLRSLSCQ MAALQGNGSE RACCPVNWVE HERSCYWFSR SGKAWADADN         180
YCRLEDAHLV VVTSWEEQKF VQHHIGPVNT WMGLHDQNGP WKWVDGTDYE TGFKNWRPEQ         240
PDDWYGHGLG GGEDCAHFTD DGRWNDDVCQ RPYRWVCETE LDKASQEPPL L                  291

SEQ ID NO: 40              moltype = DNA   length = 876
FEATURE                    Location/Qualifiers
source                     1..876
                           mol_type = genomic DNA
                           organism = Macaca fascicularis
SEQUENCE: 40
atgaccaagg agtatcagga cctgcagcat ctggacaatg aggagagtga ccaccatcag         60
ctcggaaaag ggccacctcc tccgcagtcc ctcctgcggc gtctctgctc cggccctcgc         120
ctcctcctgc tctccctggg cctcagcctc ctgctgctg tggttgtctg tgtgatcgga         180
tcccaaaacg cccagctgca gcgggagctg cggggcctga gagagacgct cagcaacttc         240
acagcgagca ccgaggccca ggtcaagggc ttgagcaccc agggaggcaa tgtgggaaga         300
aagatgaagt cgctggagtc ccagctggag aaacagcaga aggacttgag tgaagatcac         360
tccagcctgc tgctccacgt gaagcagttc gtgtctgacc tgcggtctct gagctgtcag         420
atggcggcgc tccagggcaa tggctcggaa agggcctgct gcccagtcaa ctgggtggag         480
cacgagcgca gctgctactg gttctctcgc tccgggaagg cctgggccga cgccgacaac         540
tactgccggc tggaggacgc gcacctggtg gtggtcacgt cctgggagga gcagaaattt         600
gtccagcac acataggtcc tgtgaacacc tggatggcc tccacgacca aaacgggccc           660
tggaagtggg tggacgggac ggactacgag acgggcttca agaactgag accggagcag          720
ccggacgact ggtacggcca cgggctcggg ggaggggagg actgtgccca cttcaccgac         780
gacggccgct ggaacgacga cgtctgccag aggccctacc gctgggtctg cgagacagag         840
ctggacaagg ccagtcagga gccacctctc ctttaa                                   876

SEQ ID NO: 41              moltype = AA   length = 284
FEATURE                    Location/Qualifiers
source                     1..284
                           mol_type = protein
                           organism = Rattus norvegicus
SEQUENCE: 41
MTKDYQDFQH LDNENDHHQL QRGPPPAPRL LQRLCSGFRL FLLSLGLSIL LLVVVCVITS         60
QNSQLREDLR VLRQNFSNFT VSTEDQVKAL TTQGERVGRK MKLVESQLEK HQEDLREDHS         120
RLLLHVKQLV SDVRSLSCQM AALRGNGSER ICCPINWVEY EGSCYWFSSS VKPWTEADKY         180
CQLENAHLVV VTSWEEQRFV QQHMGPLNTW IGLTDQNGPW KWVDGTDYET GFKNWRPGQP         240
DDWYGHGLGG GEDCAHFTTD GHWNDDVCRR PYRWVCETEL GKAN                          284

SEQ ID NO: 42              moltype = DNA   length = 855
FEATURE                    Location/Qualifiers
source                     1..855
                           mol_type = genomic DNA
                           organism = Rattus norvegicus
SEQUENCE: 42
atgacaaagg attatcaaga tttccagcac ttggacaatg agaacgacca ccatcaactc         60
cagagagggc cacctcccgc tccaaggctc ttgcagcgac tctgtctggg attccgtctc         120
ttcctgcttt ccctgggcct cagcatcctg ctgctggtgg ttgtctgtgt gatcacatcc         180
caaaattccc aactccggga agatctgcgg gttctaaggc agaatttcag caactttacc         240
gtgagcactg aggaccaggt caaggccctg accacccagg agagagagt gggaagaaag         300
```

-continued

```
atgaagttag tcgagtcaca gctggaaaaa catcaggagg atctgaggga agaccactct   360
agattgctac tgcatgtaaa gcagttagtg tctgacgtgc gaagcttgag ctgccagatg   420
gccgcacttc ggggcaatgg ctctgaaagg atctgctgcc ccatcaactg ggtggagtat   480
gaaggcagct gctactggtt ctccagctct gtgaagcctt ggacggaagc tgacaagtac   540
tgccagctgg agaacgccca cctggtggtg gtgacttcct gggaggagca gagattcgtc   600
cagcaacaca tgggcccctt aaatacttgg attggcctaa ctgaccagaa cggaccctgg   660
aaatgggtgg atgggacaga ctatgagaca ggcttcaaga actggagacc agggcagcca   720
gatgactggt acggacatgg gcttggaggg ggtgaagact gtgcccactt caccaccgat   780
ggccactgga atgatgacgt ctgcaggagg ccctaccgct gggtctgtga gacagagttg   840
ggcaaggcca attag                                                     855
```